(12) United States Patent
Matsushima et al.

(10) Patent No.: US 7,759,066 B2
(45) Date of Patent: Jul. 20, 2010

(54) MOLECULE ASSOCIATING WITH INTRACELLULAR C-TERMINAL DOMAIN OF RECEPTOR

(75) Inventors: Kouji Matsushima, Matsudo (JP); Yuya Terashima, Tokyo (JP)

(73) Assignee: ECI, Inc., Tokyo (JP)

( * ) Notice: Subject to any disclaimer, the term of this patent is extended or adjusted under 35 U.S.C. 154(b) by 0 days.

(21) Appl. No.: 12/191,213

(22) Filed: Aug. 13, 2008

(65) Prior Publication Data

US 2009/0081693 A1 Mar. 26, 2009

Related U.S. Application Data

(62) Division of application No. 10/504,879, filed as application No. PCT/JP03/01699 on Feb. 18, 2003, now abandoned.

(30) Foreign Application Priority Data

Feb. 19, 2002 (JP) .............................. 2002-042262

(51) Int. Cl.
*C12Q 1/68* (2006.01)
*C07H 21/04* (2006.01)
(52) U.S. Cl. ...................... 435/6; 435/69.1; 435/320.1; 435/325; 530/350; 536/23.5
(58) Field of Classification Search ........................ None
See application file for complete search history.

(56) References Cited

FOREIGN PATENT DOCUMENTS

| CN | 1333264 A | 1/2002 |
|---|---|---|
| EP | 1074617 A2 | 2/2001 |
| WO | WO-02/081731 A2 | 10/2002 |

OTHER PUBLICATIONS

Oppermann M. et al., Differential Effects of CC Chemokines on CC CHemokine Receptor 5 (CCR5) Phosphorylation and identification of Phosphorylation sites on the CCR5 Carboxyl Terminus, J. Biol. Chem., 1999, 274 (13), p. 8875-85.
J. Gosling et al., Proc. Nat'l. Acad. of Sci. USA, vol. 94, pp. 5061-5066 (1997).
Lefkowitz, Cell, vol. 74, pp. 409-412 (1993).
Arai et al., J. Biolog. Chem., vol. 272, No. 40, pp. 25037-25042 (1997).
Database EMBL Online! (Mar. 9, 2001), "*Homo sapiens* pericentrin 1, nRNA (cDNA clone MGC:3092 Image:3349383), complete cds." XP002352673.
Database EMBL "Online! (Nov. 2, 2002), "UI-H-FT1-bhy-m-07-0-UI. s1 NCI_CGAP_ FT1 *Homo sapiens* cDNA clone UI-H-FT1-bhy-m-07-0-UI 3", mRNA sequence." XP002352674.
Database EMBL Online! (Mar. 12, 1999), "*Homo sapiens* mRNA; EST DKFZp434N0917_r1 (from clone DKFZp434N0917)" XP002352675.

Terashima Yuya et al., "Pivotal function for cytoplasmic protein FROUNT in CCR2-mediated monocyte chemotaxis." Nature Immunology. Aug. 2005, vol. 6, No. 8, Aug. 2005, pp. 827-835, XP002352669 ISSN: 1529-2908.
Murphy et al., Pharmacological Reviews, vol. 52, No. 1, pp. 145-176 (2000).
Baggiolini, Nature, vol. 392, pp. 565-568 (Apr. 1998).
Condliffe et al., Nature, vol. 404, pp. 135, 137 (Mar. 2000).
Gerard et al., Nature Immunology, vol. 2, No. 2, pp. 108-115 (Feb. 2001).
Yoshimura et al., Proc. Nat'l Acad. Sci. USA, vol. 84, pp. 9233-9237 (Dec. 1987).
Walz et al., Biochemical and Biophysical Research Communications, vol. 149, No. 2, pp. 755-761 (Dec. 1987).
Matsushima et al., The Journal of Experimental Medicine, vol. 169, pp. 1485-1490, (Apr. 1989).
Yoshimura et al., The Journal of Experimental Medicine, vol. 169, pp. 1449-1459 (Apr. 1989).
Howard et al., Journal of Clinical Immunology, vol. 19, No. 5, pp. 280-292 (1999).
Sallusto et al., Annu. Rev. Immunol., vol. 18, pp. 593-620 (2000).
Kunkel et al., Immunology Today, vol. 16, No. 12, pp. 559-561 (1995).
Charo et al., Proc. Nat'l Acad. Sci USA, vol. 91, pp. 2752-2756 (Mar. 1994).
Boring et al., Nature, vol. 394, pp. 894-897 (Aug. 1998).
Gu et al., Molecular Cell, vol. 2, pp. 275-281 (Aug. 1998).
Wada et al., The FASEB Journal, vol. 10, pp. 1418-1425 (1998).
Fife et al., J. Exp. Med., vol. 192, No. 6, pp. 899-905 (Sep. 2000).
Izikson et al., J. Exp. Med., vol. 192, No. 7, pp. 1075-1080 (Oct. 2000).
Boring et al., The Journal of Clinical Investigation, vol. 100, No. 10, pp. 2552-2561 (Nov. 1997).
Kurihara et al., J. Exp. Med., vol. 186, No. 10, pp. 1757-1762 (Nov. 1997).
Kuziel et al., Proc. Natl Acad. Sci. USA, vol. 94, pp. 12053-12058 (Oct. 1997).
Lu et al., J. Exp. Med., vol. 187, No. 4, pp. 601-608 (Feb. 1998).

(Continued)

*Primary Examiner*—Kimberly Chong
(74) *Attorney, Agent, or Firm*—Birch, Stewart, Kolasch & Birch, LLP.

(57) ABSTRACT

Concerning intracellular signal transduction mechanism, there has been drawn a novel hypothesis that, even in the case where phosphorylation does not occur in the intracellular C-terminal domain of a receptor, an unknown molecule associates with the Pro-C terminal domain of a G protein-coupled receptor for each chemokine and thus leukocyte chemotaxis depending on the receptor is controlled. To examine this hypothesis and clarify therapeutic targets in inflammatory diseases as well as other various diseases, attempts are made to search for a CCR2-binding protein.

As a result, a novel cytoplasmic protein associating directly and specifically with the Pro-12-C-terminal domain of CCR2 is found out and it is clarified that this protein forms clusters with CCR2 after stimulation with CCL2. Thus, it is confirmed that there is a novel signal transduction system in the G protein relating signal transduction in the CCL2-CCR2 pathway. It is also found out that this novel protein associates with the intracellular C-terminal domain of a receptor CCR5 too.

4 Claims, 16 Drawing Sheets

OTHER PUBLICATIONS

Maghazachi, The International Journal of Biochemistry & Cell Biology, vol. 32, pp. 931-943 (2000).
Parent et al., Science, vol. 284, pp. 765-770 (Apr. 1999).
Penn et al., Trends Cardiovasc. Med., vol. 10, No. 2, pp. 81-89 (2000).
Mellado et al., Annu. Rev. Immunol., vol. 19, pp. 397-421 (2001).
Hall et al., The Journal of Cell Biology, vol. 145, No. 5, pp. 927-932 (May 1999).
Ben-Baruch et al., The Journal of Biological Chemistry, vol. 270, No. 16, pp. 9121-9128 (1995).
Kim et al., The Journal of Biological Chemistry, vol. 272, No. 43, pp. 27313-27318 (1997).
Hsu et al., The Journal of Biological chemistry, vol. 272, No. 47, pp. 29426-29429 (Nov. 1997).
Richardson et al., The Journal of Biological Chemistry, vol. 273, No. 17, pp. 10690-10695 (1998).
Kraft et al., The Journal of Biological Chemistry, vol. 276, No. 37, pp. 34408-34418 (2001).
Tsao et al, Pharmacology & Therapeutics, vol. 89, pp. 139-147 (2001).
Ferguson, Pharmacological Reviews, vol. 53, No. 1, pp. 1-24 (2001).
Sambrano et al., The Journal of Biological Chemistry, vol. 274, No. 29, pp. 20178-20184 (1999).
Le Gouill et al., The Journal of Biological Chemistry, vol. 274, No. 18, pp. 12548-12554 (1999).
Shibata et al., Biochemical and Biophysical Research Communications, vol. 218, pp. 383-389 (1996).
O'Connor et al., Science, vol. 286, pp. 1180-1184 (Nov. 1999).
Arai et al., Proc. Natl. Acad. Sci. USA, vol. 94, pp. 14495-14499 (Dec. 1997).
Jin et al., Science, vol. 287, pp. 1034-1036 (Feb. 2000).
Parent et al., Cell, vol. 95, pp. 81-91 (Oct. 1998).
Fukui et al., Nature, vol. 412, pp. 826-831 (2001).
Murai et al., The Journal of Clinical Investigation, vol. 104, No. 1, pp. 49-57 (Jul. 1999).
Onai et al., Blood, vol. 96, No. 6, pp. 2074-2080 (Sep. 2000).
Doxsey et al., Cell, vol. 76, pp. 639-650 (Feb. 1994).
Cronshaw et al., The Journal of Cell Biology, vol. 158, No. 5, pp. 915-927 (Sep. 2002).
Loiodice et al., Molecular Biology of the Cell, vol. 15, pp. 3333-3344 (Jul. 2004).
Prosperi et al., J. Biolog. Chem., vol. 268, No. 15, pp. 11050-11056 (1993).

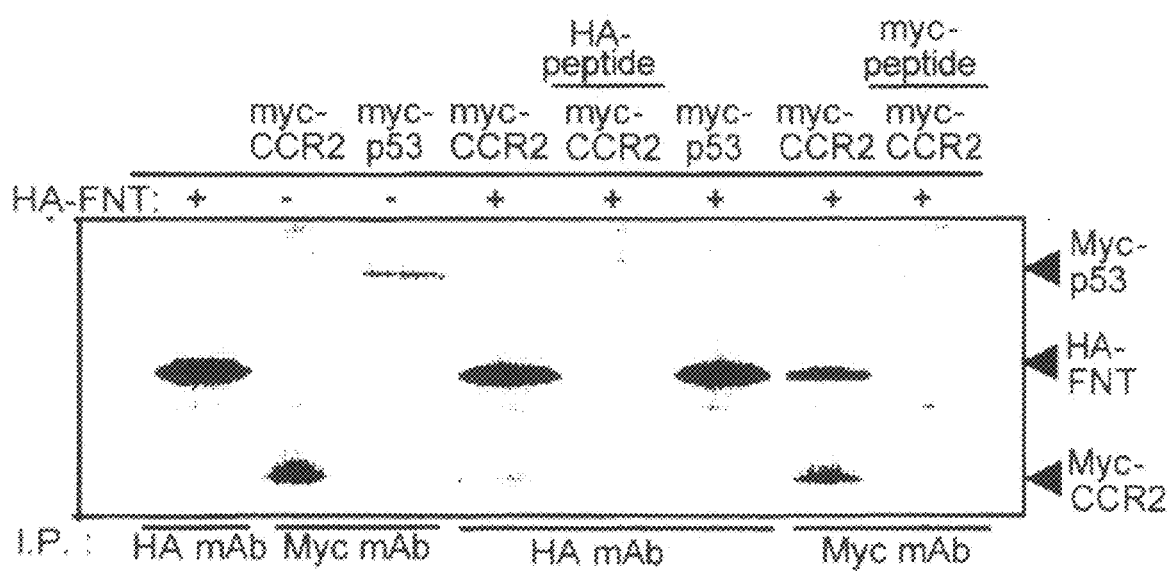

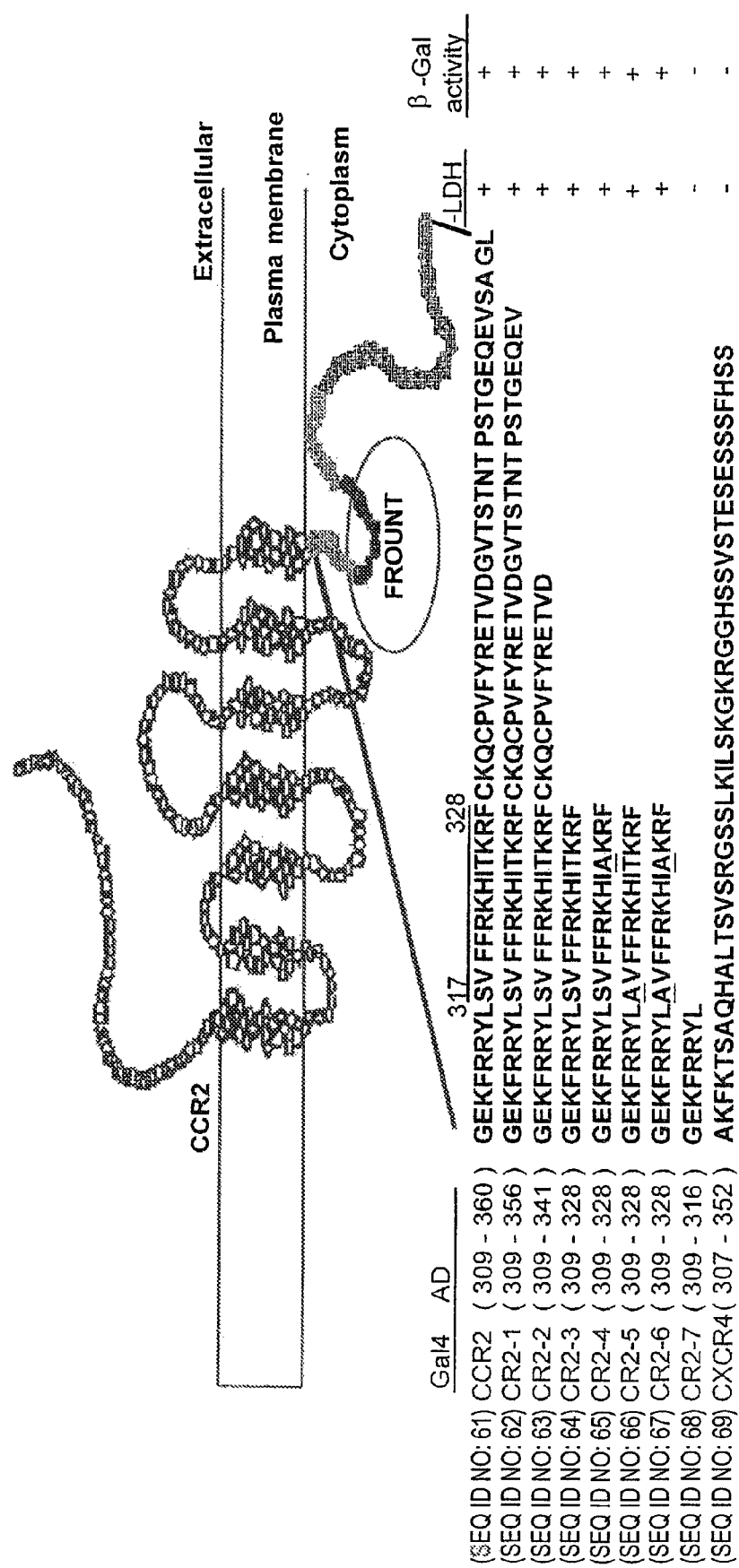

Fig. 4

SEQ ID NO: 2

```
         10          20          30          40          50          60
MEELDGEPTV  TLIPGVNSKK  NQMYFDWGPG  EMLVCETSFN  KKEKSEMVPS  CPFIYIIRKD
         70          80          90         100         110         120
VDVYSQILRK  LFNESHGIFL  GLQRIDEELT  GKSRKSQLVR  VSKNYRSVIR  ACMEEMHQVA
        130         140         150         160         170         180
IAAKDPANGR  QFSSQVSILS  AMELIWNLCE  ILFIEVAPAG  PLLLHLLDWV  RLHVCEVDSL
        190         200         210         220         230         240
SADVLGSENP  SKHDSFWNLV  TILVLQGRLD  EARQMLSKEA  DASPASAGIC  RIMGDLMRTM
        250         260         270         280         290         300
PILSPGNTQT  LTELELKWQH  WHEECERYLQ  DSTFATSPHL  ESLLKIMLGD  EAALLEQKEL
        310         320         330         340         350         360
LSNWYHFLVT  RLLYSNPTVK  PIDLHYYAQS  SLDLFLGGES  SPEPLDNILL  AAFEFDIHQV
        370         380         390         400         410         420
IKECSIALSN  WWFVAHLTDL  LDHCKLLQSH  NLYFGSNMRE  FLLLEYASGL  FAHPSLWQLG
        430         440         450         460         470         480
VDYFDYCFPL  GRVSLELHYE  IPLNTEQKA  LKVLRICEQR  QMTEQVRSIC  KILAMKAVRN
        490         500         510         520         530         540
NRLGSALSWS  IRAKDAAFAT  LVSDRFLRDY  CERGCFSDLD  LIDNLGPAMM  LSDRLTFLGK
        550         560         570         580         590         600
YREFHRMYGE  KRFADAASLL  LSLMTSRIAF  RSFWMTLLTD  ALPLLEQKQV  IFSAEQIYEL
        610         620         630         640         650         660
MRCLEDLTSR  RPVHGESDTE  QLQDDDIETT  KVEMLRLSLA  RNLARAIIRE  GSLEGS....
```

Fig. 5
(a) 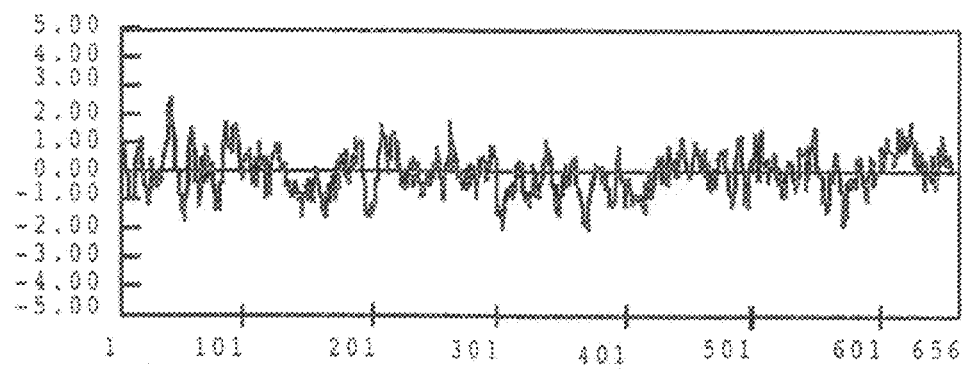
(b) 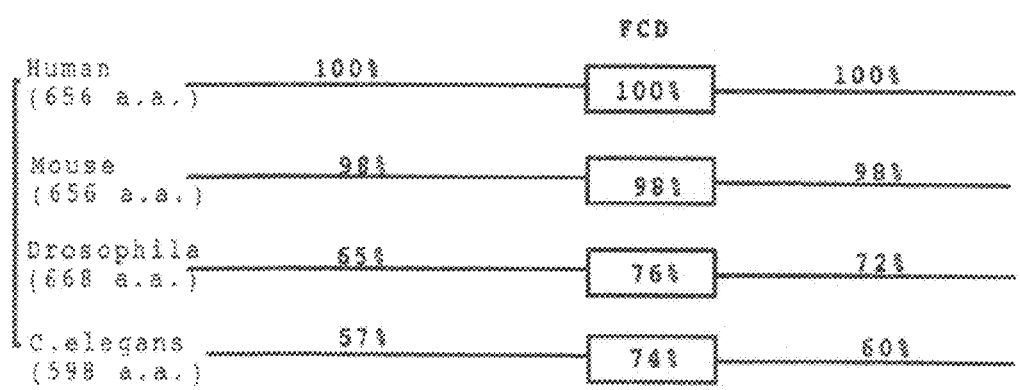
(c) 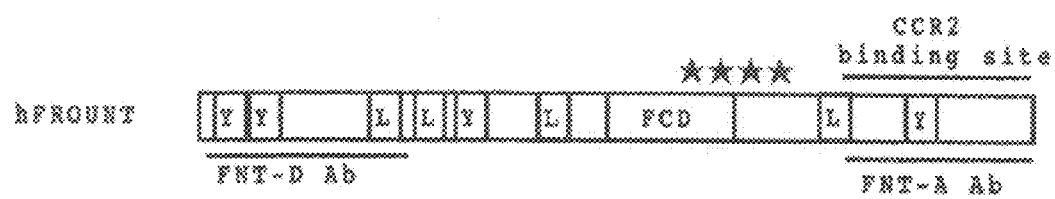

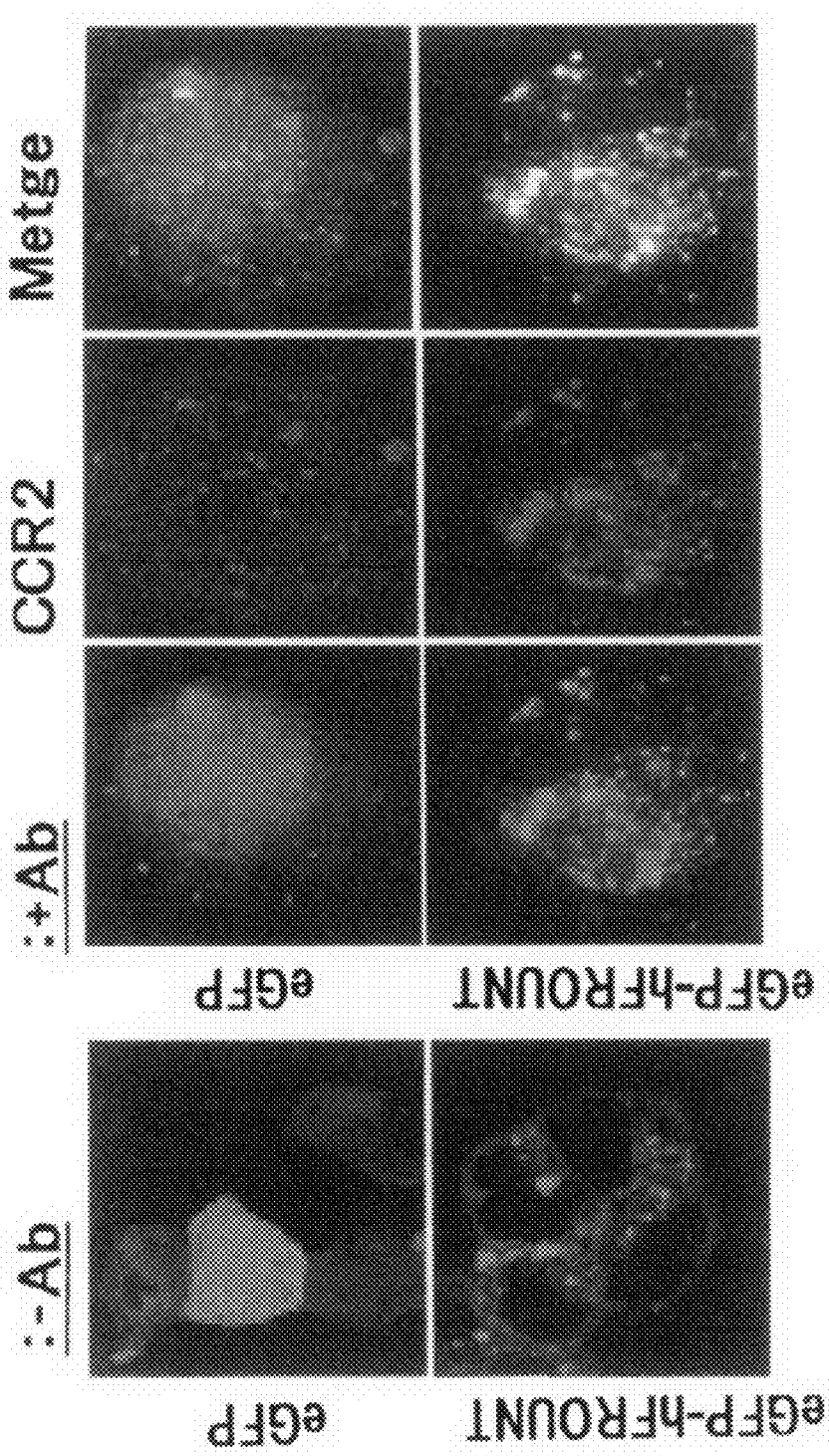

Fig. 7

SEQ ID NO: 2

MetGluGluLeuAspGlyGluProThrValThrLeuIleProGlyValAsnSerLysLysAsnGlnMet
TyrPheAspTrpGlyProGlyGluMetLeuValCysGluThrSerPheAsnLysLysGluLysSerGlu
MetValProSerCysProPheIleTyrIleIleArgLysAspValAspValTyrSerGlnIleLeuArg
LysLeuPheAsnGluSerHisGlyIlePheLeuGlyLeuGlnArgIleAspGluGluLeuThrGlyLys
SerArgLysSerGlnLeuValArgValSerLysAsnTyrArgSerValIleArgAlaCysMetGluGlu
MetHisGlnValAlaIleAlaAlaLysAspProAlaAsnGlyArgGlnPheSerSerGlnValSerIle
LeuSerAlaMetGluLeuIleTrpAsnLeuCysGluIleLeuPheIleGluValAlaProAlaGlyPro
LeuLeuLeuHisLeuLeuAspTrpValArgLeuHisValCysGluValAspSerLeuSerAlaAspVal
LeuGlySerGluAsnProSerLysHisAspSerPheTrpAsnLeuValThrIleLeuValLeuGlnGly
ArgLeuAspGluAlaArgGlnMetLeuSerLysGluAlaAspAlaSerProAlaSerAlaGlyIleCys
ArgIleMetGlyAspLeuMetArgThrMetProIleLeuSerProGlyAsnThrGlnThrLeuThrGlu
LeuGluLeuLysTrpGlnHisTrpHisGluGluCysGluArgTyrLeuGlnAspSerThrPheAlaThr
SerProHisLeuGluSerLeuLeuLysIleMetLeuGlyAspGluAlaAlaLeuLeuGlnLysGlu
LeuLeuSerAsnTrpTyrHisPheLeuValThrArgLeuLeuTyrSerAsnProThrValLysProIle
AspLeuHisTyrTyrAlaGlnSerSerLeuAspLeuPheLeuGlyGlyGluSerSerProGluProLeu
AspAsnIleLeuLeuAlaAlaPheGluPheAspIleHisGlnValIleLysGluCysSerIleAlaLeu
SerAsnTrpTrpPheValAlaHisLeuThrAspLeuLeuAspHisCysLysLeuLeuGlnSerHisAsn
LeuTyrPheGlySerAsnMetArgGluPheLeuLeuLeuGluTyrAlaSerGlyLeuPheAlaHisPro
SerLeuTrpGlnLeuGlyValAspTyrPheAspTyrCysProGluLeuGlyArgValSerLeuGluLeu
HisIleGluArgIleProLeuAsnThrGluGlnLysAlaLeuLysValLeuArgIleCysGluGlnArg
GlnMetThrGluGlnValArgSerIleCysLysIleLeuAlaMetLysAlaValArgAsnAsnArgLeu
GlySerAlaLeuSerTrpSerIleArgAlaLysAspAlaAlaPheAlaThrLeuValSerAspArgPhe
LeuArgAspTyrCysGluArgGlyCysPheSerAspLeuAspLeuIleAspAsnLeuGlyProAlaMet
MetLeuSerAspArgLeuThrPheLeuGlyLysTyrArgGluPheHisArgMetTyrGlyGluLysArg
PheAlaAspAlaAlaSerLeuLeuLeuSerLeuMetThrSerArgIleAlaProArgSerPheTrpMet
ThrLeuLeuThrAspAlaLeuProLeuLeuGluGlnLysGlnValIlePheSerAlaGluGlnThrTyr
GluLeuMetArgCysLeuGluAspLeuThrSerArgArgProValHisGlyGluSerAspThrGluGln
LeuGlnAspAspAspIleGluThrThrLysValGluMetLeuArgLeuSerLeuAlaArgAsnLeuAla
ArgAlaIleIleArgGluGlySerLeuGluGlySer

Fig. 8

SEQ ID NO: 4

MetGluGluLeuAspGlyGluProThrValThrLeuIleProGlyValAsnSerLysLysAsnGlnMet
TyrPheAspTrpGlyProGlyGluMetLeuValCysGluThrSerPheAsnLysLysGluLysSerGlu
MetValProSerCysProPheIleTyrIleIleArgLysAspValAspValTyrSerGlnIleLeuArg
LysLeuPheAsnGluSerHisGlyIlePheLeuGlyLeuGlnArgIleAspGluGluLeuThrGlyLys
SerArgLysSerGlnLeuValArgValSerLysAsnTyrArgSerValIleArgAlaCysMetGluGlu
MetHisGlnValAlaIleAlaAlaLysAspProAlaAsnGlyArgGlnPheSerSerGlnValSerIle
LeuSerAlaMetGluLeuIleTrpAsnLeuCysGluIleLeuPheIleGluValAlaProAlaGlyPro
LeuLeuLeuHisLeuLeuAspTrpValArgLeuHisValCysGluValAspSerLeuSerAlaAspVal
LeuGlySerGluAsnProSerLysHisAspSerPheTrpAsnLeu*****ProGlyAsnThrGlnThrL
euThrGluLeuGluLeuLysTrpGlnHisTrpHisGluGluCysGluArgTyrLeuGlnAspSerThrP
heAlaThrSerProHisLeuGluSerLeuLeuLysIleMetLeuGlyAspGluAlaAlaLeuLeuGluG
lnLysGluLeuLeuSerAsnTrpTyrHisPheLeuValThrArgLeuLeuTyrSerAsnProThrValL
ysProIleAspLeuHisTyrTyrAlaGlnSerSerLeuAspLeuPheLeuGlyGlyGluSerSerProG
luProLeuAspAsnIleLeuLeuAlaAlaPheGluPheAspIleHisGlnValIleLysGluCysSerI
leAlaLeuSerAsnTrpTrpPheValAlaHisLeuThrAspLeuLeuAspHisCysLysLeuLeuGlnS
erHisAsnLeuTyrPheGlySerAsnMetArgGluPheLeuLeuLeuGluTyrAlaSerGlyLeuPheA
laHisProSerLeuTrpGlnLeuGlyValAspTyrPheAspTyrCysProGluLeuGlyArgValSerL
euGluLeuHisIleGluArgIleProLeuAsnThrGluGlnLysAlaLeuLysValLeuArgIleCysG
luGlnArgGlnMetThrGluGlnValArgSerIleCysLysIleLeuAlaMetLysAlaValArgAsnA
snArgLeuGlySerAlaLeuSerTrpSerIleArgAlaLysAspAlaAlaPheAlaThrLeuValSerA
spArgPheLeuArgAspTyrCysGluArgGlyCysPheSerAspLeuAspLeuIleAspAsnLeuGlyP
roAlaMetMetLeuSerAspArgLeuThrPheLeuGlyLysTyrArgGluPheHisArgMetTyrGlyG
luLysArgPheAlaAspAlaAlaSerLeuLeuLeuSerLeuMetThrSerArgIleAlaProArgSerP
heTrpMetThrLeuLeuThrAspAlaLeuProLeuLeuGluGlnLysGlnValIlePheSerAlaGluG
lnThrTyrGluLeuMetArgCysLeuGluAspLeuThrSerArgArgProValHisGlyGluSerAspT
hrGluGlnLeuGlnAspAspAspIleGluThrThrLysValGluMetLeuArgLeuSerLeuAlaArgA
snLeuAlaArgAlaIleIleArgGluGlySerLeuGluGlySer

Fig. 9

SEQ ID NO: 26

MetGluGluLeuAspGlyGluProThrValThrLeuIleProGlyValAsnSerLysLysAsnGlnMet
TyrPheAspTrpGlyProGlyGluMetLeuValCysGluThrSerPheAsnLysLysGluLysSerGlu
MetValProSerCysProPheIleTyrIleIleArgLysAspValAspValTyrSerGlnIleLeuArg
LysLeuPheAsnGluSerHisGlyIlePheLeuGlyLeuGlnArgIleAspGluGluLeuThrGlyLys
SerArgLysSerGlnLeuValArgValSerLysAsnTyrArgSerValIleArgAlaCysMetGluGlu
MetHisGlnValAlaIleAlaAlaLysAspProAlaAsnGlyArgGlnPheSerSerGlnValSerIle
LeuSerAlaMetGluLeuIleTrpAsnLeuCysGluIleLeuPheIleGluValAlaProAlaGlyPro
LeuLeuLeuHisLeuLeuAspTrpValArgLeuHisValCysGluValAspSerLeuSerAlaAspVal
LeuGlySerGluAsnProSerLysHisAspSerPheTrpAsnLeuValThrIleLeuValLeuGlnGly
ArgLeuAspGluAlaArgGlnMetLeuSerLysGluAlaAspAlaSerProAlaSerAlaGlyIleCys
ArgIleMetGlyAspLeuMetArgThrMetProIleLeuSerProGlyAsnThrGlnThrLeuThrGlu
LeuGluLeuLysTrpGlnHisTrpHisGluGluCysGluArgTyrLeuGlnAspSerThrPheAlaThr
SerProHisLeuGluSerLeuLeuLysIleMetLeuGlyAspGluAlaAlaLeuLeuGluGlnLysGlu
LeuLeuSerAsnTrpTyrHisPheLeuValThrArgLeuLeuTyrSerAsnProThrValLysProIle
AspLeuHisTyrTyrAlaGlnSerSerLeuAspLeuPheLeuGlyGlyGluSerSerProGluProLeu
AspAsnIleLeuLeuAlaAlaPheGluPheAspIleHisGlnValIleLysGluCysSerIleAlaLeu
SerAsnTrpTrpPheValAlaHisLeuThrAspLeuLeuAspHisCysLysLeuLeuGlnSerHisAsn
LeuTyrPheGlySerAsnMetArgGluPheLeuLeuLeuGluTyrAlaSerGlyLeuPheAlaHisPro
SerLeuTrpGlnLeuGlyValAspTyrPheAspTyrCysProGluLeuGlyArgValSerLeuGluLeu
HisIleGluArgIleProLeuAsnThrGluGlnLysAlaLeuLysValLeuArgIleCysGluGlnArg
GlnMetThrGluGlnValArgSerIleCysLysIleLeuAlaMetLysAlaValArgAsnAsnArgLeu
GlySerAlaLeuSerTrpSerIleArgAlaLysAspAlaAlaPheAlaThrLeuValSerAspArgPhe
LeuArgAspTyrCysGluArgGlyCysPheSerAspLeuAspLeuIleAspAsnLeuGlyProAlaMet
MetLeuSerAspArgLeuThrPheLeuGlyLysTyrArgGluPheHisArgMetTyrGlyGluLysArg
PheAlaAspAlaAlaSerLeuLeuLeuSerLeuMetThrSerArgIleAlaProArgSerPheTrpMet
ThrLeuLeuThrAspAlaLeuProLeuLeuGluGlnLysGlnValLysValAlaAlaAlaValValPhe
PheAlaCysGlnSerLeuLeuGluLeuSerCysIleAlaValAlaAspValArgValSerSerPheVal
ValLeuProValArgValTyrSerPro

Fig. 10

SEQ ID NO: 28

MetGluGluLeuAspGlyGluProThrValThrLeuIleProGlyValAsnSerLysLysAsnGlnMet
TyrPheAspTrpGlyProGlyGluMetLeuValCysGluThrSerPheAsnLysLysGluLysSerGlu
MetValProSerCysProPheIleTyrIleIleArgLysAspValAspValTyrSerGlnIleLeuArg
LysLeuPheAsnGluSerHisGlyIlePheLeuGlyLeuGlnArgIleAspGluGluLeuThrGlyLys
SerArgLysSerGlnLeuValArgValSerLysAsnTyrArgSerValIleArgAlaCysMetGluGlu
MetHisGlnValAlaIleAlaAlaLysAspProAlaAsnGlyArgGlnPheSerSerGln\*\*\*\*\*ValT
hrIleLeuValLeuGlnGlyArgLeuAspGluAlaArgGlnMetLeuSerLysGluAlaAspAlaSerP
roAlaSerAlaGlyIleCysArgIleMetGlyAspLeuMetArgThrMetProIleLeuSerProGlyA
snThrGlnThrLeuThrGluLeuGluLeuLysTrpGlnHisTrpHisGluGluCysGluArgTyrLeuG
lnAspSerThrPheAlaThrSerProHisLeuGluSerLeuLeuLysIleMetLeuGlyAspGluAlaA
laLeuLeuGluGlnLysGluLeuLeuSerAsnTrpTyrHisPheLeuValThrArgLeuLeuTyrSerA
snProThrValLysProIleAspLeuHisTyrTyrAlaGlnSerSerLeuAspLeuPheLeuGlyGlyG
luSerSerProGluProLeuAspAsnIleLeuLeuAlaAlaPheGluPheAspIleHisGlnValIleL
ysGluCysSerIleAlaLeuSerAsnTrpTrpPheValAlaHisLeuThrAspLeuLeuAspHisCysL
ysLeuLeuGlnSerHisAsnLeuTyrPheGlySerAsnMetArgGluPheLeuLeuLeuGluTyrAlaS
erGlyLeuPheAlaHisProSerLeuTrpGlnLeuGlyValAspTyrPheAspTyrCysProGluLeuG
lyArgValSerLeuGluLeuHisIleGluArgIleProLeuAsnThrGluGlnLysAlaLeuLysValL
euArgIleCysGluGlnArgGlnMetThrGluGlnValArgSerIleCysLysIleLeuAlaMetLysA
laValArgAsnAsnArgLeuGlySerAlaLeuSerTrpSerIleArgAlaLysAspAlaAlaPheAlaT
hrLeuValSerAspArgPheLeuArgAspTyrCysGluArgGlyCysPheSerAspLeuAspLeuIleA
spAsnLeuGlyProAlaMetMetLeuSerAspArgLeuThrPheLeuGlyLysTyrArgGluPheHisA
rgMetTyrGlyGluLysArgPheAlaAspAlaAlaSerLeuLeuLeuSerLeuMetThrSerArgIleA
laProArgSerPheTrpMetThrLeuLeuThrAspAlaLeuProLeuLeuGluGlnLysGlnValLysV
alAlaAlaAlaValValPhePheAlaCysGlnSerLeuLeuGluLeuSerCysIleAlaValAlaAspV
alArgValSerSerPheValValLeuProValArgValTyrSerPro

Fig. 11

SEQ ID NO: 34

MetGluGluLeuAspGlyGluProThrValThrLeuIleProGlyValAsnSerLysLysAsnGlnMet
TyrPheAspTrpGlyProGlyGluMetLeuValCysGluThrSerPheAsnLysLysGluLysSerGlu
MetValProSerCysProPheIleTyrIleIleArgLysAspValAspValTyrSerGlnIleLeuArg
LysLeuPheAsnGluSerHisGlyIlePheLeuGlyLeuGlnArgIleAspGluGluLeuThrGlyLys
SerArgLysSerGlnLeuValArgValSerLysAsnTyrArgSerValIleArgAlaCysMetGluGlu
MetHisGlnValAlaIleAlaAlaLysAspProAlaAsnGlyArgGlnPheSerSerGlnValSerIle
LeuSerAlaMetGluLeuIleTrpAsnLeuCysGluIleLeuPheIleGluValAlaProAlaGlyPro
LeuLeuLeuHisLeuLeuAspTrpValArgLeuHisValCysGluValAspSerLeuSerAlaAspVal
LeuGlySerGluAsnProSerLysHisAspSerPheTrpAsnLeuValThrIleLeuValLeuGlnGly
ArgLeuAspGluAlaArgGlnMetLeuSerLysGluAlaAspAlaSerProAlaSerAlaGlyIleCys
ArgIleMetGlyAspLeuMetArgThrMetProIleLeuSerProGlyAsnThrGlnThrLeuThrGlu
LeuGluLeuLysTrpGlnHisTrpHisGluGluCysGluArgTyrLeuGlnAspSerThrPheAlaThr
SerProHisLeuGluSerLeuLeuLysIleMetLeuGlyAspGluAlaAlaLeuLeuGluGlnLysGlu
LeuLeuSerAsnTrpTyrHisPheLeuValThrArgLeuLeuTyrSerAsnProThrValLysProIle
AspLeuHisTyrTyrAlaGlnSerSerLeuAspLeuPheLeuGlyGlyGluSerSerProGluProLeu
AspAsnIleLeuLeuAlaAlaPheGluPheAspIleHisGlnValIleLysGluCysSerIleAlaLeu
SerAsnTrpTrpPheValAlaHisLeuThrAspLeuLeuAspHisCysLysLeuLeuGlnSerHisAsn
LeuTyrPheGlySerAsnMetArgGluPheLeuLeuLeuGluTyrAlaSerGlyLeuPheAlaHisPro
SerLeuTrpGlnLeuGlyValAspTyrPheAspTyrCysProGluLeuGlyArgValSerLeuGluLeu
HisIleGluArgIleProLeuAsnThrGluGlnLysAlaLeuLysValLeuArgIleCysGluGlnArg
GlnMetThrGluGlnValArgSerIleCysLysIleLeuAlaMetLysAlaValArgAsnAsnArgLeu
GlySerAlaLeuSerTrpSerIleArgAlaLysAspAlaAlaPheAlaThrLeuValSerAspArg***
**TrpValProLeuValLeuAlaSerGlnGlyLeuGlyGly (a)

(b)

Fig. 17
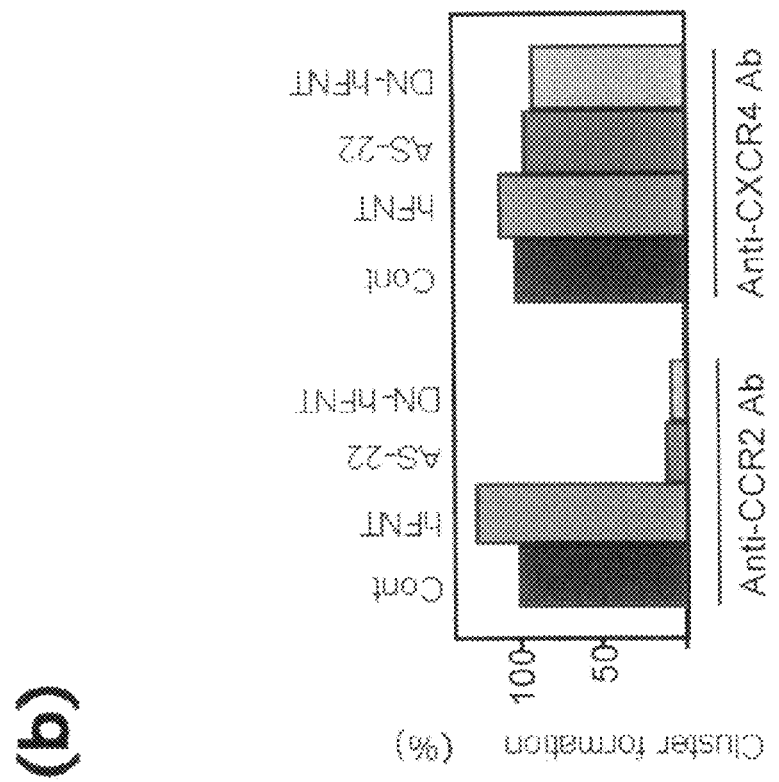
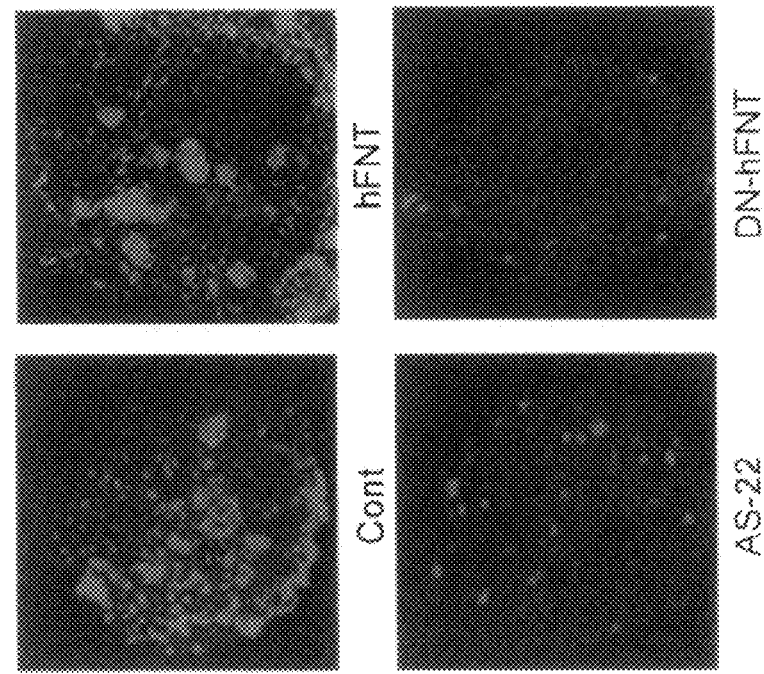

Fig. 20
(a)
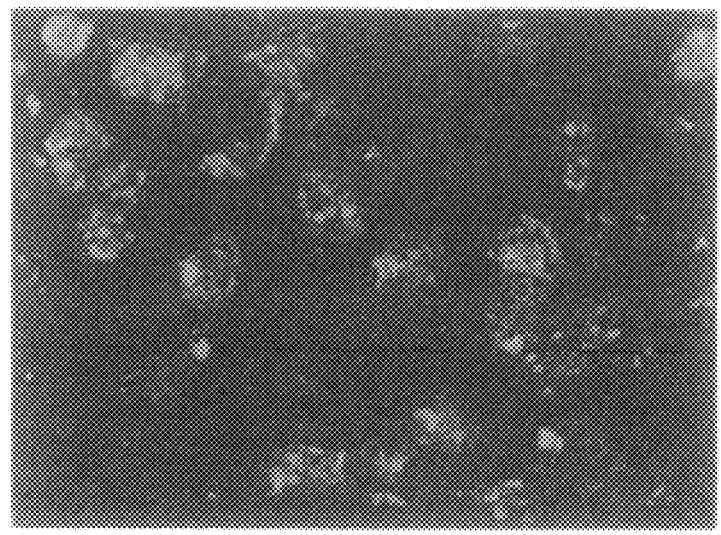
(b)
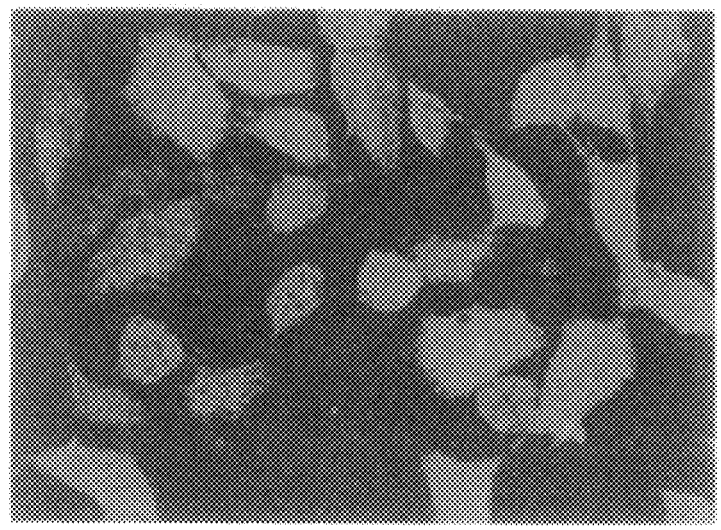

MOLECULE ASSOCIATING WITH INTRACELLULAR C-TERMINAL DOMAIN OF RECEPTOR

This application is a divisional application of co-pending application Ser. No. 10/504,879 filed on Aug. 17, 2004 and for which priority is claimed under 35 U.S.C. §120, which is a National Stage of PCT International Application No. PCT/JP03/01699 filed on Feb. 18, 2003, under 35 U.S.C. §371, which claims priority of JP 2002-42262 filed in Japan on Feb. 19, 2002, the entire contents of which are hereby incorporated by reference.

TECHNICAL FIELD

This invention relates to a protein, which associates with the intracellular C-terminal domain of a G protein-coupled receptor for chemokine, a DNA encoding the same, and utilization thereof. More specifically, it relates to a novel protein which associates with the intracellular C-terminal domain of receptors CCR2 and CCR5 to thereby control the functions of the receptors CCR2 and CCR5, a DNA encoding the same and utilization thereof in the field of medicine.

BACKGROUND ART

In cells, external stimulation with a ligand is transmitted into cells via a receptor. In the case of chemokine receptors, for example, it is known that leukocyte chemotaxis, which is the fundamental function in inflammation and immune responses, is strictly controlled by attractors serving as agonists (Documents 1 to 4). More specifically speaking, a chemokine prototype CCL2 (also known as MCAF and MCP-1) was found as a macrophage attractant mediated by a receptor CCR2 (Documents 5 to 8). Moreover, chemokines CCL3, 4 and 5 are known as agonists for CCR5.

It has been considered that intracellular signal transduction of a receptor depends on the G protein switching mechanism. Concerning chemokines, there have been identified more than 50 types of chemokines and 20 types of G protein-coupled receptors (GPCRs) as the chemokine-chemokine receptor family. Each chemokine receptor has a strict chemokine-specificity and shows an expression pattern restricted to leukocyte subtype (Documents 9 to 11).

Now, the relationships between the intracellular signal transduction of receptors and diseases will be discussed. In the case of the chemokine receptor CCR2, for example, the receptor CCR2 is a 7-transmembrane G protein-coupled receptor known as occurring in monocytes, macrophages, lymphocytes, endothelial cells, smooth muscular cells and so on and its agonist CCL2 acts as an attractant via interaction with the receptor CCR2 (Document 12). It is considered that the CCL2-CCR2 pathway participates in the causes of atherosclerosis (Documents 13 and 14), chronic glomerulonephritis (Document 15), multiple sclerosis (Documents 16 and 17) and other chronic inflammatory diseases (Documents 18 to 21). On the other hand, it is reported that CCR5, which is known as a chemokine CCL2 (MIP-1α), CCL4 (MIP-1β) or CCL5 (RANTES) receptor, is expressed in monocytes and macrophages and participates in various inflammatory diseases similar to CCR2. Furthermore, it is known that CCR2 and CCR5 serve as coreceptors for cell entry of human immunodeficiency virus (HIV) (Deng et al., Nature, 381, 661-666 (1996)). However, a large number of points still remain unknown in intracellular signal transduction cascades relating to leukocyte chemotaxis. Accordingly, there is a great worth in studying the mechanism controlling chemokine receptor-mediated leukocyte chemotaxis.

It is considered that a receptor having an attractant bonded thereto activates a G protein and thus causes the dissociation of the G protein into α- and β-subunits and the formation of a second messenger, thereby initiating actin polymerization and leukocyte chemotaxis (Documents 22 and 23). The dissociation of the G protein is followed by the phosphorylation of the receptor by protein kinases such as PKs, Jaks and GRKs (Documents 24 and 25). Subsequently, the phosphorylation in the intracellular domain in the carboxyl terminal region (C-terminal region) of the receptor promotes receptor internalization with adaptors Aps and arrestin and inhibits excessive responses (Document 26). As the results of conventional studies, there have been known GPCR-binding molecules regulating receptors' functions such as cell-surface transportation and intracellular uptake (Documents 33 and 34). However, there have been known so far few GPCR-binding molecules controlling intracellular chemotactic signal cascades specific to individual receptors.

Studies on mutations have clarified that receptors binding to attractants such as cAMP, fMLP and chemokines activate chemotactic signal cascades even in the case where phosphorylation does not occur in the intracellular C-terminal domain (Documents 27 to 32). In the previous studies, GPCR-binding molecules, which regulate receptors' functions such as cell-surface transportation and intracellular uptake, were identified (Documents 33 and 34). However, chemotactic signal cascades of individual receptors are scarcely known.

It is reported that the second cytoplasmic loop and the C-terminal domain of a GPCR are important sites in the activation of the chemotactic signal cascade by the binding to a G protein and activation thereof (Documents 27, 28, 35 and 36). When 12 residues in the intracellular C-terminal domain of CCR2 (a sequence in the Pro-12-C terminal domain; SVF-FRKHITKRF (SEQ ID NO:41)) is removed, for example, its chemotactic response disappears though the G protein-binding ability to CCL2 remains unchanged (Documents 28 and 37). When a shorter sequence from the terminus is removed, however, no effect is observed. It is interesting that the DRY motif at the second cytoplasmic loop of a chemokine receptor is completely conserved while the sequence in the neighborhood of the terminus is scarcely conserved. Although chemokine receptors CCR2 and CXCR4 both activate monocyte chemotaxis cascades, the Pro-12-C terminal domain of CCR2 never relates to the conservation of a similar domain of CXCR4.

DISCLOSURE OF THE INVENTION

Based on a series of facts as discussed above, the present inventors drawn a novel hypothesis concerning the intracellular signal transduction mechanism that, even in the case where phosphorylation does not occur in the intracellular C-terminal domain of a receptor, an unknown molecule associates with the Pro-C terminal domain of a G protein-coupled receptor for each chemokine and thus controls leukocyte chemotaxis depending on the receptor. To examine this hypothesis and clarify therapeutic targets in inflammatory diseases as well as other various diseases, they attempted to search for a CCR2-binding protein as an aspect of the invention. As a result, they found out a novel cytoplasmic protein associating directly and specifically with the Pro-12-C-terminal domain of CCR2 and clarified that that this protein forms clusters with CCR2 after stimulation with CCL2. Thus, it was confirmed that there is a novel signal transduction system in the G protein relating signal transduction in the CCL2-CCR2 pathway. It was also found out that this novel protein associates with the intracellular C-terminal domain of a receptor CCR5 too.

Based on the above-described findings, the present inventors attempted to compare and discuss the conservation states of corresponding genetic information in biological systems and clarify the mechanisms of intracellular signal transduction and regulation concerning cell migration, thereby developing a novel route for the establishment of technical means contributing to the treatment and diagnosis of diseases in which the CCL2-CCR2 pathway and the CCL3, 4 or 5-CCR5 pathway participate.

Accordingly, the present invention relates to the following DNAs.

(1) A DNA encoding the amino acid sequence of a polypeptide (a FROUNT protein) having an amino acid sequence represented by any of SEQ ID NOS:1 to 18.

(2) A DNA encoding a FROUNT protein represented by any of SEQ ID NOS:19 to 36.

(3) A DNA of the sequence having at least 90% identity to the DNA as described in the above (1) or (2) and encoding a polypeptide having a function of the FROUNT protein.

The present invention further relates to the following protein or polypeptide.

(4) A FROUNT protein having an amino acid sequence represented by any of SEQ ID NOS:1 to 18.

(5) A polypeptide having an amino acid sequence having at least 90% identity to the amino acid sequence as described in the above (4) and having the function of the FROUNT protein.

The present invention further relates to the following antisenses or ribozyme.

(6) An antisense DNA or an antisense RNA inhibiting the expression of a FROUNT protein having an amino acid sequence represented by any of SEQ ID NOS:1 to 18.

(7) An antisense DNA or an antisense RNA directed against the full length or a part of the DNA as described in any of the above (1) to (3).

(8) An antisense RNA having the full length or a part of the sequence represented by SEQ ID NO:39.

(9) An antisense RNA having at least 90% identity to the sequence of the RNA as described in the above (8) and inhibiting the expression of a FROUNT protein.

(10) A DNA for producing the RNA as described in the above (8) or (9) which consists of the DNA sequence represented by SEQ ID NO:40 or the full length or a part of a sequence having at least 90% identity to this sequence.

(11) A ribozyme against an RNA corresponding to a DNA encoding the amino acid sequence represented by SEQ ID NO:1 or the DNA sequence represented by SEQ ID NO:19.

The present invention further relates to the following plasmids or liposome preparations.

(12) A plasmid containing the DNA as described in any of the above (1) to (3).

(13) A liposome preparation containing the DNA as described in any of the above (1) to (3).

(14) A plasmid containing the DNA as described in the above (7) or (10).

(15) A liposome preparation containing the DNA or RNA as described in any of the above (7) to (10).

(16) A liposome preparation containing the ribozyme as described in the above (11).

(17) An isolated antibody binding specifically to the polypeptide as described in the above (4) or (5).

The present invention further relates to the following pharmaceutical compositions and treating compositions.

(18) A composition for treating chronic inflammatory disease or autoimmune diseases or for treating or preventing infectious diseases which contains as the active ingredient the plasmid or the liposome preparation as described in any of the above (14) to (16).

(19) A composition for treating atherosclerosis, chronic glomerulonephritis or multiple sclerosis, an immunomodulator or an antiallergic agent which contains as the active ingredient the plasmid or the liposome preparation as described in any of the above (14) to (16).

(20) A pharmaceutical composition which contains as the active ingredient the DNA as described in any of the above (1) to (3).

(21) An immunoenhancer, a self-defensive reaction promoter or a composition for treating infectious diseases which contains as the active ingredient the DNA as described in any of the above (1) to (3).

(22) An immunoenhancer, a self-defensive reaction promoter or a composition for treating infectious diseases which contains as the active ingredient the plasmid or the liposome preparation as described in the above (12) or (13).

The present invention further relates to the following examination method and probe to be used therein.

(23) A method of examining the presence or absence of an abnormality in the CCL2-CCR2 pathway or the CCL3, 4 or 5-CCR5 pathway characterized by comprising comparing the full length or a part of the DNA sequence as described in any of the above (1) to (3) with a DNA sequence collected from a specimen and thus judging whether or not the DNA collected from the specimen has an abnormality.

(24) A probe for examining the presence or absence of an abnormality in the CCL2-CCR2 pathway or the CCL3, 4 or 5-CCR5 pathway which consists of the full length or apart of a sequence complementary to the DNA as described in any of the above (1) to (3).

The present invention further relates to the following methods of identifying an inhibitor and substances to be used therein.

(25) A method of identifying an agonist inhibitor characterized by comprising preparing a cell in which a receptor undergoing clusterization by stimulation with an agonist and a marker-labeled molecule coupling or associating with the intracellular terminus of the receptor are forcibly expressed, treating the cell with a specimen containing the agonist and a candidate for the agonist inhibitor, observing whether or not the clusterization of the marker is induced in the cell, and thus judging whether or not the candidate has an inhibitory effect on the agonist.

(26) A method of identifying an inhibitor of an agonist to receptor(s) CCR2 and/or CCR5 characterized by comprising forcibly expressing a marker-labeled FROUNT protein in a cell having the receptor(s) CCR2 and/or CCR5 or expressing the same, treating the cell with an agonist to CCR2 and/or CCR5 and a candidate for the agonist inhibitor, observing whether or not the clusterization of the receptor(s) is induced, and thus judging whether or not the candidate has an inhibitory effect on the agonist.

(27) A method of identifying an agonist inhibitor by using a chimeric receptor cell characterized by comprising preparing a cell having a labeled FROUNT protein and a chimeric receptor by forcibly expressing a chimeric receptor, which is obtained by integrating a DNA sequence encoding the full length or a part of a FROUNT protein-association sequence in the intracellular C-terminal domain of receptor(s) CCR2 and/or CCR5 into the intracellular C-terminal domain of the DNA sequence of a desired receptor, in a cell appropriate for the desired receptor and then forcibly expressing a marker-labeled FROUNT protein in the cell, treating the chimeric receptor cell with an agonist to the receptor and a candidate for an agonist inhibitor, then observing whether or not the clusterization of the receptor is induced and thus judging whether or not the candidate has an inhibitory effect on the agonist.

(28) The identification method as described in the above (27) characterized in that the FROUNT protein-association sequence in the intracellular C-terminal domain of receptor(s) CCR2 and/or CCR5 is the amino acid sequence represented by SEQ ID NO:41.

(29) The identification method as described in the above (26) or (27) characterized in that the marker-labeled FROUNT protein is a FROUNT protein fused with a visible color fluorescent protein.

(30) The identification method as described in the above (29) wherein the visible color fluorescent protein is a green fluorescent protein, a red fluorescent protein, a blue fluorescent protein or a yellow fluorescent protein.

(31) A DNA encoding the FROUNT protein fused with a visible color fluorescent protein as described in the above (29) or (30).

(32) A plasmid containing the DNA sequence as described in the above (31).

(33) A chimeric receptor DNA obtained by integrating a DNA sequence encoding the full length or a part of a FROUNT protein-association sequence in the intracellular C-terminal domain of receptor CCR2 into the intracellular C-terminal domain of the DNA sequence of a desired receptor.

(34) The chimeric receptor as described in the above (32) characterized in that the FROUNT protein-association sequence in the intracellular C-terminal domain of receptor(s) CCR2 and/or CCR5 is the amino acid sequence represented by SEQ ID NO:41.

(35) A cell wherein a receptor undergoing clusterization by stimulation with an agonist and a marker-labeled molecule coupling or associating with an intracellular terminus of the receptor are forcibly expressed.

(36) A cell wherein a marker-labeled FROUNT protein is forcibly expressed and receptor(s) CCR2 and/or CCR5 are further expressed therein.

(37) A cell having a labeled FROUNT protein and a chimeric receptor prepared by forcibly expressing a chimeric receptor, which is obtained by integrating a DNA sequence encoding the full length or a part of a FROUNT protein-association sequence in the intracellular C-terminal domain of receptor(s) CCR2 and/or CCR5 into the intracellular C-terminal domain of the DNA sequence of a desired receptor, in a cell appropriate for the desired receptor and then forcibly expressing a marker-labeled FROUNT protein in the cell.

(38) The cell as described in the above (36) or (37) characterized in that the FROUNT protein-association sequence in the intracellular C-terminal domain of receptor(s) CCR2 and/or CCR5 is the amino acid sequence represented by SEQ ID NO:41.

(39) The cell as described in the above (36) or (37) characterized in that the marker-labeled FROUNT protein is a FROUNT protein fused with a visible color fluorescent protein.

(40) The cell as described in the above (39) wherein the visible color fluorescent protein is a green fluorescent protein, a red fluorescent protein, a blue fluorescent protein or a yellow fluorescent protein.

(41) A method of identifying an intracellular signal transduction pathway inhibitor depending on binding of a FROUNT protein to a receptor which comprises using the binding activity of the FROUNT protein to the receptor as an indication and screening a substance inhibiting the binding activity.

(42) The method of identifying an inhibitor as described in the above (25), (26) or (27) characterized in that the identification is made depending on a color change as an indication by using a cell wherein both of the receptor and the protein associating with the C-terminal domain of the receptor are labeled with visible color markers being different from each other in color.

(43) A cell wherein both of a receptor and a protein associating with the C-terminal domain of the receptor, which are labeled with visible color markers being different from each other in color, are expressed therein.

(44) A method of judging whether or not a specimen contains a cytotoxic substance which comprises treating the cell as described in the above (35) to (40) or (43) with the specimen, then treating it with an agonist to the receptor carried by the cell and observing whether or not clusterization or colocalization is induced.

BRIEF DESCRIPTION OF THE DRAWINGS

FIG. 1 shows the results of a test for confirming an interaction between the FROUNT protein obtained from the clone 19 and the receptor CCR2 using Y190 cells.

FIG. 2 shows the results of a test for confirming an interaction between the FROUNT protein obtained from the clone 19 and the receptor CCR2 using the coimmunoprecipitation method.

FIG. 3 shows the relationship between the intracellular C-terminal domain sequence of CCR2 and the action of FROUNT protein 1.

FIG. 4 shows the amino acid sequence structure of human FROUNT protein 1 (SEQ ID NO:2).

FIG. 5(a) shows the Kyte-Doolittle hydropathy plot of FROUNT protein 1. FIG. 5(b) shows the structural analysis of human FROUNT protein 1 through database motif searching and a comparison among organisms. FIG. 5(c) is a schematic model showing human FROUNT protein domains.

FIG. 6 presents fluorescent microphotographs of control eGFP (upper) and FROUNT fused with a fluorescent protein (lower). FIGS. 6(a) and 6(b) respectively show micrographs before and after treating with CCR2 antibody.

FIG. 7 shows the structure of clone 1 (656 amino acids (a.a.)) (SEQ ID NO:2).

FIG. 8 shows the structure of clone 2 (611 a.a.) (SEQ ID NO:4).

FIG. 9 shows the structure of clone 13 (630 a.a.) (SEQ ID NO:26).

FIG. 10 shows the structure of clone 14 (566 a.a.) (SEQ ID NO:28).

FIG. 11 shows the structure of clone 17 (518 a.a.) (SEQ ID NO:34).

FIG. 17 shows the results of the detection of the ability of clusterization. FIG. 17(a) presents images of stimulation of each cells with CCR2-specific antibody, while FIG. 17(b) shows the results of the confocal microscopic quantification of the clusterization ability of each receptor stimulated with the CCR2- or CXCL2-specific antibody (the longitudinal axis referring to control %).

FIG. 20 shows inhibition of chemokine receptor clusterization by MCP-1-specific antibody. FIG. 20(a) indicates a control case, while FIG. 20(b) shows the inhibition results.

BEST MODE FOR CARRYING OUT THE INVENTION

Figure 12:
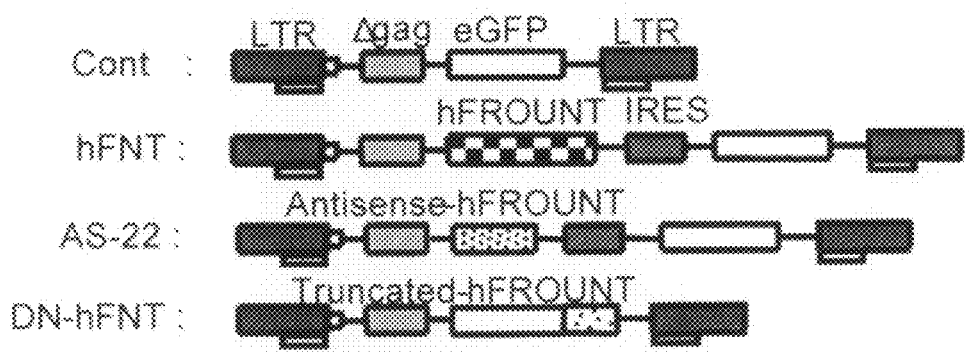
FIG. 12 shows the structure of a human FROUNT vector.

The present invention provides an intracellular signal transduction-regulating polypeptide associating with the intracellular C-terminal domain of a receptor CCR2, which is one of G protein-coupled receptors for chemokines, and a DNA encoding the same. Further, it provides an antibody, an antisense sequence inhibiting the expression of the DNA encoding the above-described protein and a probe consisting of a sequence complementary to the above-described DNA. Furthermore, it provides a method of identifying a substance which inhibits the association of the above-described protein with the intracellular C-terminal domain of the receptor by using the protein.

(1) Discovery of Novel Protein

The present inventors have confirmed for the first time the presence of intracellular signal transduction-regulating polypeptide associating with the intracellular C-terminal domain of a receptor CCR2, which is one of G protein-coupled receptors for chemokines, and the DNA encoding the same, i.e., discovery of a novel intracellular signal transduction mechanism. This protein can be obtained by searching for a molecule specifically binding to an intracellular domain following the 7-transmembrane part of the receptor with the use of the two-hybrid method, thus obtaining its partial sequence, constructing oligoprimers based on this sequence, and then cloning the full-length cDNA by using the RACE method.

More specifically speaking, a cytoplasmic protein directly associating with the intracellular C-terminal domain sequence of the receptor CCR2 (the sequence occurring in the 309- to 360-residues) carried by human myelomonocytic leukemia can be obtained. Among several clones thus obtained, one contains a cDNA (clone 19 represented by SEQ ID NO: 38) encoding a novel polypeptide having a sequence consisting of 156 amino acids (SEQ ID NO:37). Based on this sequence, oligoprimers are constructed and a full-length cDNA (clone 1, SEQ ID NO:19) is cloned by the RACE method. The full-length cDNA (clone 1) thus obtained is amplified by the PCR method and then inserted into a plasmid vector pcDNA3 (manufactured by Invitorgen) to thereby construct an expression vector. Next, this expression vector is transferred into HEK293 cells (ATCC/CRL-157) to give a transformant. Expression of FROUNT protein 1 (SEQ ID NO:1) is detected by using the Western blotting method.

(2) Structural Characteristics of the Protein

The thus obtained protein having the amino acid sequence represented by SEQ ID NO:1 and associating with the intracellular C-terminal domain of the receptor CCR2 (the protein originating in clone 1 which will be also called FROUNT protein 1 hereinafter) has a sequence consisting of 656 amino acids and its molecular weight is 79 KDa. Its structural characteristics reside in containing a leucine zipper structure known as playing an important role in the association between proteins, 4 tyrosine-based motives and 4 dileucine motives. FIG. 5(a) shows the Kyte-Doolittle hydropathy plot of this protein. When examined by homology searching, it is clarified that none of known human genes or proteins has a sequence similar to the above-described protein.

(3) Biological Properties

The biological properties of the obtained FROUNT protein 1 confirmed by the present inventors are as follows.

(1) When observed under a fluoromicroscope, FROUNT protein 1 binds specifically to a chemokine receptor CCR2 or CCR5 expressed in HEK cells in response to stimulation with the chemokine CCL2 and induces the clusterization of the receptor. It is found out that the chemokine receptors CCR2 and CXCR4 activate chemotactic signal cascades in THP-1 cells and human monocytes while FROUNT protein 1 associates with the intracellular C-terminal domain (SEQ ID NO:41) of the receptor CCR2 but not with that of CXCR4 (FIG. 1). The interaction between FROUNT protein 1 and the receptor CCR2 is confirmed by the binding in vitro and a coimmunoprecipitation assay with the use of Myc-tagged and HA-tagged recombinant FROUNT protein 1 (FIG. 2). Although the above-described 12-Pro-C-terminal domain is important in chemotaxis, it is reported that a mutant derived from the sequence by substitution of serine at the 317-position and threonine at the 325-position each by alanine (mutant with 12 residues) is inactive (Document 28). The relationship between FROUNT protein 1 and this mutant consisting of the 12 residues is examined. The association activity of FROUNT protein 1 completely disappears in the case of removing these 12 residues form the receptor CCR2 but the association activity is conserved in the case of removing a shorter sequence in the C-terminal side of the 12 residue. FROUNT protein binds to the above-described mutant with the 12 residues. These facts seemingly indicate that FROUNT protein 1 would associate with some partial sequence in the sequence of the intracellular C-terminal domain (SEQ ID NO:41) of the receptor CCR2 and exerts a function as a regulator participating in the receptor CCR2-dependent chemotaxis.

(2) When transfected cells with lessened expression of FROUNT protein 1 therein are established in a cultured cell system with the use of the antisense method, various intracellular signal transduction pathways (cell migration, calcium mobilization, receptor clusterization and receptor internalization) are lowered. In the case where FROUNT protein 1 is coexpressed in the above-described cell system, however, no lowering is observed. In the antisense cell system, cell migration activity of CCR5 due to stimulation with a ligand RANTES is lowered. Since these phenomena are not observed in vector control cells or in the case of stimulating with another chemokine SDF-1, it is confirmed that FROUNT protein 1 is a molecule which specifically controls CCR2 and CCR5. When the interaction between FROUNT protein 1 and the intracellular C-terminal domain of these receptors is blocked, therefore, responses of the receptor to external stimulation are lost.

(3) Moreover, a mouse with decreased FROUNT protein 1 in bone marrow-origin leukocytes is established and thioglycolate-induced macrophage infiltration ability of this mouse is evaluated. As a result, it is observed that this mouse shows lowered macrophage infiltration ability compared with a control mouse. This fact suggests that the phenomena clarified in the cultured cells reflect these phenomena at the individual mouse level under physiological conditions. As these results show, it is clarified through the examinations both in vitro and in vivo that the protein obtained by the present invention is a molecule which plays an important role in the CCR2- and CCR5-mediated monocyte and macrophage migration.

(4) Other Characteristics

As the results of database (Blast) homology searching, it is revealed that there are sequences highly homologous with the DNA sequence encoding FROUNT protein 1 in mouse and *Drosophila melanogaster* (AAF577B5) as well as in *Caenorhabditis elegans* (T24318) and yeast having no leukocyte (FIG. 5(b)). This fact that the DNA sequence encoding FROUNT protein 1 is conserved even in primitive organisms suggests that this protein would participate in fundamental life phenomena in various organisms over a broad range.

(5) Meanings of the Novel Protein

As the detailed acquisition process and biological properties as described above clearly indicate, it is considered that FROUNT protein 1 associates with the intracellular C-terminal domains of the chemokine G protein-coupled receptors CCR2 and CCR5 and thus participates in the mechanism of controlling the G protein switching system. That is to say, it seems that FROUNT protein 1 is a polypeptide which regulates the intracellular signal transduction, acts on the intracellular C-terminal domain of a receptor together with G protein and thus participates in the mechanism of controlling the function of the receptor. Since there has been known neither a chemotactic signal transduction mechanism specific to an individual chemokine receptor nor a protein capable of controlling the mechanism, it can be concluded that the presence such a protein per se has been clarified for the first time by the present inventors.

Based on the fact that the DNA sequence of FROUNT protein 1 is conserved even in the nematode and yeast having no leukocyte, there is a high possibility that FROUNT protein 1 and FROUNT-like proteins associating with the intracellular C-terminal domains of cell membrane receptors CCR2 and CCR5 to chemokines would control signal transduction systems from individual receptors not only in other leukocyte chemotactic factors but also in hormones and cell membrane receptors such as neurotransmitter molecules.

(6) Protein According to the Present Invention and DNA Encoding the Same

Thus, the protein according to the present invention and the DNA encoding the same are primarily an intracellular signal transduction-regulating polypeptide associating with the intracellular C-terminal domain of a G protein-coupled receptor CCR2 for chemokine CCL2 and a DNA encoding the same, and an intracellular signal transduction-regulating polypeptide associating with the intracellular C-terminal domain of a G protein-coupled receptor CCR5 for chemokines CCL's 3, 4 and 5, and a DNA encoding the same. More specifically speaking, the protein according to the present invention and the DNA encoding the same are a polypeptide having the amino acid sequence represented by SEQ ID NO:1 and a DNA encoding the same. Still specifically speaking, the DNA has the sequence represented by SEQ ID NO:20.

(7) Clones Other than Clone Land Peptides Corresponding Thereto

In screening a THP-1-origin cDNA library by the plaque hybrid method, a clone (clone 1) of FROUNT protein 1 and another clone 2 (SEQ ID NO:20) are obtained. By examining amino acid sequences deduced based on the base sequences thereof, it is clarified that human FROUNT involves at least two molecular types, i.e., a sequence consisting of 656 amino acid residues (α-type, clone 1) and another one consisting of 630 amino acid residues (β-type, clone 13) differing from each other exclusively in the C-terminal part. Further, cloning is carried out by the PCR method and thus at least 18 splicing mutants of the α- and β-types represented by SEQ ID NOS:1 to 18 are identified. Each of these clones 1 to 18 has an N-terminus starting with ATG and a C-terminus stopping with a termination codon (TAG, TGA, TAA). It is anticipated that these clones respectively have the amino acid sequences represented by SEQ ID NOS:1 to 18. Polypeptides corresponding to these clones 2 to 18 will be referred to as FROUNT proteins 2 to 18 hereinafter. The clones 2 to 18 are in common to the clone 1 at least in the N-terminal sequence and, moreover, have common sequences in other parts. Based on these facts, it is considered that the clones 2 to 18 have functions either entirely or partly common to clone 1. It is also considered that clones 2 to 18 are usable as probes for detecting FROUNT proteins 1 to 18. Furthermore, these polypeptides are usable as antigens for constructing antibodies and so on.

(8) Gene Structures of FROUNT Proteins 1 to 18

As the results of human genome database (NCBI, Blast) searching, it is identified that the FROUNT gene clone 1 is encoded as 19 exons in the 17th chromosome (in the neighborhood of D17S785 and D17S1352) similar to CCL's 2, 3 and 5. In the FROUNT gene clone 13 (a β-type splicing mutant), the exons 1 to 16 are the same as those in the FROUNT gene clone 1 but the reading frame in the 17th exon is extended backward compared with the FROUNT gene clone 1. It is thus confirmed that the FROUNT gene clone 13 is encoded as 17 exons and the FROUNT gene clone 13 differs from the FROUNT gene clone 1 exclusively in the C-terminal structure.

(9) Functions of FROUNT Proteins

As discussed above, it is clearly understood that FROUNT proteins 1 to 18 originate in the same genomic DNA (gDNA) and have one of the following functions.

1. By associating with the intracellular C-terminal domain of the receptor CCR2 and thus regulating the intracellular signal transduction, controlling the function of the receptor CCR2 to thereby promote or inhibit cell migration, calcium mobilization, receptor clusterization, receptor internalization and so on.
2. Providing, as an antigen, an antibody against a FROUNT protein and being available as a probe for detecting the FROUNT protein.

That is, FROUNT protein 1 has the above function 1 while FROUNT proteins 2 to 18 have at least the above function 2. The term "FROUNT protein" as used herein means a protein having one of the above functions 1 and 2.

(10) Scope of the FROUNT Protein According to the Present Invention

All of the DNA sequence data obtained by sequencing the DNA molecules in the present invention are obtained by using an automatic DNA sequencer (Model ABI377 manufactured by Applied Biosystems) and the amino acid sequences of the polypeptides according to the present invention are deduced based on the translation of the DNA sequences thus determined. As widely known in this technical field, there is a possibility that each of the DNA sequences thus determined by using the automatic DNA sequencer has some errors. Therefore, each DNA sequence thus determined should be regarded as having typically at least 90% identity, still typically at least about 95% to 99.9% identity, to the actual DNA sequence. Accordingly, the present invention involves in its scope a DNA consisting of a sequence having at least 90% identity to a DNA represented by any of SEQ ID NOS:19 to 36 and a polypeptide consisting of a sequence having at least 90% identity to a polypeptide represented by any of SEQ ID NOS:1 to 18. The problem concerning errors in DNA sequencing as described above also arises in the sequences 39 and 40 (and, moreover, 37 and 38) as will be described hereinafter. In these cases, therefore, the determined DNA sequences and the amino acid sequences deduced therefrom should be regarded as having typically at least 90% identity, still typically at least about 95% to 99.9% identity, to the actual DNA sequences too.

(11) Medical Applicability of the Protein According to the Present Invention

It is reported that CCR2- or CCR5-mediated chemotaxis of monocytes and macrophages plays important roles in inflammation reactions and participates in chronic inflammatory diseases such as arteriosclerosis and autoimmune diseases. Furthermore, it is known that these chemokine receptor molecules are essentially required in cell entry of human immunodeficiency virus (HIV). Thus, it is considered that chemokine receptor signal controllers, molecules carrying a part of a FROUNT protein, association-inhibiting molecules or antisenses are usable in preventing and treating these inflammatory diseases and infections such as AIDS (acquired immunodeficiency syndrome) induced by HIV and so on. Namely, these molecules are expected as being useful as novel targets for establishing therapeutic methods.

FROUNT protein 1 exerts an effect of promoting the CCL2-CCR2 pathway of monocytes and macrophages, while its inhibitor, antibody and antisense exert an inhibitory effect. Therefore, it is expected that FROUNT protein 1 and its gene are usable in treating diseases caused by lowering in the functions of monophages and macrophages in the CCL2-CCR2 pathway, for example, as immunoenhancers, self-defensive reaction promoters or compositions for treating infectious diseases. On the other hand, it is expected that the inhibitor, antibody and antisense thereof are usable in treating diseases caused by hyper-reactions in the CCL2-CCR2 pathway, for example, as compositions for treating atherosclerosis, chronic glomerulonephritis and multiple sclerosis, immunomodulators or antiallergic agents.

Since molecules highly homologous with FROUNT protein are observed even in the nematode and yeast having no leukocyte, there is a sufficiently high possibility that FROUNT-like proteins would control signal transduction systems from individual receptors not only in other leukocyte chemotactic molecules but also in hormones and G protein-coupled receptors such as neurotransmitter molecules. Namely, these FROUNT-like proteins are expected as contributing to the provision of clinical targets over a wide range beyond the field in which chemokines act. A method of screening a novel agonist and antagonist with the use of, as an indication, the association of a G protein-coupled receptor with a signal-controlling molecule or clusterization of these molecules in response to ligand stimulation is highly useful.

For example, a compound capable of inhibiting ligand stimulation is screened by stimulating cells, wherein a FROUNT protein fused with a fluorescent protein and receptor(s) CCR2 and/or CCR5 are forcibly expressed, with combinations of individual ligands with various compounds and using clusterization of the FROUNT protein thus induced as an indication. It is found out that this method might be available as a novel system by which a compound controlling signaling of the receptor CCR2 or CCR5 can be easily screened.

FROUNT protein 1 exerts an effect of promoting the CCL2-CCR2 pathway of monocytes and macrophages, while its inhibitor, antibody and antisense exert an inhibitory effect. An association domain peptide has a competitive effect to FROUNT protein 1 to thereby inhibit its activity. Similar results are obtained by directly transferring the association domain peptide into a cell or transferring a gene fragment thereof into a cell and forcibly expressing therein. Accordingly, use can be made of FROUNT protein 1, its gene, an inhibitor, an antibody and an antisense thereof, the association domain peptide and an antibody, a gene encoding the association domain peptide, an antisense thereof, etc. in preventing and treating chronic inflammatory diseases and infectious diseases wherein the CCL2-CCR2 pathway and the CCL3, 4, 5-CCR5 pathways of monocytes and macrophages participate.

It is expected that peptides having an association domain sequence, among FROUNT proteins 2 to 18, are expected as having a function similar to FROUNT protein 1. On the other hand, peptides having no association domain sequence are usable as probes, antigens for acquiring antibodies, and so on. Such a probe or antibody is useful in detecting and quantifying FROUNT protein 1. Moreover, it is expected that an antibody and a probe selective to each clone enable quantitative understanding of the balance among FROUNT proteins 1 to 18 potentially expressed in cells, thereby contributing to the clarification of the relationship to diseases.

(12) Process of Producing the FROUNT Protein According to the Present Invention

An expression vector can be obtained by connecting a cloned gene of the FROUNT protein according to the present invention to the downstream of a promoter in a vector appropriate for expression. Examples of the vector include plasmids originating in *Escherichia coli* (for example, pBR322, pBR325, pUC12 and pUC13), plasmids originating in *Bacillus* strains (for example, pUB110, pTP5 and pC194), plasmids originating in yeasts (for example, pSH19 and pSH15), bacteriophages such as λ phage and animal viruses such as retrovirus and vaccinia virus.

To express the gene, a promoter is further connected to the upstream. The promoter usable therefor may be an arbitrary one so long as it is adequate for the host to be used in the gene expression. In the case of using *E. coli* as the host, for example, use may be made of trp promoter, lac promoter, recA promoter, λPL promoter, lpp promoter and so on. In the case of using a host belonging to the genus *Bacillus*, use may be made of SP01 promoter, SP02 promoter, penP promoter and so on. In the case of using a yeast as the host, use may be made of PH05 promoter, PGK promoter, GAP promoter, ADH promoter and so on. In the case of using *E. coli* as the host, it is particularly preferable to use trp promoter or λPL promoter. In the case of using an animal cell as the host, it is preferable to use an SV40-origin promoter, a retrovirus promoter, etc. and an SV40-origin promoter is still preferable.

Using the vector thus constructed, a transformant is prepared. As the host, use can be made of, for example, *E. coli*, a *Bacillus* strain, a yeast, an animal cell and so on. Examples of *E. coli* include *E. coli* K12DH1 (Proc. Natl. Sci. USA 60:160 (1968)), *E. coli* M103 (Nucleic Acids Research 9:309 (1981)), *E. coli* JA221 (J. Mol. Biol. 120:517 (1978)), *E. coli* HB101 (J. Mol. Biol. 41:459 (1969)), *E. coli* C600 (Genetics 39:440 (1954)) and so on. Examples of the *Bacillus* strain include *Bacillus subtilis* MI114 (Gene 24:255 (1983)), *Bacillus subtilis* 207-21 (J. Biochem. 95:87 (1984)) and so on. Examples of the yeast include *Saccaromyces Cerevisiae* strains AH22R, NA87-11A, DKD-5D and so on. Examples of the animal cell include COS-7, Vero, CHO, mouse L cell, human FL cell and so on.

E. coli is transformed in accordance with, for example, a method described in Proc. Natl. Acad. Sci. USA 69:2110 (1972) or Gene 17:107 (1982). A Bacillus strain is transformed in accordance with, for example, a method described in Molecular & General Genetics 168:111 (1979). A yeast is transformed in accordance with, for example, a method described in Proc. Natl. Acad. Sci. USA 75:1929 (1978). An animal cell is transformed in accordance with, for example, a method described in Virology 52:456 (1973). It is appropriate to culture the obtained transformant in a liquid medium by a method commonly known in the art.

The FROUNT protein can be separated and purified from the culture by harvesting the microbial cells or animal cells from the culture by a known method, suspending the cells in a buffer solution containing a protein degenerating agent such as guanidine hydrochloride, disrupting the cells by ultrasonication, lysozyme-treatment, freezing-thawing, etc. and then collecting the supernatant by centrifugation. Next, the FROUNT protein is purified and isolated from the supernatant by using, for example, salting out, precipitation from a solvent, dialysis, ultrafitratin, gel filtration, SDS-polyacrylamide electrophoresis, ion-exchange chromatography, affinity chromatography, reversed-phase high performance liquid chromatography, isoelectric focusing or a combination of these procedures.

(13) Method of Administering the Full-Length DNA According to the Present Invention or a Part Thereof A required DNA can be transferred into a cell by applying a known method having been already established. Typical examples of such methods include a method which comprises integrating the DNA into an adenovirus-origin vector or a retrovirus-origin vector and administering as a plasmid and another method of administering as a liposome preparation.

A liposome is a closed vesicle made of a lipid bilayer membrane and having an aqueous layer therein. It is known that this lipid bimolecular membrane structure is closely similar to a biomembrane. Examples of the phospholipid to be used in producing the liposome preparation according to the present invention include phosphatidylcholines such as lecithin and lysolecithin, acidic phospholipids such as phosphatidylserine, phosphatidylglycerol, phosphatidylinositol and phosphatidic acid, phospholipids derived therefrom by substituting acyl group by lauroyl group, myristoyl group, oleoyl group, etc., shingophospholipids such as phosphatidyl ethanolamine and sphingomyelin and so on. It is also possible to add cholesterol, etc. thereto. It is also possible to produce a liposome from natural materials such as lipids usually occurring in cell membrane by a method commonly known in the art. A liposome preparation containing the FROUNT protein gene according to the present invention can be produced by, for example, suspending a thin phospholipid membrane having been purified in a solution containing the FROUNT protein gene and subjecting to ultrasonication.

The liposome preparation containing the FROUNT protein gene according to the present invention may be in the form of a membrane-fused liposome prepared by fusing with an appropriate virus or the like. In this case, it is preferred that the virus has been inactivated by using, for example, UV rays. As a particularly preferable example of the membrane-fused liposome, a membrane-fused liposome fused with Sendai virus (hemagglutinating virus of Japan; HVJ) may be cited. This membrane-fused liposome can be produced by a method described in J. Biol. Chem. 266(6), 336-3364 (1991). For example, an HJV-fused liposome preparation can be prepared by mixing purified HJV having been inactivated by UV-irradiation with a suspension of liposomes containing a FROUNT protein gene vector, gently stirring the mixture and then removing the unbound HJV by the sucrose density gradient centrifugation method. Moreover, the gene transfer efficiency into a cell can be elevated by binding a substance having an affinity for the cell (for example, an antibody, a ligand to a receptor, etc.) to the liposome.

(14) Antisense

An antisense which inhibits the expression of the FROUNT protein in a cell includes antisense nucleic acids (RNA or DNA) causing inhibition in the step of transcription, inhibition in the step of RNA processing, inhibition in the step of membrane permeation of RNA and inhibition in the step of translation. Furthermore, a DNA producing an antisense RNA in a cell can be used with the purpose of inhibition in the present invention. Examples of the antisense nucleic acid molecule according to the present invention include a nucleic acid molecule complementary to the sense nucleic acid encoding FROUNT protein, a nucleic acid molecule complementary to the regulatory domain of genomic DNA, a nucleic acid molecule complementary to an mRNA sequence and so on.

As an example of the antisense nucleic acid molecule according to the present invention, the full-length of the RNA sequence represented by SEQ ID NO:39 or a part thereof may be cited. The RNA sequence represented by SEQ ID NO:39 shows an antisense strand of the site encoding the C-terminal sequence consisting of 57 amino acid residues in FROUNT protein 13. It is confirmed that an antisense nucleic acid derived therefrom brings about reduction in mRNA in cells not only in FROUNT gene 13 but also in FROUNT gene 1.

It is not always required that the antisense nucleic acid molecule usable herein is complementary to the entire coding domain. Namely, it may be an oligonucleotide which is complementary to a part of the coding or non-coding domain of mRNA or a part of a genomic DNA regulatory domain. The length of the antisense oligonucleotide can be selected from among, for example, 5, 10, 15, 20, 30, 40 ad 50 nucleotides.

The antisense nucleic acid according to the present invention can be constructed by chemical synthesis or enzymatic ligation which has been known in the art.

The antisense nucleic acid according to the present invention can be administered in the form of an RNA molecule. Alternatively, it may be administered as a DNA molecule capable of expressing the RNA molecule in a cell. For example, the full length of the RNA sequence represented by SEQ ID NO: 39 or a part thereof may be administered. It is also possible that the full length of the DNA sequence represented by SEQ ID NO:40, which corresponds to the above sequence, or a part thereof is administered to thereby allow the expression of the corresponding RNA in a cell.

As an example of the administration route of the antisense nucleic acid molecule according to the present invention, it may be directly injected into a tissue site in the form of such a liposome preparation as described above or a plasmid having the antisense nucleic acid molecule integrated into a known virus vector. It is also possible that the antisense nucleic acid molecule is modified so as to target a specific tissue and then systemically administered. For example, the antisense nucleic acid molecule can be modified so as to target a selected cell or tissue by binding a peptide or an antibody binding to a cell surface receptor or a cell surface antigen. The antisense nucleic acid molecule according to the present invention may be transported into a cell by using a vector as described above. To achieve a sufficient antisense molecule concentration in the cell, it is preferable to use a vector structure wherein the antisense nucleic acid molecule is under the control of pol II or III promoter.

The present invention further involves a ribozyme for lowering the activity of the FROUNT protein in a cell. This ribozyme is a catalytic RNA molecule which contains a domain complementary to mRNA and has a ribonuclease activity of cleaving the RNA strand. By catalytically cleaving the FROUNT protein mRNA with the use of the ribozyme, the translation of the FROUNT protein can be inhibited. As a typical example of the ribozyme usable in the present invention, a hammerhead ribozyme (Haseruhoff and Gerluch, Nature 334:585-591 (1988)) can be cited. A ribozyme specific to a nucleic acid encoding the FROUNT protein can be designed based on the DNA sequence represented by SEQ ID NO:19 disclosed in the present description (see, for example, Cech et al., U.S. Pat. No. 5,116,742 and U.S. Pat. No. 4,987,071).

The ribozyme can be transported into a cell by directly injection. Alternatively, the transportation can be also made by integrating the ribozyme in the form of the corresponding DNA into an inactivated retrovirus vector, transforming a cell with it and then expressing the ribozyme RNA in the cell.

(15) Antibody

The polypeptides represented by SEQ ID NOS:1 to 18, fragments thereof or analogs thereof are usable as immunogens for producing antibodies immunospecific respectively to FROUNT proteins. An antibody against a polypeptide according to the present invention can be obtained by administering the polypeptide or an epitope-carrying fragment or analog thereof to an animal (preferably a nonhuman animal such as rabbit, goat or mouse) in a conventional manner. In preparing the immunogen, use can be made of an adjuvant or a similar immunostimulant. To produce a monoclonal antibody, it is possible to employ an arbitrary technique by which an antibody produced by continuous cell culture can be provided. Examples of such techniques include the hybridoma technique (G. Kohler et al., Nature (1975) 250:495-497), the human B cell hybridoma technique (Kozbor et al., Immunology Today (1983) 4:72), the EBV hybridoma technique (Cole et al., MONOCLOAN ANTIBODIES AND CANCER THERAPY, p. 77-96, Alan R. Liss (1985)) and so on.

The antibody against the FROUNT protein according to the present invention can be used in, for example, quantifying or detecting the FROUNT protein. If necessary, the antibody can be labeled with a marker.

(16) Method of Screening Inhibitor

In association with the intracellular localization due to internalization of receptors CCR2 and/or CCR5 stimulated with a ligand (clusterization), the FROUNT protein according to the present invention, in particular, the FROUNT protein having a function of associating with the intracellular C-terminal domain of receptor(s) is localized together with the receptor(s) in the cell. By examining the occurrence of the intracellular localization of a marker-labeled FROUNT protein, therefore, the presence or absence of interaction between the receptor(s) and the ligand can be checked. That is to say, an agonist inhibitor against the receptor(s) CCR2 and/or CCR5 can be identified by forcibly expressing a marker-labeled FROUNT protein in a cell, further expressing the receptor(s) CCR2 and/or CCR5 therein, treating the cell with an agonist to CCR2 and/or CCR5 and a ample which is a candidate for an inhibitor, observing whether or not the clusterization of the receptor(s) is induced, and thus judging whether or not the candidate has an inhibitory effect on the agonist. As the labeling agent, use may be made of any marker so long as it has no cytotoxicity and does not inhibit the activity of the FROUNT protein. Use can be made of an appropriate substance selected from among various fluorescent proteins such as a green fluorescent protein, a red fluorescent protein, a blue fluorescent protein and a yellow fluorescent protein which are available from CLONTECH Laboratories, Inc. (USA). Among all, it seems preferable to employ a red fluorescent protein which is highly distinguishable from the background of the cell. Such a fluorescent protein can be easily expressed in the state of being fused with the FROUNT protein by a conventional method.

By combining fluorescent proteins with different colors, clusterization can be observed depending on color change, which facilitates the detection. For example, the intracellular localization of FROUNT protein 1 fused with a green fluorescent protein and the intracellular localization of CCR2 protein fused with a red fluorescent protein are loaded and superposed by using a fluorescent microscope. Thus, the colocalizatoin of the green fluorescence and the red fluorescence can be visualized and quantified as yellow fluorescence.

The green fluorescent protein is a protein consisting of 238 amino acid residues and emitting green light (509 nm) when irradiated with light at 350 to 490 nm. It requires neither any other protein, substrate nor auxiliary factor for the light emission. Because of being well expressed in various cells as a soluble light-emitting protein, this gene is used as a reporter gene. By substituting serine at the 65-position of this protein by alanine, leucine, cysteine or threonine, its light emission efficiency can be considerably elevated. These derivatives are also usable in the present invention.

As the red fluorescent protein, yellow fluorescent protein and blue fluorescent protein which are obtained through mutation of the green fluorescent protein gene, genes and proteins are marketed from, for example, CLONTECH Laboratories, Inc. (USA).

Known methods for detecting the occurrence of stimulation with a ligand include a method of detecting cell chemotaxis, a method of detecting $Ca^{++}$ produced in a cell, and so on. In these methods, however, a large number of cells are needed or the detection procedures are troublesome. According to the method of the present invention, in contrast thereto, judgment can be made merely by using several cells and microscopically observing the cells after the stimulation. Namely, in the case where the marker is localized in the cells, it is judged that the ligand has not been inhibited. In the case where the marker is scattered in the cells, it is judged that the ligand has been inhibited. Since screening can be carried out with the use of a small number of cells, it can be concluded that this method is highly advantageous in treating a large number of cells.

The new screening method with the use of a FROUNT protein thus established has been further improved to thereby provide a novel screening method which has never been known so far. That is, a method of screening an inhibitor by taking advantage of the phenomenon that clusterization of a receptor and a signal transducing molecule on cell surface is induced in response to stimulation with a ligand. There are molecules other than FROUNT proteins which couple or associate with the intracellular terminus of receptors. Examples of such molecules include G proteins, etc. It is also known that not only chemokines but also hormones act on receptors to cause clusterization. Thus, it is intended to propose a method of screening an antagonist which comprises preparing a cell having a receptor undergoing clusterization in response to stimulation with an agonist and a marker-labeled molecule coupling or associating with the intracellular C-terminal domain of the receptor having been forcibly expressed therein, treating the cell with an agonist and a specimen containing a candidate for an antagonist, then observing whether or not the clusterization of the marker is induced in the cell, and a cell therefor. Typical examples of the receptor include transmembrane receptors interacting with chemokines or cytokines, in particular, 7-transmembrane receptors, I type cytokine receptors, tyrosine kinase receptors, serine/threonine receptors and so on. In the 7-transmembrane receptors, examples of molecules coupling or associating with the intracellular C-terminal domain of the receptors include FROUNT proteins as well as G proteins, GRKs, Arrestins and so on. In such a case, the above-described colocalization can be utilized by labeling both of the receptor and the molecule coupling or associating with the intracellular C-terminal domain of the receptor with proteins emitting lights in different colors.

As an application example of the method of screening an inhibitor with the use of the phenomenon that clusterization of a receptor on cell surface is induced in response to stimulation with a ligand, a method with the use of a chimeric receptor may be cited. Namely, a method of screening an agonist inhibitor with the use of a chimeric receptor cell comprising: forcibly expressing a chimeric receptor, which is obtained by integrating a DNA sequence encoding the full length or a part of a FROUNT protein-association sequence in the intracellular C-terminal domain of the receptor CCR2 (more specifically speaking, the amino acid sequence represented by SEQ ID NO:41) into the intracellular C-terminal domain of the DNA sequence of a desired receptor, in a cell appropriate for the desired receptor; constructing a cell having a labeled FROUNT protein and the chimeric receptor by forcibly expressing a marker-labeled FROUNT protein (for example, a FROUNT protein fused with a green fluorescent protein) in the above-described cell; treating the chimeric receptor cell with an agonist to the receptor and a candidate substance (a specimen) for an agonist inhibitor; and then observing whether or not the localization of the marker is induced in the chimeric receptor cell. In this method, the chimeric receptor and the marker-labeled FROUNT protein can be easily expressed in the cell by using plasmids obtained by integrating DNA sequences respectively encoding the same into known expression vectors. In this case, the above-described colocalization can be utilized by labeling both of the chimeric receptor and the FROUNT protein with proteins emitting lights in different colors. The present invention further involves in its scope such plasmids and cells transformed by these plasmids.

Furthermore, the present invention involves in its scope a method of identifying an intracellular signal transduction pathway inhibitor depending on the binding of a FROUNT protein to a receptor with the use of the characteristics of the FROUNT protein which comprises using the binding activity of the FROUNT protein to the receptor as an indication and screening a substance inhibiting the binding activity.

According to the screening methods of the present invention as described above, an inhibitor can be accurately screened by using an extremely small number of cells for a desired combination of a receptor with an agonist.

By combining the phenomenon of the association of a FROUNT protein with the C-terminal domain of a receptor with a labeling agent as in the present invention, clusterization and colocalization can be visualized. Namely, biological phenomena in cells can be more easily grasped, observed and detected directly with eye compared with the existing methods. Moreover, it is expected that various cells transformed by the above procedure are widely applicable and usable in detecting cytotoxic substances, detecting environmental pollutants, examining cytotoxicity of drugs and so on. It is also possible to judge whether or not a specimen contains a cytotoxic substance by treating a cell having been transformed by the procedure according to the present invention with the specimen, then treating it with an agonist to the receptor carried by the cell and observing whether or not clusterization or colocalization is induced. Use of the cells according to the present invention makes it possible to carry out various detections at a high accuracy with the use of an extremely small number of cells.

(17) Diagnosis and Examination

It is considered that the absence, abnormal amount or abnormality in the sequence of a protein or nucleic acid associating with the intracellular C-terminal domain of a receptor would relate to abnormality in intracellular signal transduction and, therefore, likely affect the extent of efficacy or side effects of drugs. Accordingly, it is expected that the examination on the presence or absence of the above-described abnormalities provide important clues in diagnosing diseases. That is to say, detection of these factors provides novel means of understanding disease conditions which has never been available so far. For example, a FROUNT protein can be quantified by using an antibody, while a mutation in a sequence can be examined by applying known procedures, e.g., determining the sequence of a DNA or RNA fragment collected from a specimen and comparing it with a normal sequence, or by screening a DNA sequence contained in a specimen with the use of a probe having a sequence complementary with DNA sequence encoding a normal FROUNT protein and examining whether or not complete hybridization arises.

Now, the present invention will be described in greater detail by referring to the following EXAMPLES, though it should be understood that the invention is not restricted thereto.

Example 1

Isolation of Clone 19

(1) Preparation of THP1-Origin cDNA Library Fusing with Transcriptional Activation Domain of Yeast Gal4

RNA was extracted form THP-1 cells (ATCC:TIB-202) by using the guanidine isothiocyanate method (Chirgwim et al., Biochemistry 18, 5294 1978). From this RNA, poly(A)RNA was purified by oligo dT cellulose column chromatography (Aviv & Leder, Proc. Natl. Acad. Sci. USA 69:1408 (1972)). By using the thus obtained poly (A) RNA as a template, a THP1-origin cDNA library fusing with the transcriptional activation domain of yeast Gal4 was prepared by using a pACT2 vector (CLONTECH Laboratories, Inc.,) in accordance with the method of Okayama and Berg (Okayama & Berg, Mol. Cell. Biol. 2:161 (1982); ibid., 3:280 (1983)). Then this cDNA library was transferred into *E. coli* DH10B and plasmid DNA was extracted by the alkali method (Birnboim, H. C. & Doly, J., Nucleic Acids Res. 1:1513 (1979)). Thus, a cDNA library consisting of about $2 \times 10^5$ clones was prepared with the use of *E. coli* DH10B as the host.

(2) Construction of Vector Expressing Fused Protein Composed of DNA-Binding Domain of Yeast GAL4 and Intracellular C-Terminal Sequence (the Residues 309 to 360) of Human CCR2

A bait fragment containing the amino acid residues 309 to 360 in the intracellular C-terminal side of human CCR2b was amplified by a polymerase chain reaction (PCR) method by pCMGS-CCR2b in accordance with J. Sambrook et al., Molecular Cloning: A Laboratory Manual, 2nd ed. (1989) with the use of a forward primer 5'GCGAATTCGAGAAGT-TCAGAAGGTAT3' (SEQ ID NO: 42) and a reverse primer 5'GCGGATCCTTATAAACCAGCCGAGAC (SEQ ID NO:43). The thus amplified fragment was treated with restriction enzymes (EcoRI and BmaHI) and then orientationally cloned into pACT2 (a yeast Gal4 DNA binding domain cloning vector containing TRYP gene for selection in a yeast lacking tryptophan biosynthesis (CLONTECH Laboratories, Inc.)). The base sequence of the bait fragment of this plasmid DNA was amplified by the PCR method with the use of a primer specific to the adjacent sequence of the vector in accordance with the dideoxynucleotide chain termination method (J. Messing et al., Nucleic Acids Res. 9:309, (1981)). Then the base sequence was determined by using an automatic DNA sequencer (Model ABI377 manufactured by Applied Biosystems).

(3) Transfer of the Above Vector into Yeast Cells and Isolation of Yeast Cells Showing Interaction The THP1-origin cDNA library and bait vector as described above were transformed into a yeast strain Y190 in accordance with the lithium acetate/polyethylene glycol transformation protocol (see, Ito et al., J. Bacteriol. 153:163-168 (1983)). On a synthetic complete (SC) medium lacking tryptophan, leucine and histidine (SC Trp Leu His) and containing 10 mM of 3-aminotriazole (Sigma Chemical Co.), a vector transformant encoding a library protein interacting with the C-terminal sequence of human CCR2 was selected. Next, the interaction between proteins was quantified by using β-galatosidase activity as an indication by the colony lift β-galactosidase filter assay (Breeden and Nasmyth, Cold Spring Harbor Quant. Biol. 50:643-650 (1985)) and thus yeast cells showing the interaction occurring therein were isolated.

(4) Isolation of Vector from Positive Yeast Cells, Determination of Base Sequence and Confirmation of Interaction Specificity Yeast cells positive to protein interaction, which contained a mixture of a binding domain plasmid with an activation domain plasmid, were re-cultured as an isolated matter in each well of a 96-well microtiter plate. Then, about 10 µl of each isolated matter was dissolved and an insert in the pACT2 plasmid was amplified by PCR with the use of primers specific to the adjacent sequences of individual vectors. The base sequence of the insert was isolated and determined by the above-described method. Thus, the sequence (SEQ ID NO:38) of a gene (clone 19) encoding 156 amino acids was identified and compared with publicly known sequences by using a "BLAST" program available in public mediated by National Center for Biotechnology Information (NCBI). Thus, it was confirmed that this clone was a novel gene the function of which had never been analyzed. The gene (clone 19) encoding 156 amino acids was named FROUNT gene and the isolated plasmid clone was named pACT2-FROUNT. To confirm the binding specificity of the protein (FROUNT protein) encoded by the FROUNT gene (clone 19), the following two tests commonly employed in the art were first carried out.

In the first test, Y190 cells expressing individual plasmids containing DNA sequences encoding FROUNT protein and receptors CCR5 and CCR2 and sequences encoding FROUNT protein:p53 (CLONTECH Laboratories, Inc.,), FROUNT protein:CXCR4, FROUNT protein:CCR5 and FROUNT protein:CCR2 were prepared in the same manner. When the proliferating ability and β-galactosidase activity of these yeast cells were tested, no combination other than FROUNT protein:CCR2 and FROUNT protein:CCR5 showed any proliferating ability or β-galactosidase activity. Thus, it was confirmed that FROUNT protein is not a "self-activating" protein (i.e., requiring the interaction with a second protein domain to form a functional activated complex) and that FROUNT protein has binding ability specific to the receptors CCR2 and CCR5 (FIG. 1). In FIG. 1 which shows the results of a yeast two-hybrid assay, GAL4 BD and GAL4 AD respectively stand for a transcriptional factor binding domain-fused protein expression vector and an activation domain-fused protein expression vector; BD or AD vector stands for a control (empty) vector; FROUNT, p53, SV40 T-antigen, CCR5, CXCR4 and CCR2 stand for transferred genes; each numerical value in parentheses indicates the number of inserted amino acid residues; -LDH stands for proliferating ability in the deficient medium; β-Gal activity stands for β-galactosidase activity; and + and − stand respectively for the presence and absence of the activity.

In the second test, coding sequences of pAS2-1-CCR2b and pAS2-1-p53 were amplified by PCR using a T7 promoter, a 5' primer encoding myc epitope: 5'AAAATTGTAATAC-GACTCACTATAGGGCGAG CCGCCACCATGGAG-GAGCAGAAGCTGATCTCAGAGGAGGAC-CTGGTATCGCCGGTATTG 3' (SEQ ID NO:44) and a 3' primer originating in p AS2-1: 5'CAGCTATGACCATGAT-TACGC3' (SEQ ID NO:45) to express an epitope-tagged protein. Similarly, pACT2-FROUNT was amplified by PCR using a T7 promoter, a 5' primer encoding HA epitope: 5'AAAATTGTAATACGACTCACTATAGGGC-GAGCCGCCACCATGTACC CATACGACGTTCCAGAT-TACGC3' (SEQ ID NO:46) and a 3' primer originating in p ACT2: 3'ACTTGCGGGGTTTTTCAGTATCTACGAT5' (SEQ ID NO:47). Then, isotope-labeled recombinant proteins were produced in accordance with user's manual of MATCHMAKER Co-IP Kit (CLONTECH Laboratories, Inc.). By the coimmunoprecipitation method using these recombinant proteins, the specific binding ability between CCR2 and FROUNT was confirmed again (FIG. 2). In FIG. 2 which shows the results of SDS-PAGE analysis in coimmunoprecipitation, myc-CCR2, p53 and HA-FNT stand for isotope-labeled myc or HA-fused recombinant protein; I.P. stands for an antibody employed in the coimmunoprecipitation of each sample; HA mAb and Myc mAb stand for antibodies specific for Ha and Myc respectively; HA-peptide and Myc-peptide stand for antigen peptides; and + and − respectively stand for the presence and absence for each sample. Namely, coprecipitation occurred by using the HA- or Myc-specific antibody in the coexistence of myc-CCR2 and HA-FNT, the coprecipitation disappeared by adding an antigen peptide and no coprecipitation occurred in the case of myc-p53, thereby indicating specific binding ability.

Example 2

Isolation of Full-Length cDNA (Clone 1)

THP-1-origin cDNA prepared by using the same method as in the preparation of the plasmid cDNA library in EXAMPLE 1 was inserted into a λ phage vector λZIP (GIBCO BRL) to give a phage cDNA library using *E. coli* DH10B as the host. The phage cDNA library using *E. coli* DH10B as the host was sowed on 10 soft agar plates at a density of about $1 \times 10^5$ clones per plate. After transferring on a nitrocellulose filter (HATF filter, MILLIPORE), the library was dissolved in a 0.5 N NaOH solution and the phage DNA thus exposed and denatured was dried and immobilized on the filter (Maniatis et al., Molecular Cloning, Cold Spring Harbor Laboratory, p. 320

(1982)). On the other hand, the above-described FROUNT gene fragment (clone 19) was $^{32}$P-labeled by the Nick translation method (Maniatis et al., ibid., p. 109) and employed as a probe. The labeled probe and the filter having the DNA thus immobilized thereon were subjected to association in 5×SSPE (0.9 M NaCl 50 mM sodium phosphate buffer solution (pH 7.4), 5 mM EDTA) containing the labeled probe, 50% formamide, 5×Denhardt's, 0.1% SDS, 100 µg/ml denatured salmon sperm DNA solution (10 ml) at 42° C. for 16 hours. After the completion of the reaction, the filter was washed in 2×SSC (1×SSC=0.15 M NaCl, 0.015 M sodium citrate) 0.1% SDS solution at room temperature twice each for 30 minutes and then in 1×SSC, 0.1% SDS solution at 68° C. twice each for 30 minutes. After drying the thus washed filter, it was subjected to radioautogram and a clone reacting with the probe was searched for.

From the clone thus obtained, phage DNA was extracted by the method of Davis et al. (Davis et al., Advanced Bacterial Genetics, Gold Spring Harbor Laboratory (1980)) and the cDNA base sequence of the clone reacting with the probe was determined. Further, a cDNA library for racing was prepared from THP-1 cells in accordance with the protocol of 5' race PCR marathon system (TOYOBO). Using this library, the 5'-terminal base sequence of the obtained gene was clarified. Using oligonucleotides chemically synthesized based on the 5'-terminal and 3'-terminal base sequences, human FROUNT gene full-length cDNA was cloned by the PCR method with the use of the THP-1 cell-origin cDNA library as a template. Then the full base sequence was determined by using an ABI377 sequencer (clone 1).

In accordance with Kozak's anticipation (Kozak, M., Cell 44:283-292 (1986)), a potential initiation codon was found out and it was followed by a complete open reading frame encoding a 656 amino acid protein (SEQ ID NO:1/FROUNT protein 1) having a calculated molecular weight of 79 kDa. As the results of a search on Gene Bank, it was found out that FROUNT protein 1 encoded by the clone 1 gene is a novel one. Through database motif searching, it was found out that this protein carries a leucine zipper structure, 4 leucine motives and 4 dileucine motives known as playing important role in protein-protein binding (FIG. 4 and FIG. 5(c)). From the Kyte-Doolittle hydropathy plot, it was estimated that this FROUNT protein is an intracellular protein (FIG. 5(a)). As the results of a search on human genome database (NCBI, BLAST), it was identified that FROUNT genome is encoded as 26 exons in the 17th chromosome (in the neighborhood of D17S785 and D17S1352) similar to CCL's 2, 3 and 5. In homology searching, no known gene or protein having analogous sequence was detected in humans.

FIG. 4 shows the amino acid sequence of human FROUNT protein 1 (hFROUNT) wherein the framed part corresponds to FROUNT conserve domain (FCD), the underlined part corresponds to the part having been isolated by the yeast two-hybrid assay as described above (SEQ ID NO:38), and 4 stars respectively indicate 4 leucine residues conserved in the leucine zipper domain.

FIG. 5 shows the results of the Kyte-Doolittle hydropathy plot of human FROUNT protein 1 wherein the horizontal axis refers to the number of amino acid residues while the longitudinal axis refers to the hydrophobicity of each amino acid residue.

Example 3

Identification of Binding Domain

To search for a site in the human CCR2 C-terminal sequence (the residues 309 to 360) essentially required in the binding to FROUNT protein 1, various expression vectors having mutations in the C-terminal sequence (CR2-1 to CR2-7 in FIG. 3) were constructed as in pAS2-CCR2 and the binding ability to FROUNT protein was examined by using the yeast two-hybrid method as described above. As a result, mutants lacking the residues 329 to 360 in the C-terminus of CCR2 (i.e., CR2-1 to CR2-3 in FIG. 3) sustained the binding ability, while a mutant lacking the residues 317 to 360 in the C-terminus of CCR2 (i.e., CR2-7 in FIG. 3) showed no ability to binding to FROUNT protein. These results suggest that, in the intracellular C-terminal domain (the residues 309 to 360) of CCR2, all of the 12 residues (317 to 328) or a part thereof might be a site essentially required in the binding to FROUNT protein 1. It is also suggested that this site (the residues 317 to 328) essentially required in the binding agrees with the 12 residues (12 C-terminus; SVFFRKHITKRF/SEQ ID NO:41) in CCR2 having been reported as essentially necessary in the activation of the leukocyte chemotactic signal mediated by the CCL2-CCR2 pathway. Moreover, it is known that the activation of the leukocyte chemotactic signal mediated by the CCL2-CCR2 pathway is never affected by the substitution of serine of the residue 317 or threonine of the residue 325 in the 12 residues (317 to 328) of CCR2 essentially required in the binding by alanine. Thus, the binding ability was also examined in mutants wherein serine of the residue 317 or threonine of the residue 325 was substituted by alanine. As a result, it was observed that these CCR2 mutants (CR2-4 to CR2-6 in FIG. 3) sustained the binding ability too.

Based on these results, it has been clarified that the CCR2 site essentially required in the binding to FROUNT protein 1 completely agrees with the CCR2 site essentially required in the activation of the leukocyte chemotactic signal mediated by the CCL2-CCR2 pathway. These results provide sufficient evidence for considering that the binding of FROUNT protein 1 to CCR2 affects the activation of the leukocyte chemotactic signal mediated by the CCL2-CCR2 pathway. Since the mutant at the residues 309 to 328 alone (CR2-3 in FIG. 3) in the CCR2 C-terminal sequence (the residues 309 to 360) sustained the ability to bind to FROUNT protein, this site (the residues 309 to 328) was identified as the binding domain of CCR2 to FROUNT protein. FIG. 3 shows CCR2 mutants (CR2-1 to CR2-7) and the results of the yeast two-hybrid assay using them as in FIG. 1.

Example 4

Comparison of FROUNT Protein Among Species

A cDNA library originating in mouse bone marrow cells was prepared by the above-described method. Then mouse FROUNT gene was isolated as in the human FROUNT protein 1 gene (clone 1/SEQ ID NO:19). By using a software for sequence comparison (Network Protein Sequence, CLUSTALW), it was clarified that the amino acid sequence deduced from the base sequence of the mouse FROUNT gene was highly homologous with human FROUNT protein 1 (FIG. 5(b)). As the results of searching for proteins having high homology with human FROUNT protein 1 in species other than humans and mouse with the use of publicly known database (NCBI, BLAST), FROUNT proteins of *Drosophila melanogaster* and *Caenorhabditis elegans* were identified. These proteins are all in the almost same size, show high homology over the entire domains and sustain sequences having extremely high homology at almost the center of the protein (the residues 397 to 441 of human FROUNT protein 1). This site was named FROUNT conserve domain (FCD) (FIG. 5(c)). These facts indicate that human FROUNT protein is highly conserved in different species too.

FIG. 5(b) shows comparison of FROUNT protein among species and a schematic model of the domain structure of human FROUNT protein 1. In this figure, homology to human FROUNT protein 1 at the amino acid level in FCD, the upstream domain of FCD or the downstream domain of FCD is given in (%). In FIG. 5(c), hFROUNT is a schematic model of the domain structure of human FROUNT protein 1; 4 Y's represent tyrosine motives; 4 L's represent dileucine motives; FCD represents the FROUNT conserved domain; the underlined part in the CCR2 binding site corresponds to the part isolated by the yeast two-hybrid assay as described above; 4 stars represent 4 leucine residues conserved in the leucine zipper domain; and FNT-D Ab and FNT-A Ab represent each the site employed as an antigen in constructing a specific polyclonal antibody.

Example 5

Identification of FROUNT Protein 1 Gene Splicing Mutant

Using the plaque hybrid method, amino acid sequences deduced from the base sequences of other clones isolated from the phage library were examined. As a result, it was clarified that human FROUNT protein seemingly involves at least 2 molecular types, i.e., α-type having 656 amino acid residues and β type having 630 amino acid residues differing from each other exclusively in the C-terminal part. Since FROUNT β-type DNA was encoded in the neighborhood of the C-terminus of the FROUNT protein genome gene, it was confirmed that they are splicing mutants. By using a TOPO TA cloning system (Invitrogen) with the use of oligonucleotides which were chemically synthesized based on the 5'- and 3'-terminal base sequences of the FROUNT α- and β-types, furthermore, the base sequences of a plural number of clones were determined. As a result, it was confirmed that insertion or deletion mutants occurred in both of the FROUNT α- and β-types. Thus, it was clarified that there are at least 18 types of splicing mutants of FROUNT protein 1 in total in the FROUNT α- and β-types (SEQ ID NOS:1 to 18, SEQ ID NOS:19 to 36).

Human FROUNT clone 2 (α-deletion type (FIG. 8)) is a FROUNT mutant having 611 amino acids derived from human FROUNT clone 1 (α-type, 656 amino acids in the full-length (FIG. 7)) by deletion of the bases 662 to 792 (135 bp). Human FROUNT clones 3 to 12 also belong to the α-deletion type.

Human FROUNT clone 14 (β-deletion type (FIG. 10)) is a FROUNT mutant having 611 amino acids derived from human FROUNT clone 13 (β-type, 630 amino acids in the full-length (FIG. 9)) by deletion of the bases 470 to 661 (192 bp). Human FROUNT clones 15 and 16 also belong to the β-deletion type.

Human FROUNT clone 17 (β-insertion type (FIG. 11)) is a FROUNT mutant having 518 amino acids derived from human FROUNT clone 13 (β-type, 630 amino acids in the full-length (FIG. 9)) by insertion of 90 bp between the bases 1581 and 1582 followed by frame shifting. Human FROUNT clone 18 also belongs to the β-insertion type.

In each figure, an underlined part corresponds to the amino acid sequence identical with human FROUNT 1, while ***** represents a deletion or insertion site.

Example 6

Detection of FROUNT Protein and Distribution Thereof in Cell Using Green Fluorescent Protein-Fused FROUNT Protein 1

(1) Construction of Plasmid Vector for Expressing Green Fluorescent Protein-Fused FROUNT in Animal Cell Human FROUNT protein 1 gene (clone 1) was amplified by the PCR method with the use of a 5'-primer: 5'CCCGCTC-GAGCTATGTATTTTGACTGGGGTC3' (SEQ ID NO:48) and a 3'-primer: 5'GCGA ATTCTCAGGAACCTTCCAGT-GAGC3' (SEQ ID NO:49) and then treated with restriction enzymes (XhoI and EcoRI). After inserting into the XhoI, EcoRI site of pEGFP C1 (CLONTECH Laboratories, Inc.), the base sequence of the insert was determined by using an ABI377 Sequencer. Thus, a plasmid vector pEGFP-FROUNT for expression in animal cells was constructed. This plasmid vector was transformed into *E. coli* DH5α in accordance with a method reported in Proc. Natl. Acad. Sci. USA 69:2110 (1972) and a plasmid DNA for transforming animal cells was obtained in accordance with the protocol of Max Prep (Qeagen).

(2) Expression of Green Fluorescent Protein-Fused FROUNT in Animal Cell

Human HEK293 cells (ATCC:CRL-157) were grown by monolayer culture in a DMEM medium containing 5% of fetal bovine serum (Falcon size: 100 mm, 5 plastic dishes). After replacing the medium with a fresh one of the same type, the cells were further cultured in a G418-containing medium after the transformation. 4 hours after the replacement, calcium phosphate gel containing 30 μg/dish of the plasmid pEGFP-C1 (control) or pEGFP-FROUNT DNA was prepared and added to the cells in accordance with a publicly known method (Graham et al., Virology 52:456 (1973)) to give pEGFP-C1 transformed cells or pEGFP-FROUNT transformed cells respectively. 4 hours thereafter, the above pEGFP-C1 transformed cells or pEGFP-FROUNT transformed cells were treated with glycerol and further cultured in a medium containing 5% of fetal bovine serum. 24 and 48 hours after the transformation, the cells were stripped off from the dish by using trypsin and an EDTA solution. Then the expression of the green fluorescent protein (GFP) in the pEGFP-C1 and pEGFP-FROUNT transformed cells was confirmed with the use of a fluorocytometer EPICS ELITE ESP (Beckman Coulter) or EPICS XL/XL-MCL system 2 (Beckman Coulter). Further, the localization of the FROUNT protein in the cells was observed by a publicly known method with the use of a confocal fluoromicroscope. As a result, it was confirmed that the control eGFP was observed all over the cells including nucleus while the GFP-fused FROUNT protein was localized in the cytoplasm other than nucleus (FIG. 6(a)).

In order to clarify the interaction between the green fluorescent protein-fused FROUNT protein 1 and CCR2 in animal cells, a plasmid vector for expressing human CCR2 protein in animal cells was constructed by the same procedure and then transferred into the pEGFP-C1 and pEGFP-FROUNT transformed cells as described above. Then the intracellular localization of the green fluorescent protein was observed before and after stimulating with a CCR2 antibody or CCL2 which is a ligand to CCR2. In the case of the CCL2 stimulation, immunostaining was performed by using a red fluorescent-labeled human CCR2-specific antibody (R&D System Inc.) so as to simultaneously visualize the intracellular localization of the green fluorescent protein-fused FROUNT protein 1 and the CCR2 protein under a fluorescent microscope. By this simultaneous visualization of 2 proteins with the use of green and red fluorescent proteins, the binding and neighboring of proteins in the animal cells could be visualized as yellow fluorescence, i.e., overlapping of green and red fluorescences (colocalization). As a result, little colocalization of the green fluorescent protein-fused FROUNT protein 1 and CCR2 was observed before the CCL2 stimulation but, after the stimulation with the CCR2 antibody or CCL2, colocalization of the green fluorescent protein-fused FROUNT protein 1 was found out in association with the accumulation and localization of CCR2 (FIG. 6(b)). FIG. 6 presents fluorescent microphotographs of cells having control eGFP (upper) and fluorescent protein-fused FROUNT (lower) transferred therein. FIGS. 6(a) and 6(b) respectively show micrographs before and after treating with the CCR2 antibody. The Merge image shows the simultaneous visualization of green fluorescence and CCR2 (red fluorescence). Similar results were observed in the case of the CCL2 stimulation (data not shown).

No such colocalization was observed in the case of stimulating with another chemokine SDF-1 or stimulating cells expressing the control eGFP alone with CCL2. These facts suggest that FROUNT protein 1 would undergo accumulation and clusterization specifically to CCR2 in association with the binding of CCL2 to CCR2. When pEGFP-FROUNT transformed HEK293 cells expressing CCR5 in the same manner were stimulated with RANTES which is a CCR5 ligand, colocalization of FROUNT protein and CCR5 was similarly observed. In the fluorescent microscopic observation, a fluorescent microscope system FV300+IX70 (OLYMPUS) and a cooled CCD camera SenSys (Photometrics)+AX80 (OLYMPUS) were used, while Photoshpop (Adope) was employed in image processing.

Example 7

Preparation of FROUNT Protein 1-Specific Polyclonal Antibody and Detection of Endogenous FROUNT Protein 1

The site common to FROUNT proteins of the α- and β-types in human FROUNT protein 1 gene (clone 1) was amplified by the PCR method with the use of a 5'-primer: 5'CGGGATCCGCCATGTATTTTGACTGGGGTC3' (SEQ ID NO:50) and a 3'-primer: 5'GCGAATTCTCATGACAAAATGGAGACCTGGCTGC3' (SEQ ID NO:51), treated with restriction enzymes (EcoRI and BmaHI) and then orientationally cloned into the EcoRI, BamHI site of pGEX4T3 (Amersham Pharmacia). Then the base sequence of the insert was determined by using an ABI377 sequencer. Thus, a plasmid vector pGX-FROUNT for expressing glutathione S transferase (GST)-fused protein was constructed. This plasmid vector was transformed into E. coli BL21 (DE3) in accordance with a method described in Proc. Natl. Acad. Sci. USA 69:2110 (972)) followed by expression in accordance with a publicly known protocol recommended by Amersham Pharmacia. Then the GST-fused protein was purified by glutathione sepharose affinity chromatography. By SDS PAGE and Coumassie staining, it was judged that the accuracy and purity of this GST-fused FROUNT both exceeded 95%.

This GST-fused FROUNT protein 1 (100 μg) was mixed with an adjuvant and employed in subcutaneously immunizing a New Zealand white rabbit in a publicly known time course. After confirming an increase in the titer, a FROUNT protein 1-specific polyclonal antibody was purified from the serum of the animal. The titer of the FROUNT protein 1-specific polyclonal antibody was confirmed by calibrating the ability to bind to the GST-fused FROUNT protein 1 with the use of the Western blotting method. Endogenous FROUNT protein 1 was detected by a publicly known immunostaining method with the use of the above-described specific polyclonal antibody. It was thus confirmed that the GST-fused FROUNT protein 1 showed localization similar to the green fluorescent protein-fused FROUNT protein 1. These results clearly indicate that FROUNT protein 1 is accumulated specifically in a chemokine receptor and clusterized with the activation of the CCL2-CCR2 pathway or the CCL3, 4 or 5-CCR5 pathway.

Example 8

Analysis of the Function of FROUNT Protein Using Cell Having Antisense Transferred Thereinto (1) Preparation of Antisense Expression Vector and Establishment of Cell Line Partial sequences of a plural number of FROUNT protein genes were amplified by the PCR method. Then each fragment was inserted in the reverse direction into a retrovirus vector pEGFPMY (Onai, N. et al., Blood., 96239-247 2074 (2000)) and the base sequence was determined by using an ABI377 sequencer (FIG. 12). FIG. 12 is a schematic model of the retrovirus vector pEGFPMY wherein Cont stands for a control (empty vector); hFNT stands for an expression vector of human FROUNT protein 1; AS-22 stands for an antisense expression vector of human FROUNT protein; DN-hFNT stands for a partly deficient FROUNT protein expression vector; LTR stands for a long terminal repeat; gag stands for a structural protein; eGFP stands for a green fluorescent protein; and IRES stands for a ribosomal entry site.

Figure 13:
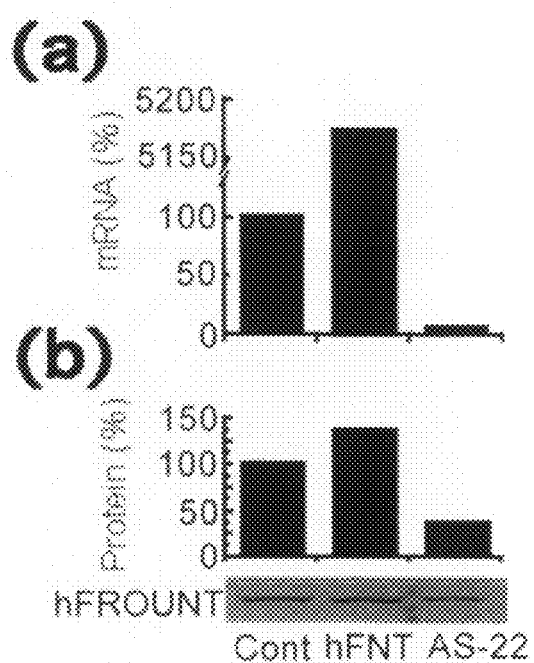
FIG. 13 shows the results of the quantification of human FROUNT mRNA and protein in each established cell line.

These vectors were transferred into Phoenix cells (Dr. Garry P. Nolan) by the above-described transformation method. After 2 days, cell supernatant containing the thus produced recombinant retroviruses was collected. Then HEK293 and THP-1 cells were infected with these recombinant retroviruses and the infected cells alone were separated and purified to a purity of 98% or higher by using a cell sorter system EPICS ELITE ESP (Beckman Coulter) with the expression of eGFP gene encoded by the retroviruses as an indication. From the recombinant retrovirus-infected cells thus purified, RNA was collected by a publicly known method. Using ABI7700, FROUNT mRNA was compared and quantified. As a result, a cell line wherein the expression of about 90% of FROUNT mRNA was inhibited could be established in association with the transfer of an antisense expression vector (AS-22), which was obtained by amplifying a fragment by the PCR method with the use of a 5'-primer: 5'GCGGATCCTCAAATCAAGCAGTGTTTGTC3' (SEQ ID NO:52) and a 3'-primer: 5'CGGGATCCGCCAT-GCTTTTGGAACAGAAACAGGTG3' (SEQ ID NO:53), treating with BamH1 and inserting into pMY, into HEK293 cells by the above-described method (FIG. 13). In quantifying mRNA, use was made of a quantitative TR-PCR system ABI PRISM7700 system (PE Applied Biosystems) and a Taq Man Probe: 5'CCTCGGTCTTTCTGGATGACTCTGCT3' (SEQ ID NO:54), a 5'-primer: 5'CAGCCATGATGCTCAGTGA3' (SEQ ID NO:55) and a 3'-primer: 5'TGGTCTCTATGTCAT-CATCCTG3' (SEQ ID NO:56) were synthesized and employed.

Figure 14:
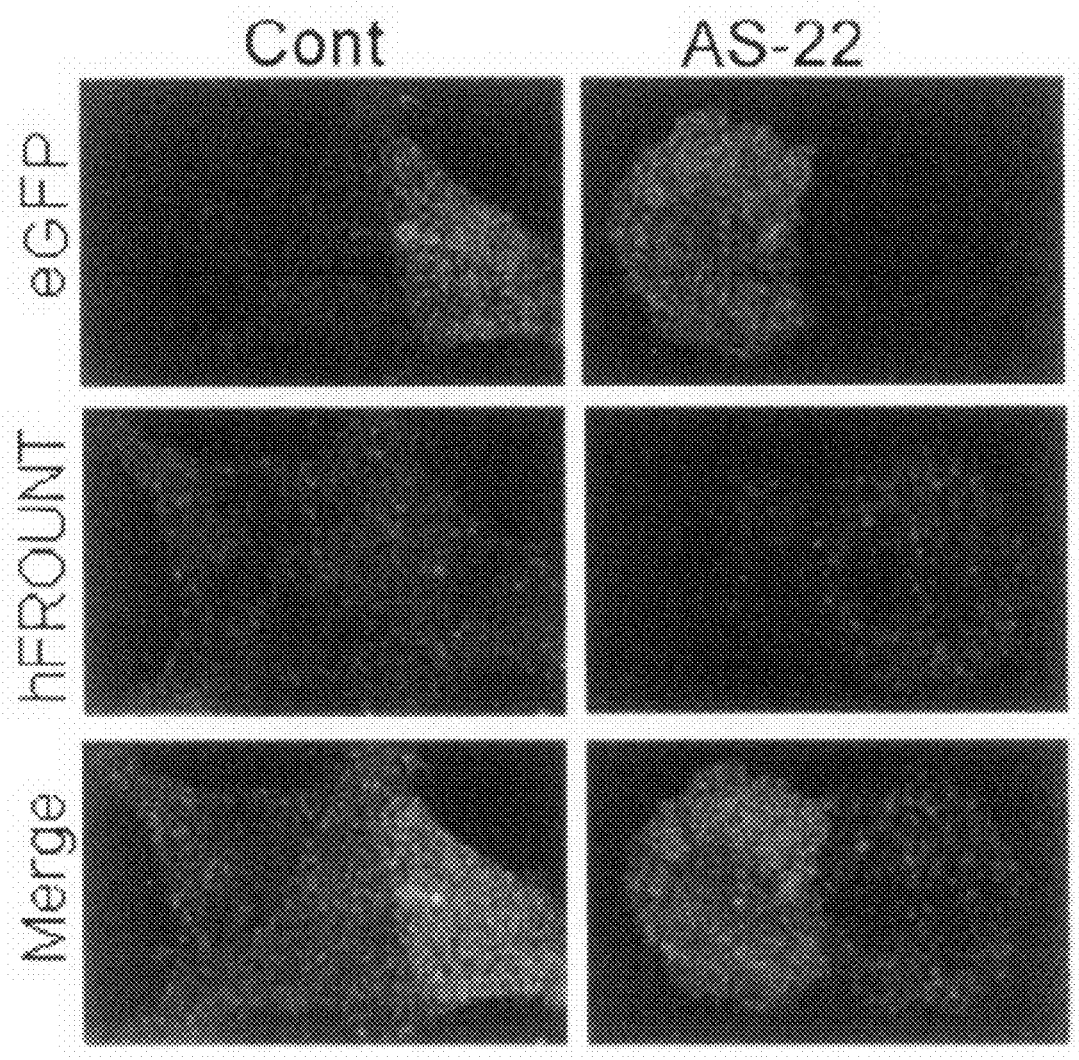
FIG. 14 presents confocal microscopic images of human FROUNT protein in each established cell line.

Moreover, a remarkable lowering was observed in the detection of intracellular FROUNT protein level by the Western blotting method with the use of a FROUNT protein-specific antibody and the immunostaining method (FIGS. 13 and 14). FIG. 13 shows the results of the quantification of human FROUNT mRNA (upper a) and FROUNT protein (lower b) in Cont, hFNT and As-22 cells and the results of Western blotting using FROUNT antibody. FIG. 14 shows confocal fluoromicroscopic observation results of eGFP-expressing cells in Cont and AS-22 cells (virus-transfer cells, upper), expression of FROUNT protein (medium) and overlapped image thereof (lower). Compared with the Cont cells, a remarkable lowering in the FROUNT protein expression was observed in the eGFP-expressing cells (virus-transfer cells).

Subsequently, the function of FROUNT protein in cells was analyzed by using this FROUNT antisense-transfer cells (AS-22 cells).

(2) Construction of Partly Deficient FROUNT Protein Expression Vector and Establishment of Cell In order to establish a cell line inhibiting the binding of endogenous FROUNT to CCR2 and analyze its phenotype, the following vector was constructed by forcibly expressing the C-terminal part alone of FROUNT protein 1 carrying the binding activity to CCR2 identified by the above-described yeast two-hybrid method and the in vitro binding experiment. Using as a template a plasmid vector encoding 156 C-terminal amino acids of FROUNT protein 1 isolated by using the yeast two-hybrid method, a fragment of SEQ ID NO:38 was amplified by the PCR method with the use of a 5'-primer: 5'GCGAATTCGCCGGATCCCGCCGCGTCGAC3' (SEQ ID NO:57) and a 3'-primer: 5'GCGAATTCGGGGTTTTTC AGTATCTACG3' (SEQ ID NO:58) and then treated with EcoR1. Then it was inserted inframe into the C-terminus as allowing fusion to thereby construct a plasmid vector DN-FNT (FIG. 12, upper). Then a virus was prepared as described above and a cell line was infected to establish partly deficient FROUNT protein-expressing cells (DN-hFNT cells).

(3) Analysis of FROUNT Protein Function Using the Above Gene-Transfer Cells (Cont, hFNT, AS-22 and DN-hFNT Cells)

Reactivities in the FROUNT protein antisense gene-transfer cells (AS-22 cells) and the partly deficient FROUNT protein-expressing cells (DN-hFNT cells) were compared and examined in the following 3 experimental lines (3-1 to 3-3) with the use of cells into which the control vector (pEG-FPMY) and the FROUNT sense gene had been similarly transferred.

(3-1) Chemotactic Activity Upon Chemokine Stimulation

Figure 15:
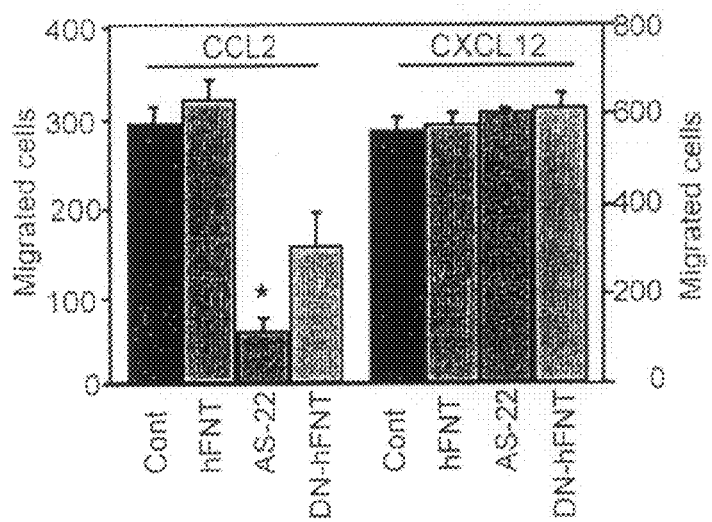
FIG. 15 shows the results of the detection of chemotactic activity.

Participation of FROUNT protein in the cell chemotaxis induced by chemokine stimulation was examined in accordance with the method of Fall et al. (J. Immunol. Methods., 33, 239-247 (1980)). Chemokines dissolved in medium A (RPMI/0.5% BSA) at various concentrations (26 μl) were supplied into the lower chamber of a 96-well micro-chemotaxis chamber (Neuroprobe, 5 μm), while the gene-transfer THP-1 cells dissolved in medium A at a concentration of $10^7$ cells/ml (28 μl) were supplied into the upper chamber and incubated at 37° C. for 30 min. Then 20 μl of 4% paraformaldehyde was added to the lower chamber to immobilize the migrating cells at 4° C. When the cells were counted with a fluorocytometer, it was observed that the chemotactic activities of the AS-22 and DN-hFNT cells toward CCL2 and CCL5 were remarkably lowered compared with the Cont cells and the hFNT cells. However, no difference in chemotactic activity toward CXCL12 was observed among the Cont, hFNT, AS-22 and DN-hFNT cells (FIG. 15). FIG. 15 shows the number of migrating cells (the longitudinal axis) in the cells (Cont, hFNT, AS-22 and DN-hFNT) when stimulated with 33 ng/ml of CCL2 or CXCL12 and FIG. 15(b) shows the number of migrating cells (the longitudinal axis) in respective cells when stimulated with CCL2 at various concentrations.

Figure 16:
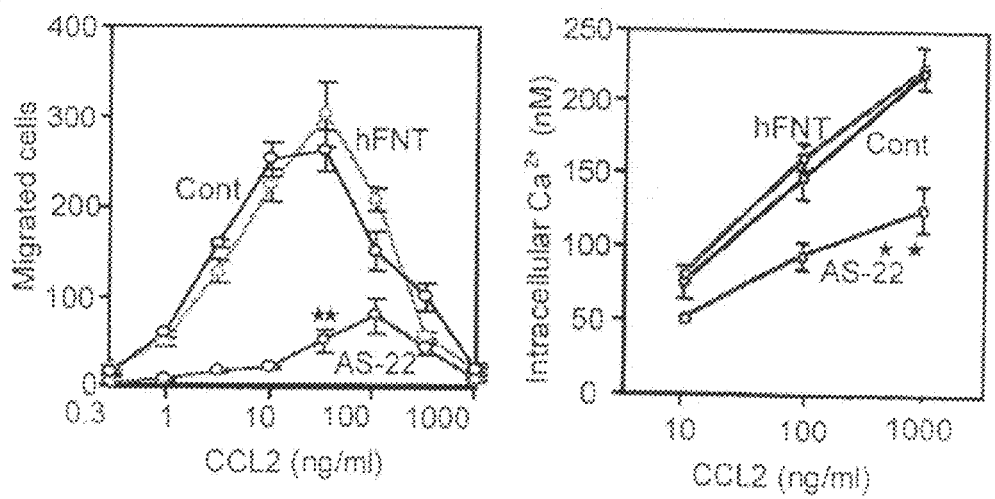
FIG. 16 shows the results of the measurement of the ability of calcium influx.

(3-2) Increase in Intracellular Calcium Concentration ($Ca^{2+}$) in Response to Chemokine Stimulation It is known that a chemokine reacts with a chemokine receptor and thus elevates intracellular calcium concentration ($Ca^{2+}$). Thus, $10^7$ gene-transfer THP-1 cells as described above were washed with PBS (Gibco BRL), suspended in 1 ml of buffer solution A (Tyroid's Salt Solution (Gibco BRL)/ 0.1% BSA) and incubated to a final concentration of 5 μM Fruo3AM (Dojindo) at room temperature for 1 hour. Then the cells were washed with the buffer solution A and suspended in 2 ml of the buffer solution A. The intracellular calcium concentration ($Ca^{2+}$) was measured by using a fluorescent spectrophotometer Fluoroscan Ascent system (Labosystems). As a result, it was confirmed that the intracellular calcium concentration ($Ca^{2+}$) increasing ratios of the AS-22 cells in response to CCL2 and CCL5 were concentration-dependently lowered compared with those in the Cont cells and the hFNT cells (FIG. 16). FIG. 16 shows the results of calcium influx (nM, the longitudinal axis) quantification into various cells stimulated with CCL2 at various concentrations.

(3-3) Clusterization Ability of Chemokine Receptor Using CCR2-Specific Antibody

When a chemokine receptor reacts with a chemokine, a plural number of receptor molecules aggregate and form clusters followed by internalization. The same phenomenon is observed in the reaction between a chemokine reactor and an antibody specific thereto. To examine the participation of FROUNT protein 1 in this clusterization, the above-described gene-transfer HEK293 cells, in which CCR2 was constantly expressed by the above-described method, were bonded to a glass plate. After washing the cells with the medium A at 4° C., a PE-labeled CCR2-specific antibody (R&D System, Inc.) was dissolved in the medium A and incubated at 4° C. for 30 min. Then the cells were washed with the medium A and, after replacing the medium, incubated at 37° C. for 15 min followed by the immobilization of the cells and a treatment with a quencher. Clusterization was observed with the use of the fluoromicroscope system as described above. As a result, it was confirmed that the AS-22 and the DN-hFNT cells showed clearly lowerings in CCR2 clusterization ability due to the PE-labeled CCR2-specific antibody, compared with the Cont and hFNT cells (FIG. 17). FIG. 17(a) presents images of the cells stimulated with the CCR2-specific antibody, while FIG. 17(b) shows the results of the confocal microscopic quantification of the clusterization ability of each receptor stimulated with the CCR2- or CXCL2-specific antibody (the longitudinal axis referring to control %).

(3-4) Inhibition of Chemokine Receptor Clusterization Using MCP-1-Specific Antibody To examine whether or not the clusterization of FROUNT protein 1 is inhibited by an MCP-1-specific antibody, the above-described gene-transfer HEK293 cells, in which CCR2 had been constantly expressed by the above-described method, were bonded to a chamber slide system (Lab-Tek). Then the cells were washed with the medium A at 37° C., replaced and incubated for 1 hour. Separately, an MCP-1 solution (100 ng/ml), a liquid mixture of MCP-1 with an MCP-1-specific antibody and the medium A alone (control) were each pre-incubated at 37° C. for 15 min and then added to the cells having been incubated for 1 hour as described above followed by incubation at 37° C. for additional 15 minutes. Clusterization was observed with the use of a fluoromicroscope system. As a result, it was confirmed that clusterization of FROUNT protein was observed in the case of adding the MCP-1 solution (see FIG. 20(a)) but not in the case of adding the MCP-1-specific antibody mixture (FIG. 20(b)) and in the case of the medium A alone. It was thus confirmed that the MCP-1-specific antibody inhibited the clusterization of FROUNT protein in response to the chemokine stimulation. This fact indicates that a FROUNT protein clusterization inhibitor can be screened by using the gene-transfer HEK293 cells as described above.

Example 9

Analysis of Function of FROUNT Protein 1 Using Antisense-Transfer Mouse

To clarify the importance of FROUNT protein 1 at the individual animal level, an antisense-transfer mouse was constructed in the following method and the phenotype of the mouse was observed.

(1) Construction of Antisense-Transfer Mouse

Figure 18:
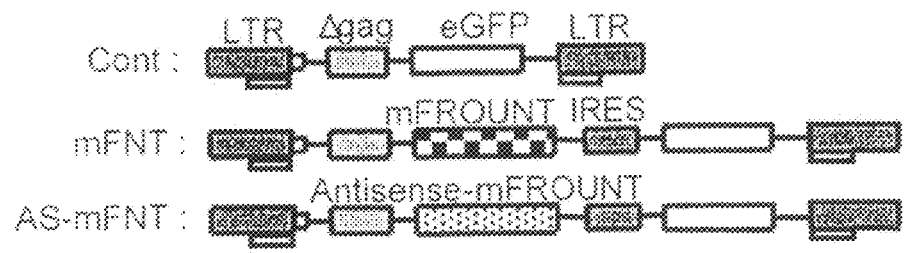
FIG. 18 is a schematic model of a retrovirus vector pEG-FPMY which is a mouse FROUNT protein vector.

Using the isolated mouse FROUNT gene as described above as a template, a fragment was amplified by the PCR method with the use of a 5'-primer: 5'GCGGATCCATG-GAGGAGCTCGATGGCG AGCC3' (SEQ ID NO:59) and a 3'-primer: 5'GCGGATCCTCAGGAA CCTTCCAGT-GAGC3' (SEQ ID NO:60) and treated with BamHI. Next, it was inserted into pEGFPMY to thereby construct antisense and sense-expression retrovirus vectors (FIG. 18). FIG. 18 shows schematic models of the retrovirus vectors pEGFPMY, wherein Cont stands for a control (empty) vector; mFNT stands for a mouse FROUNT protein expression vector; AS-mFNT stands for a mouse FROUNT protein antisense expression vector; LTR stands for a long terminal repeat; gag stands for a structural protein; eGFP stands for a green fluorescent protein; and IRES stands for a ribosomal entry site. These vectors were transferred into virus packaging cells BOSC23 (ATCC, CRL11554). 48 hours after the transformation, the cell supernatant containing the recombinant retroviruses was collected. Then bone marrow precursor cells purified from mouse bone marrow cells with the use of an MACS system (Milteny Biotech) were infected with these retroviruses by the centrifugation method. Cells infected with each virus vector alone were separated and purified to a purity of 98% or higher by using a cell sorter system with the expression of EGFP encoded by the virus vector as an indication. After irradiating recipient G57BL6 mice at lethal radiation dose (11 Gy), the virus vector-infected cells were intravenously administered. 3 months after the transfer, 50 µl of peripheral blood was collected from the eye ground and the reconstruction ratio of the bone marrow cells was measured with a fluorocytometer. As a result, the expression of EGFP was confirmed in 70 to 90% of leukocytes, which suggested that the bone marrow-origin cells had been almost replaced by the cells infected with each vector. Using these mice 3 to 4 months after the transfer, the following experiment was carried out.

(2) Cell Migration Experiment Using Thioglycolate

Figure 19:
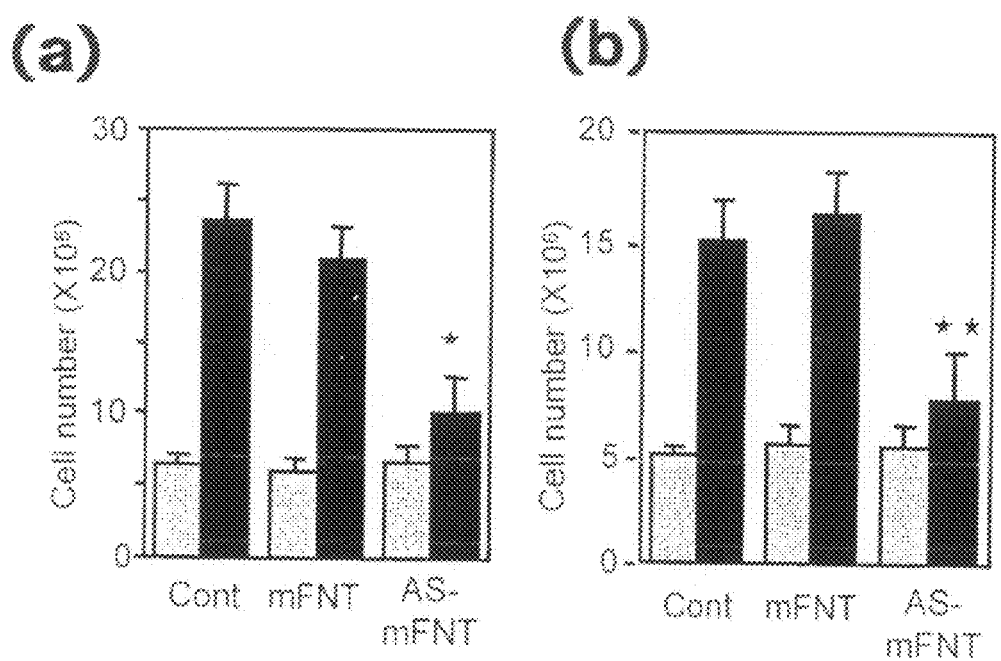
FIG. 19 shows the results of a chemotaxis experiment in mice stimulated with thioglycolate.

In peritonitis models induced by intraperitoneally (I.P.) injecting thioglycolate into mice, a CCR2-knockout mouse shows largely reduced macrophage infiltration after the intraperitoneal administration compared with a normal mouse. It is thus known the macrophage infiltration is mediated by CCR2. Using the peritonitis models, the CCR2-mediated macrophage infiltrating ability of the FROUNT antisense-transfer mouse (AS-mFNT mouse) as described above was compared with those of the control mouse (Cont mouse) and the sense-transfer model (mFNT mouse) to thereby analyze the function of FROUNT protein in individual mice. First, thioglycolate (Difco) was dissolved in PBS at a concentration of 4% and the obtained solution was intraperitoneally administered in 1.5 ml portions to the gene-transfer mice as described above. After 72 hours, 5 ml of PBS cooled to 4° C. was further intraperitoneally administered and each animal was well massaged. Then intraperitoneal cells were collected and the cell counts were compared. As a result, it was confirmed that the AS-mFNT mouse showed a remarkable decrease in intraperitoneal cell count compared with the Cont mouse and the mFNT mouse. However, no abnormality in intraperitoneal cell count was observed in these mice before the stimulation with thioglycolate. Among the intraperitoneal cells thus collected, cells expressing a macrophage-specific surface marker F4/80 or MOMA-2 were immunostained with a specific antibody and counted with a fluocytometer. As a result, macrophage count was obviously lowered in the As-mFNT mouse. As the results of immunostaining with the use of mouse spleen tissue sections, it was confirmed that mouse FROUNT protein 1 was also expressed in cells expressing F4/80 and MOMA-2. These results suggest that, even in a mouse showing no abnormality in the CCR2 expression, the CCR2-dependent signal transduction system was inhibited and the infiltration ability of macrophages was lowered by reducing FROUNT protein, indicating the importance of FROUNT protein 1 in an individual mouse (FIG. 19). FIG. 19 shows the results of a chemotaxis experiment with the use of thioglycolate on the intraperitoneal cells (a) and the macrophages (b) of each virus vector-transfer mouse, wherein each open bar shows a cell count without stimulation while each solid bar shows a cell count upon thioglycolate stimulation.

Example 10

Plasmid-Containing Liposome Preparation (1) Construction of Plasmid

A FROUNT protein expression vector was prepared by inserting the cDNA represented by SEQ ID NO:19 between the EcoRI and NotI sites of a pUC-SRα expression vector (FEBS 333:61-66 (1993)). In this plasmid vector, the transcription of the FROUNT protein cDNA was controlled by the SRα promoter (Nature 342:440-443 (1989)).

(2) Production of Liposome Preparation

Tetrahydrofuran was mixed with phosphatidylserine, phosphatidylcholine and cholesterol at a weight ratio of 1:4:8:2. After distilling off the tetrahydrofuran on a rotary evaporator, the lipid mixture (10 mg) was deposited on the container wall. 96 µg of HMG 1 nucleic acid (high mobility group 1 nuclear protein) purified from bovine thymus was mixed with a BBS solution (20 µl) of the FROUNT protein DNA plasmid (300 µg) at 20° C. for 1 hour and then the resultant mixture was added to the above-described lipids. The obtained liposome-DNA-HMG 1 complex suspension was mixed with a portex, ultrasonicated for 3 seconds and then stirred for 30 minutes. Purified HVJ (Z strain) was inactivated by UV irradiation (110 erg/mm² sec) for 3 minutes immediately before using. To the liposome suspension (0.5 ml, containing 10 mg of lipids) obtained above, BBS was added to give a total volume of 4 ml. The obtained mixture was incubated at 4° C. for 10 minutes and then gently stirred at 37° C. for 30 minutes. Unfused liposomes were removed from the HJV-liposomes by the sucrose density gradient centrifugation method. Thus, HVJ-liposomes containing the FROUNT protein expression vector (containing 10 g/ml of FROUNT protein expression vector) was obtained from the upper layer of sucrose density gradient. In the same manner, a liposome preparation containing the antisense RNA and a liposome preparation containing DNA producing the antisense RNA can be obtained. Such a preparation is injected into a target site via an injection needle.

INDUSTRIAL APPLICABILITY

The protein according to the present invention, which plays a different role from a G protein in the intracellular signal transduction mechanisms of the G protein-coupled receptors CCR2 and CCR5, indicates the presence of a new mechanism participating in the intracellular signal transduction together with the G protein. That is to say, there is a possibility that these new mechanisms in the CCR2 system and the CCR5 system would affect the efficacy and side effects of drugs in addition to the intracellular signal transduction mechanism having been attracted public attention concerning the relationships among receptors, G proteins and effectors so far. Therefore, the discovery of the protein according to the present invention and DNA encoding the same brings about the provision of novel medical targets. Namely, the present invention provides new approaches to the treatment, prevention, diagnosis, etc. of diseases in which signal transduction pathways (monocyte and macrophage chemotaxis, calcium mobilization, receptor clusterization, etc.) participate, as well as clarification of the mechanisms thereof. In practice, it is considered that functions of monocytes and macrophages are affected by several factors (for example, insufficiency in a receptor, insufficiency in a G protein, etc.). Owing to the clarification of the presence of a novel protein (FROUNT protein) relating to these functions by the present inventors, it becomes possible to diversify approaches to diseases in which monocytes and macrophages participate.

By combining the phenomenon of the association of a FROUNT protein with the C-terminal domain of a receptor with a labeling agent as in the present invention, clusterization and colocalization can be visualized. Namely, a biological phenomenon called internalization based on the interaction between a cell receptor and an agonist can be more easily grasped, observed and detected directly with eye. Moreover, it is expected that various cells transformed by the procedure according to the present invention are widely applicable and usable in various fields in, for example, easily detecting cytotoxic substances, detecting environmental pollutants, examining cytotoxicity of drugs and so on.

CITED DOCUMENTS

1. Murphy, P. M. et al. International union of pharmacology. XXII. Nomenclature for chemokine receptors. *Pharmacol Rev* 52, 145-76. (2000).
2. Baggiolini, M. Chemokines and leukocyte traffic. *Nature* 392, 565-8. (1998).
3. Condliffe, A. M. & Hawkins, P. T. Cell biology. Moving in mysterious ways. *Nature* 404, 135, 137. (2000).
4. Gerard, C. & Rollins, B. J. Chemokines and disease. *Nat Immunol* 2, 108-15. (2001).
5. Yoshimura, T. et al. Purification of a human monocyte-derived neutrophil chemotactic factor that has peptide sequence similarity to other host defense cytokines. *Proc Natl Acad Sci USA* 84, 9233-7. (1987).
6. Walz, A., Peveri, P., Aschauer, H. & Baggiolini, M. Purification and amino acid sequencing of NAF, a novel neutrophil-activating factor produced by monocytes. *Biochem Biophys Res Commun* 149, 755-61. (1987).
7. Matsushima, K., Larsen, C. G., DuBois, G. C. & Oppenheim, J. J. Purification and characterization of a novel monocyte chemotactic and activating factor produced by a human myelomonocytic cell line. *J Exp Med* 169, 1485-90. (1989).
8. Yoshimura, T. et al. Purification and amino acid analysis of two human glioma-derived monocyte chemoattractants. *J Exp Med* 169, 1449-59. (1989).
9. Howard, O. M., Oppenheim, J. J. & Wang, J. M. Chemokines as molecular targets for therapeutic intervention. *J Clin Immunol* 19, 280-92. (1999).
10. Sallusto, F., Mackay, C. R. & Lanzavecchia, A. The role of chemokine receptors in primary, effector, and memory immune responses. *Annu Rev Immunol* 18, 593-620 (2000).
11. Kunkel, S. L., Strieter, R. M., Lindley, I. J. & Westwick, J. Chemokines: new ligands, receptors and activities. *Immunol Today* 16, 559-61. (1995).
12. Charo, I. F. et al. Molecular cloning and functional expression of two monocyte chemoattractant protein 1 receptors reveals alternative splicing of the carboxyl-terminal tails. *Proc Natl Acad Sci USA* 91, 2752-6. (1994).
13. Boring, L., Gosling, J., Cleary, M. & Charo, I. F. Decreased lesion formation in CCR2-/- mice reveals a role for chemokines in the initiation of atherosclerosis. *Nature* 394, 894-7. (1998).
14. Gu, L. et al. Absence of monocyte chemoattractant protein-1 reduces atherosclerosis in low density lipoprotein receptor-deficient mice. *Mol Cell* 2, 275-81. (1998).
15. Wada, T. et al. Intervention of crescentic glomerulonephritis by antibodies to monocyte chemotactic and activating factor (MCAF/MCP-1). *Faseb J* 10, 1418-25. (1996).
16. Fife, B. T., Huffnagle, G. B., Kuziel, W. A. & Karpus, W. J. CC chemokine receptor 2 is critical for induction of experimental autoimmune encephalomyelitis. *J Exp Med* 192, 899-905. (2000).
17. Izikson, L., Klein, R. S., Charo, I. F., Weiner, H. L. & Luster, A. D. Resistance to experimental autoimmune encephalomyelitis in mice lacking the CC chemokine receptor (CCR)2. *J Exp Med* 192, 1075-80. (2000).
18. Boring, L. et al. Impaired monocyte migration and reduced type 1 (Th1) cytokine responses in C-C chemokine receptor 2 knockout mice. *J Clin Invest* 100, 2552-61. (1997).
19. Kurihara, T., Warr, G., Loy, J. & Bravo, R. Defects in macrophage recruitment and host defense in mice lacking the CCR2 chemokine receptor. *J Exp Med* 186, 1757-62. (1997).
20. Kuziel, W. A. et al. Severe reduction in leukocyte adhesion and monocyte extravasation in mice deficient in CC chemokine receptor 2. *Proc Natl Acad Sci USA* 94, 12053-8. (1997).
21. Lu, B. et al. Abnormalities in monocyte recruitment and cytokine expression in monocyte chemoattractant protein 1-deficient mice. *J Exp Med* 187, 601-8. (1998).

22. Maghazachi, A. A. Intracellular signaling events at the leading edge of migrating cells. *Int J Biochem Cell Biol* 32, 931-43. (2000).
23. Parent, C. A. & Devreotes, P. N. A cell's sense of direction. *Science* 284, 765-70. (1999).
24. Penn, R. B., Pronin, A. N. & Benovic, J. L. Regulation of G protein-coupled receptor kinases. *Trends Cardiovasc Med* 10, 81-9. (2000).
25. Mellado, M., Rodriguez-Frade, J. M., Manes, S. & Martinez, A. C. Chemokine signaling and functional responses: the role of receptor dimerization and TK pathway activation. *Annu Rev Immunol* 19, 397-421 (2001).
26. Hall, R. A., Premont, R. T. & Lefkowitz, R. J. Heptahelical receptor signaling: beyond the G protein paradigm. *J Cell Biol* 145, 927-32. (1999).
27. Ben-Baruch, A. et al. Interleukin-8 receptor beta. The role of the carboxyl terminus in signal transduction. *J Biol Chem* 270, 9121-8. (1995).
28. Arai, H., Monteclaro, F. S., Tsou, C. L., Franci, C. & Charo, I. F. Dissociation of chemotaxis from agonist-induced receptor internalization in a lymphocyte cell line transfected with CCR2B. Evidence that directed migration does not require rapid modulation of signaling at the receptor level. *J Biol Chem* 272, 25037-42. (1997).
29. Kim, J. Y. et al. Phosphorylation of chemoattractant receptors is not essential for chemotaxis or termination of G-protein-mediated responses. *J Biol Chem* 272, 27313-8. (1997).
30. Hsu, M. H., Chiang, S. C., Ye, R. D. & Prossnitz, E. R. Phosphorylation of the N-formyl peptide receptor is required for receptor internalization but not chemotaxis. *J Biol Chem* 272, 29426-9. (1997).
31. Richardson, R. M., Ali, H., Pridgen, B. C., Haribabu, B. & Snyderman, R. Multiple signaling pathways of human interleukin-8 receptor A. Independent regulation by phosphorylation. *J Biol Chem* 273, 10690-5. (1998).
32. Kraft, K. et al. Characterization of sequence determinants within the carboxyl-terminal domain of chemokine receptor CCR5 that regulate signaling and receptor internalization. *J Biol Chem* 276, 34408-18. (2001).
33. Tsao, P. I. & von Zastrow, M. Diversity and specificity in the regulated endocytic membrane trafficking of G-protein-coupled receptors. *Pharmacol Ther* 89, 139-47. (2001).
34. Ferguson, S. S. Evolving concepts in G protein-coupled receptor endocytosis: the role in receptor desensitization and signaling. *Pharmacol Rev* 53, 1-24. (2001).
35. Gosling, J. et al. Molecular uncoupling of C-C chemokine receptor 5-induced chemotaxis and signal transduction from HIV-1 coreceptor activity. *Proc Natl Acad Sci USA* 94, 5061-6. (1997).
36. Sambrano, G. R. & Coughlin, S. R. The carboxyl tail of protease-activated receptor-1 is required for chemotaxis. Correlation of signal termination and directional migration. *J Biol Chem* 274, 20178-84. (1999).
37. Le Gouill, C. et al. Selective modulation of wild type receptor functions by mutants of G-protein-coupled receptors. *J Biol Chem* 274, 12548-54. (1999).
38. Shibata, T., Suzuki, C., Ohnishi, J., Murakami, K. & Miyazaki, H. Identification of regions in the human angiotensin II receptor type 1 responsible for Gi and Gq coupling by mutagenesis study. *Biochem Biophys Res Commun* 218, 383-9. (1996).
39. O'Connor, V. et al. Calmodulin dependence of presynaptic metabotropic glutamate receptor signaling. *Science* 286, 1180-4. (1999).
40. Arai, H., Tsou, C. L. & Charo, I. F. Chemotaxis in a lymphocyte cell line transfected with C-C chemokine receptor 2B: evidence that directed migration is mediated by betagamma dimers released by activation of Galphai-coupled receptors. *Proc Natl Acad Sci USA* 94, 14495-9. (1997).
41. Jin, T., Zhang, N., Long, Y., Parent, C. A. & Devreotes, P. N. Localization of the G protein betagamma complex in living cells during chemotaxis. *Science* 287, 1034-6. (2000).
42. Parent, C. A., Blacklock, B. J., Froehlich, W. M., Murphy, D. B. & Devreotes, P. N. G protein signaling events are activated at the leading edge of chemotactic cells. *Cell* 95, 81-91. (1998).
43. Fukui, Y. et al. Haematopoietic cell-specific CDM family protein DOCK2 is essential for lymphocyte migration. *Nature* 412, 826-31. (2001).
44. Murai, M. et al. Active participation of CCR5(+)CD8(+) T lymphocytes in the pathogenesis of liver injury in graft-versus-host disease. *J Clin Invest* 104, 49-57. (1999).
45. Onai, N. et al. Impairment of lymphopoiesis and myelopoiesis in mice reconstituted with bone marrow-hematopoietic progenitor cells expressing SDF-1-intrakine. *Blood* 96, 2074-80. (2000).

The invention claimed is:

1. A method of identifying an inhibitor of an agonist to receptor(s) CCR2 and/or CCR5 comprising:

forcibly expressing a marker-labeled FROUNT protein having an amino acid sequence represented by SEQ ID NO:2 selected in a cell having the receptor(s) CCR2 and/or CCR5 or expressing the same;

treating the cell with an agonist to CCR2 and/or CCR5 and a candidate for the agonist inhibitor;

observing whether or not the clusterization of the receptor(s) is induced; and judging whether or not the candidate has an inhibitory effect on the agonist.

2. The identification method as claimed in claim 1 wherein the marker-labeled FROUNT protein is a FROUNT protein fused with a visible color fluorescent protein.

3. The identification method as claimed in claim 2 wherein the visible color fluorescent protein is a green fluorescent protein, a red fluorescent protein, a blue fluorescent protein or a yellow fluorescent protein.

4. The method of identifying an inhibitor as claimed in claim 1 wherein the identification is made depending on a color change as an indication by using a cell wherein both of the receptor(s) CCR2 and/or CCR5 and FROUNT protein are labeled with visible color markers being different from each other in color.

* * * * *

SEQUENCE LISTING

```
<160> NUMBER OF SEQ ID NOS: 69

<210> SEQ ID NO 1
<211> LENGTH: 1971
<212> TYPE: DNA
<213> ORGANISM: Homo sapiens
<220> FEATURE:
<221> NAME/KEY: CDS
<222> LOCATION: (1)..(1971)

<400> SEQUENCE: 1 atg gag gag ctc gat ggc gag cca aca gtc act ttg att cca ggc gtg      48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg      96
```

```
                                                    -continued

Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg       144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac       192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg       240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct       288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt       336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat       384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc       432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc       480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag       528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa       576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg       624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc       672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg       720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg       768
Pro Ile Leu Ser Pro Gly Asn Thr Gln Thr Leu Thr Glu Leu Glu Leu
                245                 250                 255 aag tgg cag cac tgg cac gag gaa tgt gag cgg tac ctc cag gac agc       816
Lys Trp Gln His Trp His Glu Glu Cys Glu Arg Tyr Leu Gln Asp Ser
            260                 265                 270 aca ttc gcc acc agc cct cac ctg gag tct ctc ttg aag att atg ctg       864
Thr Phe Ala Thr Ser Pro His Leu Glu Ser Leu Leu Lys Ile Met Leu
        275                 280                 285 gga gac gaa gct gcc ttg tta gag cag aag gaa ctt ctg agt aat tgg       912
Gly Asp Glu Ala Ala Leu Leu Glu Gln Lys Glu Leu Leu Ser Asn Trp
    290                 295                 300 tat cat ttc cta gtg act cgg ctc ttg tac tcc aat ccc aca gta aaa       960
Tyr His Phe Leu Val Thr Arg Leu Leu Tyr Ser Asn Pro Thr Val Lys
305                 310                 315                 320 ccc att gat ctg cac tac tat gcc cag tcc agc ctg gac ctg ttt ctg      1008
Pro Ile Asp Leu His Tyr Tyr Ala Gln Ser Ser Leu Asp Leu Phe Leu
                325                 330                 335
```

-continued

```
gga ggt gag agc agc cca gaa ccc ctg gac aac atc ttg ttg gca gcc    1056
Gly Gly Glu Ser Ser Pro Glu Pro Leu Asp Asn Ile Leu Leu Ala Ala
            340                 345                 350 ttt gag ttt gac atc cat caa gta atc aaa gag tgc agc atc gcc ctg    1104
Phe Glu Phe Asp Ile His Gln Val Ile Lys Glu Cys Ser Ile Ala Leu
        355                 360                 365 agc aac tgg tgg ttt gtg gcc cac ctg aca gac ctg ctg gac cac tgc    1152
Ser Asn Trp Trp Phe Val Ala His Leu Thr Asp Leu Leu Asp His Cys
    370                 375                 380 aag ctc ctc cag tca cac aac ctc tat ttc ggt tcc aac atg aga gag    1200
Lys Leu Leu Gln Ser His Asn Leu Tyr Phe Gly Ser Asn Met Arg Glu
385                 390                 395                 400 ttc ctc ctg ctg gag tac gcc tcg gga ctg ttt gct cat ccc agc ctg    1248
Phe Leu Leu Leu Glu Tyr Ala Ser Gly Leu Phe Ala His Pro Ser Leu
                405                 410                 415 tgg cag ctg ggg gtc gat tac ttt gat tac tgc ccc gag ctg ggc cga    1296
Trp Gln Leu Gly Val Asp Tyr Phe Asp Tyr Cys Pro Glu Leu Gly Arg
            420                 425                 430 gtc tcc ctg gag ctg cac att gag cgg ata cct ctg aac acc gag cag    1344
Val Ser Leu Glu Leu His Ile Glu Arg Ile Pro Leu Asn Thr Glu Gln
        435                 440                 445 aaa gcc ctg aag gtg ctg cgg atc tgt gag cag cgg cag atg act gaa    1392
Lys Ala Leu Lys Val Leu Arg Ile Cys Glu Gln Arg Gln Met Thr Glu
    450                 455                 460 caa gtt cgc agc att tgt aag atc tta gcc atg aaa gcc gtc cgc aac    1440
Gln Val Arg Ser Ile Cys Lys Ile Leu Ala Met Lys Ala Val Arg Asn
465                 470                 475                 480 aat cgc ctg ggt tct gcc ctc tct tgg agc atc cgt gct aag gat gcc    1488
Asn Arg Leu Gly Ser Ala Leu Ser Trp Ser Ile Arg Ala Lys Asp Ala
                485                 490                 495 gcc ttt gcc acg ctc gtg tca gac agg ttc ctc agg gat tac tgt gag    1536
Ala Phe Ala Thr Leu Val Ser Asp Arg Phe Leu Arg Asp Tyr Cys Glu
            500                 505                 510 cga ggc tgc ttt tct gat ttg gat ctc att gac aac ctg ggg cca gcc    1584
Arg Gly Cys Phe Ser Asp Leu Asp Leu Ile Asp Asn Leu Gly Pro Ala
        515                 520                 525 atg atg ctc agt gac cga ctg aca ttc ctg gga aag tat cgc gag ttc    1632
Met Met Leu Ser Asp Arg Leu Thr Phe Leu Gly Lys Tyr Arg Glu Phe
    530                 535                 540 cac cgt atg tac ggg gag aag cgt ttt gcc gac gca gct tct ctc ctt    1680
His Arg Met Tyr Gly Glu Lys Arg Phe Ala Asp Ala Ala Ser Leu Leu
545                 550                 555                 560 ctg tcc ttg atg acg tct cgg att gcc cct cgg tct ttc tgg atg act    1728
Leu Ser Leu Met Thr Ser Arg Ile Ala Pro Arg Ser Phe Trp Met Thr
                565                 570                 575 ctg ctg aca gat gcc ttg ccc ctt ttg gaa cag aaa cag gtg att ttc    1776
Leu Leu Thr Asp Ala Leu Pro Leu Leu Glu Gln Lys Gln Val Ile Phe
            580                 585                 590 tca gca gaa cag act tat gag ttg atg cgg tgt ctg gag gac ttg acg    1824
Ser Ala Glu Gln Thr Tyr Glu Leu Met Arg Cys Leu Glu Asp Leu Thr
        595                 600                 605 tca aga aga cct gtg cat gga gaa tct gat acc gag cag ctc cag gat    1872
Ser Arg Arg Pro Val His Gly Glu Ser Asp Thr Glu Gln Leu Gln Asp
    610                 615                 620 gat gac ata gag acc acc aag gtg gaa atg ctg aga ctt tct ctg gca    1920
Asp Asp Ile Glu Thr Thr Lys Val Glu Met Leu Arg Leu Ser Leu Ala
625                 630                 635                 640 cga aat ctt gct cgg gca att ata aga gaa ggc tca ctg gaa ggt tcc    1968
Arg Asn Leu Ala Arg Ala Ile Ile Arg Glu Gly Ser Leu Glu Gly Ser
                645                 650                 655
``` tga                                                                  1971

<210> SEQ ID NO 2
<211> LENGTH: 656
<212> TYPE: PRT
<213> ORGANISM: Homo sapiens

<400> SEQUENCE: 2

Met Glu Glu Leu Asp Gly Glu Pro Thr Val Thr Leu Ile Pro Gly Val
 1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
        275                 280                 285

Gly Asp Glu Ala Ala Leu Leu Glu Gln Lys Glu Leu Leu Ser Asn Trp
    290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Ser Ser Leu Asp Leu Phe Leu
                325                 330                 335

Gly Gly Glu Ser Ser Pro Glu Pro Leu Asp Asn Ile Leu Leu Ala Ala
            340                 345                 350

Phe Glu Phe Asp Ile His Gln Val Ile Lys Glu Cys Ser Ile Ala Leu
        355                 360                 365

```
Ser Asn Trp Trp Phe Val Ala His Leu Thr Asp Leu Leu Asp His Cys
    370                 375                 380

Lys Leu Leu Gln Ser His Asn Leu Tyr Phe Gly Ser Asn Met Arg Glu
385                 390                 395                 400

Phe Leu Leu Leu Glu Tyr Ala Ser Gly Leu Phe Ala His Pro Ser Leu
                405                 410                 415

Trp Gln Leu Gly Val Asp Tyr Phe Asp Tyr Cys Pro Glu Leu Gly Arg
                420                 425                 430

Val Ser Leu Glu Leu His Ile Glu Arg Ile Pro Leu Asn Thr Glu Gln
            435                 440                 445

Lys Ala Leu Lys Val Leu Arg Ile Cys Glu Gln Arg Gln Met Thr Glu
    450                 455                 460

Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
                485                 490                 495

Ala Phe Ala Thr Leu Val Ser Asp Arg Phe Leu Arg Asp Tyr Cys Glu
                500                 505                 510

Arg Gly Cys Phe Ser Asp Leu Asp Leu Ile Asp Asn Leu Gly Pro Ala
            515                 520                 525

Met Met Leu Ser Asp Arg Leu Thr Phe Leu Gly Lys Tyr Arg Glu Phe
    530                 535                 540

His Arg Met Tyr Gly Glu Lys Arg Phe Ala Asp Ala Ala Ser Leu Leu
545                 550                 555                 560

Leu Ser Leu Met Thr Ser Arg Ile Ala Pro Arg Ser Phe Trp Met Thr
                565                 570                 575

Leu Leu Thr Asp Ala Leu Pro Leu Leu Glu Gln Lys Gln Val Ile Phe
            580                 585                 590

Ser Ala Glu Gln Thr Tyr Glu Leu Met Arg Cys Leu Glu Asp Leu Thr
    595                 600                 605

Ser Arg Arg Pro Val His Gly Glu Ser Asp Thr Glu Gln Leu Gln Asp
610                 615                 620

Asp Asp Ile Glu Thr Thr Lys Val Glu Met Leu Arg Leu Ser Leu Ala
625                 630                 635                 640

Arg Asn Leu Ala Arg Ala Ile Ile Arg Glu Gly Ser Leu Glu Gly Ser
                645                 650                 655

<210> SEQ ID NO 3
<211> LENGTH: 1836
<212> TYPE: DNA
<213> ORGANISM: Homo sapiens
<220> FEATURE:
<221> NAME/KEY: CDS
<222> LOCATION: (1)..(1836)

<400> SEQUENCE: 3 atg gag gag ctc gat ggc gag cca aca gtc act ttg att cca ggc gtg      48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
```

```
            Pro Ser Cys Pro Phe Ile Tyr Ile Ile Arg Lys Asp Val Asp Val Tyr
                 50              55                  60 tct caa atc ttg aga aaa ctc ttc aat gaa tcc cat gga atc ttt ctg        240
Ser Gln Ile Leu Arg Lys Leu Phe Asn Glu Ser His Gly Ile Phe Leu
 65              70                  75                  80 ggc ctc cag aga att gac gaa gag ttg act gga aaa tcc aga aaa tct        288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt        336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat        384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc        432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc        480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag        528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa        576
Val Asp Ser Leu Ser Ala Asp Val Leu Gly Ser Glu Asn Pro Ser Lys
            180                 185                 190 cat gac agc ttc tgg aac ttg cct ggg aac acc cag aca ctg aca gag        624
His Asp Ser Phe Trp Asn Leu Pro Gly Asn Thr Gln Thr Leu Thr Glu
        195                 200                 205 ctg gag ctg aag tgg cag cac tgg cac gag gaa tgt gag cgg tac ctc        672
Leu Glu Leu Lys Trp Gln His Trp His Glu Glu Cys Glu Arg Tyr Leu
    210                 215                 220 cag gac agc aca ttc gcc acc agc cct cac ctg gag tct ctc ttg aag        720
Gln Asp Ser Thr Phe Ala Thr Ser Pro His Leu Glu Ser Leu Leu Lys
225                 230                 235                 240 att atg ctg gga gac gaa gct gcc ttg tta gag cag aag gaa ctt ctg        768
Ile Met Leu Gly Asp Glu Ala Ala Leu Leu Glu Gln Lys Glu Leu Leu
                245                 250                 255 agt aat tgg tat cat ttc cta gtg act cgg ctc ttg tac tcc aat ccc        816
Ser Asn Trp Tyr His Phe Leu Val Thr Arg Leu Leu Tyr Ser Asn Pro
            260                 265                 270 aca gta aaa ccc att gat ctg cac tac tat gcc cag tcc agc ctg gac        864
Thr Val Lys Pro Ile Asp Leu His Tyr Tyr Ala Gln Ser Ser Leu Asp
        275                 280                 285 ctg ttt ctg gga ggt gag agc agc cca gaa ccc ctg gac aac atc ttg        912
Leu Phe Leu Gly Gly Glu Ser Ser Pro Glu Pro Leu Asp Asn Ile Leu
    290                 295                 300 ttg gca gcc ttt gag ttt gac atc cat caa gta atc aaa gag tgc agc        960
Leu Ala Ala Phe Glu Phe Asp Ile His Gln Val Ile Lys Glu Cys Ser
305                 310                 315                 320 atc gcc ctg agc aac tgg tgg ttt gtg gcc cac ctg aca gac ctg ctg       1008
Ile Ala Leu Ser Asn Trp Trp Phe Val Ala His Leu Thr Asp Leu Leu
                325                 330                 335 gac cac tgc aag ctc ctc cag tca cac aac ctc tat ttc ggt tcc aac       1056
Asp His Cys Lys Leu Leu Gln Ser His Asn Leu Tyr Phe Gly Ser Asn
            340                 345                 350 atg aga gag ttc ctc ctg ctg gag tac gcc tcg gga ctg ttt gct cat       1104
Met Arg Glu Phe Leu Leu Leu Glu Tyr Ala Ser Gly Leu Phe Ala His
        355                 360                 365
```

```
ccc agc ctg tgg cag ctg ggg gtc gat tac ttt gat tac tgc ccc gag    1152
Pro Ser Leu Trp Gln Leu Gly Val Asp Tyr Phe Asp Tyr Cys Pro Glu
    370                 375                 380 ctg ggc cga gtc tcc ctg gag ctg cac att gag cgg ata cct ctg aac    1200
Leu Gly Arg Val Ser Leu Glu Leu His Ile Glu Arg Ile Pro Leu Asn
385                 390                 395                 400 acc gag cag aaa gcc ctg aag gtg ctg cgg atc tgt gag cag cgg cag    1248
Thr Glu Gln Lys Ala Leu Lys Val Leu Arg Ile Cys Glu Gln Arg Gln
                405                 410                 415 atg act gaa caa gtt cgc agc att tgt aag atc tta gcc atg aaa gcc    1296
Met Thr Glu Gln Val Arg Ser Ile Cys Lys Ile Leu Ala Met Lys Ala
            420                 425                 430 gtc cgc aac aat cgc ctg ggt tct gcc ctc tct tgg agc atc cgt gct    1344
Val Arg Asn Asn Arg Leu Gly Ser Ala Leu Ser Trp Ser Ile Arg Ala
        435                 440                 445 aag gat gcc gcc ttt gcc acg ctc gtg tca gac agg ttc ctc agg gat    1392
Lys Asp Ala Ala Phe Ala Thr Leu Val Ser Asp Arg Phe Leu Arg Asp
    450                 455                 460 tac tgt gag cga ggc tgc ttt tct gat ttg gat ctc att gac aac ctg    1440
Tyr Cys Glu Arg Gly Cys Phe Ser Asp Leu Asp Leu Ile Asp Asn Leu
465                 470                 475                 480 ggg cca gcc atg atg ctc agt gac cga ctg aca ttc ctg gga aag tat    1488
Gly Pro Ala Met Met Leu Ser Asp Arg Leu Thr Phe Leu Gly Lys Tyr
                485                 490                 495 cgc gag ttc cac cgt atg tac ggg gag aag cgt ttt gcc gac gca gct    1536
Arg Glu Phe His Arg Met Tyr Gly Glu Lys Arg Phe Ala Asp Ala Ala
            500                 505                 510 tct ctc ctt ctg tcc ttg atg acg tct cgg att gcc cct cgg tct ttc    1584
Ser Leu Leu Leu Ser Leu Met Thr Ser Arg Ile Ala Pro Arg Ser Phe
        515                 520                 525 tgg atg act ctg ctg aca gat gcc ttg ccc ctt ttg gaa cag aaa cag    1632
Trp Met Thr Leu Leu Thr Asp Ala Leu Pro Leu Leu Glu Gln Lys Gln
    530                 535                 540 gtg att ttc tca gca gaa cag act tat gag ttg atg cgg tgt ctg gag    1680
Val Ile Phe Ser Ala Glu Gln Thr Tyr Glu Leu Met Arg Cys Leu Glu
545                 550                 555                 560 gac ttg acg tca aga aga cct gtg cat gga gaa tct gat acc gag cag    1728
Asp Leu Thr Ser Arg Arg Pro Val His Gly Glu Ser Asp Thr Glu Gln
                565                 570                 575 ctc cag gat gat gac ata gag acc acc aag gtg gaa atg ctg aga ctt    1776
Leu Gln Asp Asp Asp Ile Glu Thr Thr Lys Val Glu Met Leu Arg Leu
            580                 585                 590 tct ctg gca cga aat ctt gct cgg gca att ata aga gaa ggc tca ctg    1824
Ser Leu Ala Arg Asn Leu Ala Arg Ala Ile Ile Arg Glu Gly Ser Leu
        595                 600                 605 gaa ggt tcc tga                                                    1836
Glu Gly Ser
    610

<210> SEQ ID NO 4
<211> LENGTH: 611
<212> TYPE: PRT
<213> ORGANISM: Homo sapiens

<400> SEQUENCE: 4

Met Glu Glu Leu Asp Gly Glu Pro Thr Val Thr Leu Ile Pro Gly Val
 1               5                  10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
```

```
                35                  40                  45
Pro Ser Cys Pro Phe Ile Tyr Ile Ile Arg Lys Asp Val Asp Val Tyr
        50                  55                  60

Ser Gln Ile Leu Arg Lys Leu Phe Asn Glu Ser His Gly Ile Phe Leu
65                  70                  75                  80

Gly Leu Gln Arg Ile Asp Glu Leu Thr Gly Lys Ser Arg Lys Ser
            85                  90                  95

Gln Leu Val Arg Val Ser Lys Asn Tyr Arg Ser Val Ile Arg Ala Cys
               100                 105                 110

Met Glu Glu Met His Gln Val Ala Ile Ala Ala Lys Asp Pro Ala Asn
                115                 120                 125

Gly Arg Gln Phe Ser Ser Gln Val Ser Ile Leu Ser Ala Met Glu Leu
            130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Pro Gly Asn Thr Gln Thr Leu Thr Glu
            195                 200                 205

Leu Glu Leu Lys Trp Gln His Trp His Glu Glu Cys Glu Arg Tyr Leu
        210                 215                 220

Gln Asp Ser Thr Phe Ala Thr Ser Pro His Leu Glu Ser Leu Leu Lys
225                 230                 235                 240

Ile Met Leu Gly Asp Glu Ala Ala Leu Leu Glu Gln Lys Glu Leu Leu
                245                 250                 255

Ser Asn Trp Tyr His Phe Leu Val Thr Arg Leu Leu Tyr Ser Asn Pro
            260                 265                 270

Thr Val Lys Pro Ile Asp Leu His Tyr Tyr Ala Gln Ser Ser Leu Asp
            275                 280                 285

Leu Phe Leu Gly Gly Glu Ser Ser Pro Glu Pro Leu Asp Asn Ile Leu
        290                 295                 300

Leu Ala Ala Phe Glu Phe Asp Ile His Gln Val Ile Lys Glu Cys Ser
305                 310                 315                 320

Ile Ala Leu Ser Asn Trp Trp Phe Val Ala His Leu Thr Asp Leu Leu
                325                 330                 335

Asp His Cys Lys Leu Leu Gln Ser His Asn Leu Tyr Phe Gly Ser Asn
            340                 345                 350

Met Arg Glu Phe Leu Leu Leu Glu Tyr Ala Ser Gly Leu Phe Ala His
            355                 360                 365

Pro Ser Leu Trp Gln Leu Gly Val Asp Tyr Phe Asp Tyr Cys Pro Glu
        370                 375                 380

Leu Gly Arg Val Ser Leu Glu Leu His Ile Glu Arg Ile Pro Leu Asn
385                 390                 395                 400

Thr Glu Gln Lys Ala Leu Lys Val Leu Arg Ile Cys Glu Gln Arg Gln
                405                 410                 415

Met Thr Glu Gln Val Arg Ser Ile Cys Lys Ile Leu Ala Met Lys Ala
            420                 425                 430

Val Arg Asn Asn Arg Leu Gly Ser Ala Leu Ser Trp Ser Ile Arg Ala
        435                 440                 445

Lys Asp Ala Ala Phe Ala Thr Leu Val Ser Asp Arg Phe Leu Arg Asp
450                 455                 460
```

```
Tyr Cys Glu Arg Gly Cys Phe Ser Asp Leu Asp Leu Ile Asp Asn Leu
465                 470                 475                 480

Gly Pro Ala Met Met Leu Ser Asp Arg Leu Thr Phe Leu Gly Lys Tyr
            485                 490                 495

Arg Glu Phe His Arg Met Tyr Gly Glu Lys Arg Phe Ala Asp Ala Ala
                500                 505                 510

Ser Leu Leu Leu Ser Leu Met Thr Ser Arg Ile Ala Pro Arg Ser Phe
            515                 520                 525

Trp Met Thr Leu Leu Thr Asp Ala Leu Pro Leu Leu Glu Gln Lys Gln
            530                 535                 540

Val Ile Phe Ser Ala Glu Gln Thr Tyr Glu Leu Met Arg Cys Leu Glu
545                 550                 555                 560

Asp Leu Thr Ser Arg Arg Pro Val His Gly Glu Ser Asp Thr Glu Gln
                565                 570                 575

Leu Gln Asp Asp Asp Ile Glu Thr Thr Lys Val Glu Met Leu Arg Leu
            580                 585                 590

Ser Leu Ala Arg Asn Leu Ala Arg Ala Ile Ile Arg Glu Gly Ser Leu
            595                 600                 605

Glu Gly Ser
    610

<210> SEQ ID NO 5
<211> LENGTH: 510
<212> TYPE: DNA
<213> ORGANISM: Homo sapiens
<220> FEATURE:
<221> NAME/KEY: CDS
<222> LOCATION: (1)..(510)

<400> SEQUENCE: 5 atg gag gag ctc gat ggc gag cca aca gtc act ttg att cca ggc gtg      48
Met Glu Glu Leu Asp Gly Glu Pro Thr Val Thr Leu Ile Pro Gly Val
1               5                   10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
            20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
        35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
    50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
                85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca ggt gac     480
Ile Trp Asn Leu Cys Glu Ile Leu Phe Ile Glu Val Ala Pro Gly Asp
```

```
Ile Trp Asn Leu Cys Glu Ile Leu Phe Ile Glu Val Ala Pro Gly Asp
145                 150                 155                 160 cat ctt ggt gct gca ggg ccg gct gga tga                              510
His Leu Gly Ala Ala Gly Pro Ala Gly
                165

<210> SEQ ID NO 6
<211> LENGTH: 169
<212> TYPE: PRT
<213> ORGANISM: Homo sapiens

<400> SEQUENCE: 6

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
                20                  25                  30

Leu Val Cys Glu Thr Ser Phe Asn Lys Lys Glu Lys Ser Glu Met Val
            35                  40                  45

Pro Ser Cys Pro Phe Ile Tyr Ile Ile Arg Lys Asp Val Asp Val Tyr
        50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Gly Asp
145                 150                 155                 160

His Leu Gly Ala Ala Gly Pro Ala Gly
                165

<210> SEQ ID NO 7
<211> LENGTH: 540
<212> TYPE: DNA
<213> ORGANISM: Homo sapiens
<220> FEATURE:
<221> NAME/KEY: CDS
<222> LOCATION: (1)..(540)

<400> SEQUENCE: 7 atg gag gag ctc gat ggc gag cca aca gtc act ttg att cca ggc gtg    48
Met Glu Glu Leu Asp Gly Glu Pro Thr Val Thr Leu Ile Pro Gly Val
1               5                   10                  15 aat tcc aag aag aac caa atg tat ttt gac tgg ggt cca ggg gag atg    96
Asn Ser Lys Lys Asn Gln Met Tyr Phe Asp Trp Gly Pro Gly Glu Met
                20                  25                  30 ctg gta tgt gaa acc tcc ttc aac aaa aaa gaa aaa tca gag atg gtg   144
Leu Val Cys Glu Thr Ser Phe Asn Lys Lys Glu Lys Ser Glu Met Val
            35                  40                  45 cca agt tgc ccc ttt atc tat atc atc cgt aag gat gta gat gtt tac   192
Pro Ser Cys Pro Phe Ile Tyr Ile Ile Arg Lys Asp Val Asp Val Tyr
        50                  55                  60 tct caa atc ttg aga aaa ctc ttc aat gaa tcc cat gga atc ttt ctg   240
Ser Gln Ile Leu Arg Lys Leu Phe Asn Glu Ser His Gly Ile Phe Leu
65                  70                  75                  80
```

```
ggc ctc cag aga att gac gaa gag ttg act gga aaa tcc aga aaa tct    288
Gly Leu Gln Arg Ile Asp Glu Glu Leu Thr Gly Lys Ser Arg Lys Ser
                85                  90                  95 caa ttg gtt cga gtg agt aaa aac tac cga tca gtc atc aga gca tgt    336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat    384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc    432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gcc tgg    480
Ile Trp Asn Leu Cys Glu Ile Leu Phe Ile Glu Val Ala Pro Ala Trp
145                 150                 155                 160 gaa cac cca gac act gac aga gct gga gct gaa gtg gca gcc ctg gca    528
Glu His Pro Asp Thr Asp Arg Ala Gly Ala Glu Val Ala Ala Leu Ala
                165                 170                 175 cga gga atg tga                                                    540
Arg Gly Met <210> SEQ ID NO 8
<211> LENGTH: 179
<212> TYPE: PRT
<213> ORGANISM: Homo sapiens

<400> SEQUENCE: 8

Met Glu Glu Leu Asp Gly Glu Pro Thr Val Thr Leu Ile Pro Gly Val
 1               5                  10                  15

Asn Ser Lys Lys Asn Gln Met Tyr Phe Asp Trp Gly Pro Gly Glu Met
                20                  25                  30

Leu Val Cys Glu Thr Ser Phe Asn Lys Lys Glu Lys Ser Glu Met Val
            35                  40                  45

Pro Ser Cys Pro Phe Ile Tyr Ile Ile Arg Lys Asp Val Asp Val Tyr
        50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Trp
145                 150                 155                 160

Glu His Pro Asp Thr Asp Arg Ala Gly Ala Glu Val Ala Ala Leu Ala
                165                 170                 175

Arg Gly Met

<210> SEQ ID NO 9
<211> LENGTH: 1791
<212> TYPE: DNA
<213> ORGANISM: Homo sapiens
<220> FEATURE:
<221> NAME/KEY: CDS
<222> LOCATION: (1)..(1791)
```

<400> SEQUENCE: 9

```
atg gag gag ctc gat ggc gag cca aca gtc act ttg att cca ggc gtg         48
Met Glu Glu Leu Asp Gly Glu Pro Thr Val Thr Leu Ile Pro Gly Val
 1               5                  10                  15 aat tcc aag aag aac caa atg tat ttt gac tgg ggt cca ggg gag atg         96
Asn Ser Lys Lys Asn Gln Met Tyr Phe Asp Trp Gly Pro Gly Glu Met
            20                  25                  30 ctg gta tgt gaa acc tcc ttc aac aaa aaa gaa aaa tca gag atg gtg        144
Leu Val Cys Glu Thr Ser Phe Asn Lys Lys Glu Lys Ser Glu Met Val
        35                  40                  45 cca agt tgc ccc ttt atc tat atc atc cgt aag gat gta gat gtt tac        192
Pro Ser Cys Pro Phe Ile Tyr Ile Ile Arg Lys Asp Val Asp Val Tyr
    50                  55                  60 tct caa atc ttg aga aaa ctc ttc aat gaa tcc cat gga atc ttt ctg        240
Ser Gln Ile Leu Arg Lys Leu Phe Asn Glu Ser His Gly Ile Phe Leu
65                  70                  75                  80 ggc ctc cag aga att gac gaa gag ttg act gga aaa tcc aga aaa tct        288
Gly Leu Gln Arg Ile Asp Glu Glu Leu Thr Gly Lys Ser Arg Lys Ser
                85                  90                  95 caa ttg gtt cga gtg agt aaa aac tac cga tca gtc atc aga gca tgt        336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat        384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc        432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc        480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag        528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa        576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg        624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc        672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg        720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg        768
Pro Ile Leu Ser Pro Gly Asn Thr Gln Thr Leu Thr Glu Leu Glu Leu
                245                 250                 255 aag tgg cag cac tgg cac gag gaa tgt gag cgg tac ctc cag gac agc        816
Lys Trp Gln His Trp His Glu Glu Cys Glu Arg Tyr Leu Gln Asp Ser
            260                 265                 270 aca ttc gcc acc agc cct cac ctg gag tct ctc ttg aag att atg ctg        864
Thr Phe Ala Thr Ser Pro His Leu Glu Ser Leu Leu Lys Ile Met Leu
        275                 280                 285 gga gac gaa gct gcc ttg tta gag cag aag gaa ctt ctg agt aat tgg        912
Gly Asp Glu Ala Ala Leu Leu Glu Gln Lys Glu Leu Leu Ser Asn Trp
    290                 295                 300 tat cat ttc cta gtg act cgg ctc ttg tac tcc aat ccc aca gta aaa        960
```

```
Tyr His Phe Leu Val Thr Arg Leu Leu Tyr Ser Asn Pro Thr Val Lys
305                 310                 315                 320 ccc att gat ctg cac tac tat gcc cag tcc agc ctg gac ctg ttt ctg       1008
Pro Ile Asp Leu His Tyr Tyr Ala Gln Ser Ser Leu Asp Leu Phe Leu
                325                 330                 335 gga ggt gag agc agc cca gaa ccc ctg gac aac atc ttg ttg gca gcc       1056
Gly Gly Glu Ser Ser Pro Glu Pro Leu Asp Asn Ile Leu Leu Ala Ala
            340                 345                 350 ttt gag ttt gac atc cat caa gta atc aaa gag tgc agc atc gcc ctg       1104
Phe Glu Phe Asp Ile His Gln Val Ile Lys Glu Cys Ser Ile Ala Leu
        355                 360                 365 agc aac tgg tgg ttt gtg gcc cac ctg aca gac ctg ctg gac cac tgc       1152
Ser Asn Trp Trp Phe Val Ala His Leu Thr Asp Leu Leu Asp His Cys
    370                 375                 380 aag ctc ctc cag tca cac aac ctc tat ttc ggt tcc aac atg aga gag       1200
Lys Leu Leu Gln Ser His Asn Leu Tyr Phe Gly Ser Asn Met Arg Glu
385                 390                 395                 400 ttc ctc ctg ctg gag tac gcc tcg gga ctg ttt gct cat ccc agc ctg       1248
Phe Leu Leu Leu Glu Tyr Ala Ser Gly Leu Phe Ala His Pro Ser Leu
                405                 410                 415 tgg cag ctg ggg gtc gat tac ttt gat tac tgc ccc gag ctg ggc cga       1296
Trp Gln Leu Gly Val Asp Tyr Phe Asp Tyr Cys Pro Glu Leu Gly Arg
            420                 425                 430 gtc tcc ctg gag ctg cac att gag cgg ata cct ctg aac acc gag cag       1344
Val Ser Leu Glu Leu His Ile Glu Arg Ile Pro Leu Asn Thr Glu Gln
        435                 440                 445 aaa gcc ctg aag gtg ctg cgg atc tgt gag cag cgg cag atg act gaa       1392
Lys Ala Leu Lys Val Leu Arg Ile Cys Glu Gln Arg Gln Met Thr Glu
    450                 455                 460 caa gtt cgc agc att tgt aag atc tta gcc atg aaa gcc gtc cgc aac       1440
Gln Val Arg Ser Ile Cys Lys Ile Leu Ala Met Lys Ala Val Arg Asn
465                 470                 475                 480 aat cgc ctg ggt tct gcc ctc tct tgg agc atc cgt gct aag gat gcc       1488
Asn Arg Leu Gly Ser Ala Leu Ser Trp Ser Ile Arg Ala Lys Asp Ala
                485                 490                 495 gcc ttt gcc acg ctc gtg tca gac agg ttc ctc agg gat tac tgt gag       1536
Ala Phe Ala Thr Leu Val Ser Asp Arg Phe Leu Arg Asp Tyr Cys Glu
            500                 505                 510 cga ggc tgc ttt tct gat ttg gat ctc att gac aac ctg ggg cca gcc       1584
Arg Gly Cys Phe Ser Asp Leu Asp Leu Ile Asp Asn Leu Gly Pro Ala
        515                 520                 525 atg atg ctc agt gac cga ctg aca ttc ctg gta tcg cga gtt cca ccg       1632
Met Met Leu Ser Asp Arg Leu Thr Phe Leu Val Ser Arg Val Pro Pro
    530                 535                 540 tat gta cgg gga gaa gcg ttt tgc cga cgc agc ttc tct cct tct gtc       1680
Tyr Val Arg Gly Glu Ala Phe Cys Arg Arg Ser Phe Ser Pro Ser Val
545                 550                 555                 560 ctt gat gac gtc tcg gat tgc ccc tcg gtc ttt ctg gat gac tct gct       1728
Leu Asp Asp Val Ser Asp Cys Pro Ser Val Phe Leu Asp Asp Ser Ala
                565                 570                 575 gac aga tgc ctt gcc cct ttt gga aca gaa aca ggt gat ttt ctc agc       1776
Asp Arg Cys Leu Ala Pro Phe Gly Thr Glu Thr Gly Asp Phe Leu Ser
            580                 585                 590 aga aca gac tta tga                                                    1791
Arg Thr Asp Leu
        595

<210> SEQ ID NO 10
<211> LENGTH: 596
<212> TYPE: PRT
```

<213> ORGANISM: Homo sapiens

<400> SEQUENCE: 10

```
Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Leu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
        275                 280                 285

Gly Asp Glu Ala Ala Leu Leu Glu Gln Lys Glu Leu Leu Ser Asn Trp
    290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Ser Ser Leu Asp Leu Phe Leu
                325                 330                 335

Gly Gly Glu Ser Ser Pro Glu Pro Leu Asp Asn Ile Leu Leu Ala Ala
            340                 345                 350

Phe Glu Phe Asp Ile His Gln Val Ile Lys Glu Cys Ser Ile Ala Leu
        355                 360                 365

Ser Asn Trp Trp Phe Val Ala His Leu Thr Asp Leu Leu Asp His Cys
    370                 375                 380

Lys Leu Leu Gln Ser His Asn Leu Tyr Phe Gly Ser Asn Met Arg Glu
385                 390                 395                 400
```

```
Phe Leu Leu Leu Glu Tyr Ala Ser Gly Leu Phe Ala His Pro Ser Leu
            405                 410                 415

Trp Gln Leu Gly Val Asp Tyr Phe Asp Tyr Cys Pro Glu Leu Gly Arg
        420                 425                 430

Val Ser Leu Glu Leu His Ile Glu Arg Ile Pro Leu Asn Thr Glu Gln
            435                 440                 445

Lys Ala Leu Lys Val Leu Arg Ile Cys Glu Gln Arg Gln Met Thr Glu
450                 455                 460

Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
            485                 490                 495

Ala Phe Ala Thr Leu Val Ser Asp Arg Phe Leu Arg Asp Tyr Cys Glu
            500                 505                 510

Arg Gly Cys Phe Ser Asp Leu Asp Leu Ile Asp Asn Leu Gly Pro Ala
            515                 520                 525

Met Met Leu Ser Asp Arg Leu Thr Phe Leu Val Ser Arg Val Pro Pro
530                 535                 540

Tyr Val Arg Gly Glu Ala Phe Cys Arg Arg Ser Phe Ser Pro Ser Val
545                 550                 555                 560

Leu Asp Asp Val Ser Asp Cys Pro Ser Val Phe Leu Asp Asp Ser Ala
            565                 570                 575

Asp Arg Cys Leu Ala Pro Phe Gly Thr Glu Thr Gly Asp Phe Leu Ser
            580                 585                 590

Arg Thr Asp Leu
        595

<210> SEQ ID NO 11
<211> LENGTH: 39
<212> TYPE: DNA
<213> ORGANISM: Homo sapiens
<220> FEATURE:
<221> NAME/KEY: CDS
<222> LOCATION: (1)..(39)

<400> SEQUENCE: 11 atg gag gag ctc gat ggc gag cca aca gtc act gcg tga              39
Met Glu Glu Leu Asp Gly Glu Pro Thr Val Thr Ala
 1               5                  10

<210> SEQ ID NO 12
<211> LENGTH: 12
<212> TYPE: PRT
<213> ORGANISM: Homo sapiens

<400> SEQUENCE: 12

Met Glu Glu Leu Asp Gly Glu Pro Thr Val Thr Ala
 1               5                  10

<210> SEQ ID NO 13
<211> LENGTH: 711
<212> TYPE: DNA
<213> ORGANISM: Homo sapiens
<220> FEATURE:
<221> NAME/KEY: CDS
<222> LOCATION: (1)..(711)

<400> SEQUENCE: 13 atg gag gag ctc gat ggc gag cca aca gtc act ttg att cca ggc gtg   48
Met Glu Glu Leu Asp Gly Glu Pro Thr Val Thr Leu Ile Pro Gly Val
 1               5                  10                  15
```

```
aat tcc aag aag aac caa atg tat ttt gac tgg ggt cca ggg gag atg    96
Asn Ser Lys Lys Asn Gln Met Tyr Phe Asp Trp Gly Pro Gly Glu Met
            20                  25                  30 ctg gta tgt gaa acc tcc ttc aac aaa aaa gaa aaa tca gag atg gtg    144
Leu Val Cys Glu Thr Ser Phe Asn Lys Lys Glu Lys Ser Glu Met Val
        35                  40                  45 cca agt tgc ccc ttt atc tat atc atc cgt aag gat gta gat gtt tac    192
Pro Ser Cys Pro Phe Ile Tyr Ile Ile Arg Lys Asp Val Asp Val Tyr
    50                  55                  60 tct caa atc ttg aga aaa ctc ttc aat gaa tcc cat gga atc ttt ctg    240
Ser Gln Ile Leu Arg Lys Leu Phe Asn Glu Ser His Gly Ile Phe Leu
65                  70                  75                  80 ggc ctc cag aga att gac gaa gag ttg act gga aaa tcc aga aaa tct    288
Gly Leu Gln Arg Ile Asp Glu Glu Leu Thr Gly Lys Ser Arg Lys Ser
                85                  90                  95 caa ttg gtt cga gtg agt aaa aac tac cga tca gtc atc aga gca tgt    336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat    384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc    432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc    480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag    528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa    576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag gca gat    624
His Asp Ser Phe Trp Asn Leu Val Thr Ile Leu Val Leu Gln Ala Asp
        195                 200                 205 gct ctc caa gga agc cga tgc cag ccc cgc ctc tgc agg cat atg ccg    672
Ala Leu Gln Gly Ser Arg Cys Gln Pro Arg Leu Cys Arg His Met Pro
    210                 215                 220 aat cat ggg gga cct gat gag gac aat gcc cat tct tag                711
Asn His Gly Gly Pro Asp Glu Asp Asn Ala His Ser
225                 230                 235

<210> SEQ ID NO 14
<211> LENGTH: 236
<212> TYPE: PRT
<213> ORGANISM: Homo sapiens

<400> SEQUENCE: 14

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80
```

```
Gly Leu Gln Arg Ile Asp Glu Glu Leu Thr Gly Lys Ser Arg Lys Ser
             85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Ala Asp
        195                 200                 205

Ala Leu Gln Gly Ser Arg Cys Gln Pro Arg Leu Cys Arg His Met Pro
    210                 215                 220

Asn His Gly Gly Pro Asp Glu Asp Asn Ala His Ser
225                 230                 235

<210> SEQ ID NO 15
<211> LENGTH: 666
<212> TYPE: DNA
<213> ORGANISM: Homo sapiens
<220> FEATURE:
<221> NAME/KEY: CDS
<222> LOCATION: (1)..(666)

<400> SEQUENCE: 15 atg gag gag ctc gat ggc gag cca aca gtc act ttg att cca ggc gtg      48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
             85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc     480
```

```
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag    528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa    576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg    624
His Asp Ser Phe Trp Asn Leu Val Thr Ile Leu Val Leu Gln Gly Arg
        195                 200                 205 ctg gat gag gcc cga cag atg ctc gaa tca tgg ggg acc tga             666
Leu Asp Glu Ala Arg Gln Met Leu Glu Ser Trp Gly Thr
    210                 215                 220

<210> SEQ ID NO 16
<211> LENGTH: 221
<212> TYPE: PRT
<213> ORGANISM: Homo sapiens

<400> SEQUENCE: 16

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Glu Ser Trp Gly Thr
    210                 215                 220

<210> SEQ ID NO 17
<211> LENGTH: 765
<212> TYPE: DNA
<213> ORGANISM: Homo sapiens
<220> FEATURE:
<221> NAME/KEY: CDS
<222> LOCATION: (1)..(765)

<400> SEQUENCE: 17
```

```
atg gag gag ctc gat ggc gag cca aca gtc act ttg att cca ggc gtg      48
Met Glu Glu Leu Asp Gly Glu Pro Thr Val Thr Leu Ile Pro Gly Val
 1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
                 20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
             35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
 50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
             100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
         115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
     130                 135                 140 atc tgg aac ctg tgt gag att ctt ttt att gaa gtg gcc cca gct ggc     480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag     528
Pro Leu Leu Leu His Leu Leu Asp Trp Val Arg Leu His Val Cys Glu
                 165                 170                 175 gtg gac agt ttg tcg gca gat gtt ctg ggc agt gag aat cca agc aaa     576
Val Asp Ser Leu Ser Ala Asp Val Leu Gly Ser Glu Asn Pro Ser Lys
             180                 185                 190 cat gac agc ttc tgg aac ttg gtg acc atc ttg gtg ctg cag ggc cgg     624
His Asp Ser Phe Trp Asn Leu Val Thr Ile Leu Val Leu Gln Gly Arg
         195                 200                 205 ctg gat gag gcc cga cag atg ctc tcc aag gaa gcc gat gcc agc ccc     672
Leu Asp Glu Ala Arg Gln Met Leu Ser Lys Glu Ala Asp Ala Ser Pro
     210                 215                 220 gcc tct gca ggc ata tgc cga atc atg ggg gac ctg atg agg aca atg     720
Ala Ser Ala Gly Ile Cys Arg Ile Met Gly Asp Leu Met Arg Thr Met
225                 230                 235                 240 ccc att ctt agt aga tta tgc tgg gag acg aag ctg cct tgt tag         765
Pro Ile Leu Ser Arg Leu Cys Trp Glu Thr Lys Leu Pro Cys
                 245                 250

<210> SEQ ID NO 18
<211> LENGTH: 254
<212> TYPE: PRT
<213> ORGANISM: Homo sapiens

<400> SEQUENCE: 18

Met Glu Glu Leu Asp Gly Glu Pro Thr Val Thr Leu Ile Pro Gly Val
 1               5                  10                  15

Asn Ser Lys Lys Asn Gln Met Tyr Phe Asp Trp Gly Pro Gly Glu Met
                 20                  25                  30
```

```
Leu Val Cys Glu Thr Ser Phe Asn Lys Lys Glu Lys Ser Glu Met Val
            35                  40                  45

Pro Ser Cys Pro Phe Ile Tyr Ile Ile Arg Lys Asp Val Asp Val Tyr
 50                  55                  60

Ser Gln Ile Leu Arg Lys Leu Phe Asn Glu Ser His Gly Ile Phe Leu
 65                  70                  75                  80

Gly Leu Gln Arg Ile Asp Glu Glu Leu Thr Gly Lys Ser Arg Lys Ser
                 85                  90                  95

Gln Leu Val Arg Val Ser Lys Asn Tyr Arg Ser Val Ile Arg Ala Cys
                100                 105                 110

Met Glu Glu Met His Gln Val Ala Ile Ala Lys Asp Pro Ala Asn
                115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
                180                 185                 190

His Asp Ser Phe Trp Asn Leu Val Thr Ile Leu Val Leu Gln Gly Arg
                195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Arg Leu Cys Trp Glu Thr Lys Leu Pro Cys
                245                 250

<210> SEQ ID NO 19
<211> LENGTH: 858
<212> TYPE: DNA
<213> ORGANISM: Homo sapiens
<220> FEATURE:
<221> NAME/KEY: CDS
<222> LOCATION: (1)..(858)

<400> SEQUENCE: 19 atg gag gag ctc gat ggc gag cca aca gtc act ttg att cca ggc gtg     48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg     96
Asn Ser Lys Lys Asn Gln Met Tyr Phe Asp Trp Gly Pro Gly Glu Met
                 20                  25                  30 ctg gta tgt gaa acc tcc ttc aac aaa aaa gaa aaa tca gag atg gtg    144
Leu Val Cys Glu Thr Ser Phe Asn Lys Lys Glu Lys Ser Glu Met Val
            35                  40                  45 cca agt tgc ccc ttt atc tat atc atc cgt aag gat gta gat gtt tac    192
Pro Ser Cys Pro Phe Ile Tyr Ile Ile Arg Lys Asp Val Asp Val Tyr
 50                  55                  60 tct caa atc ttg aga aaa ctc ttc aat gaa tcc cat gga atc ttt ctg    240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct    288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt    336
Gln Leu Val Arg Val Ser Lys Asn Tyr Arg Ser Val Ile Arg Ala Cys
```

```
                 100                 105                 110
atg gag gaa atg cac cag gtt gca att gct gct aaa gat cca gcc aat    384
Met Glu Glu Met His Gln Val Ala Ile Ala Ala Lys Asp Pro Ala Asn
            115                 120                 125 ggc cgc cag ttc agc agc cag gtc tcc att ttg tca gca atg gag ctc    432
Gly Arg Gln Phe Ser Ser Gln Val Ser Ile Leu Ser Ala Met Glu Leu
130                 135                 140 atc tgg aac ctg tgt gag att ctt ttt att gaa gtg gcc cca gct ggc    480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag    528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa    576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg    624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc    672
Leu Asp Glu Ala Arg Gln Met Leu Ser Lys Glu Ala Asp Ala Ser Pro
210                 215                 220 gcc tct gca ggc ata tgc cga atc atg ggg gac ctg atg agg aca atg    720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg    768
Pro Ile Leu Ser Pro Gly Asn Thr Gln Thr Leu Thr Glu Leu Glu Leu
                245                 250                 255 aag tgg cag cac tgg cac gag gaa tgt gag cgg tac ctc cag gac agc    816
Lys Trp Gln His Trp His Glu Glu Cys Glu Arg Tyr Leu Gln Asp Ser
            260                 265                 270 aca ttc gcc acc agc cct cac ctg gag tct ctc ttg aag tga            858
Thr Phe Ala Thr Ser Pro His Leu Glu Ser Leu Leu Lys
        275                 280                 285

<210> SEQ ID NO 20
<211> LENGTH: 285
<212> TYPE: PRT
<213> ORGANISM: Homo sapiens

<400> SEQUENCE: 20

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
```

```
                130                 135                 140
Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
                180                 185                 190

His Asp Ser Phe Trp Asn Leu Val Thr Ile Leu Val Leu Gln Gly Arg
                195                 200                 205

Leu Asp Glu Ala Arg Gln Met Leu Ser Lys Glu Ala Asp Ala Ser Pro
210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
                260                 265                 270

Thr Phe Ala Thr Ser Pro His Leu Glu Ser Leu Leu Lys
                275                 280                 285

<210> SEQ ID NO 21
<211> LENGTH: 1857
<212> TYPE: DNA
<213> ORGANISM: Homo sapiens
<220> FEATURE:
<221> NAME/KEY: CDS
<222> LOCATION: (1)..(1857)

<400> SEQUENCE: 21 atg gag gag ctc gat ggc gag cca aca gtc act ttg att cca ggc gtg      48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc     480
Ile Trp Asn Leu Cys Glu Ile Leu Phe Ile Glu Val Ala Pro Ala Gly
145                 150                 155                 160
```

```
cct ctc ctc ctc cat ctc ctt gac tgg gtc cgg ctc cat gtg tgc gag      528
Pro Leu Leu Leu His Leu Leu Asp Trp Val Arg Leu His Val Cys Glu
            165                 170                 175 gtg gac agt ttg tcg gca gat gtt ctg ggc agt gag aat cca agc aaa      576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg      624
His Asp Ser Phe Trp Asn Leu Val Thr Ile Leu Val Leu Gln Gly Arg
            195                 200                 205 ctg gat gag gcc cga cag atg ctc tcc aag gaa gcc gat gcc agc ccc      672
Leu Asp Glu Ala Arg Gln Met Leu Ser Lys Glu Ala Asp Ala Ser Pro
210                 215                 220 gcc tct gca ggc ata tgc cga atc atg ggg gac ctg atg agg aca atg      720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg      768
Pro Ile Leu Ser Pro Gly Asn Thr Gln Thr Leu Thr Glu Leu Glu Leu
            245                 250                 255 aag tgg cag cac tgg cac gag gaa tgt gag cgg tac ctc cag gac agc      816
Lys Trp Gln His Trp His Glu Glu Cys Glu Arg Tyr Leu Gln Asp Ser
            260                 265                 270 aca ttc gcc acc agc cct cac ctg gag tct ctc ttg aag att atg ctg      864
Thr Phe Ala Thr Ser Pro His Leu Glu Ser Leu Leu Lys Ile Met Leu
            275                 280                 285 gga gac gaa gct gcc ttg tta gag cag aag gaa ctt ctg agt aat tgg      912
Gly Asp Glu Ala Ala Leu Leu Glu Gln Lys Glu Leu Leu Ser Asn Trp
            290                 295                 300 tat cat ttc cta gtg act cgg ctc ttg tac tcc aat ccc aca gta aaa      960
Tyr His Phe Leu Val Thr Arg Leu Leu Tyr Ser Asn Pro Thr Val Lys
305                 310                 315                 320 ccc att gat ctg cac tgc agc atc gcc ctg agc aac tgg tgg ttt gtg     1008
Pro Ile Asp Leu His Cys Ser Ile Ala Leu Ser Asn Trp Trp Phe Val
            325                 330                 335 gcc cac ctg aca gac ctg ctg gac cac tgc aag ctc ctc cag tca cac     1056
Ala His Leu Thr Asp Leu Leu Asp His Cys Lys Leu Leu Gln Ser His
            340                 345                 350 aac ctc tat ttc ggt tcc aac atg aga gag ttc ctc ctg ctg gag tac     1104
Asn Leu Tyr Phe Gly Ser Asn Met Arg Glu Phe Leu Leu Leu Glu Tyr
            355                 360                 365 gcc tcg gga ctg ttt gct cat ccc agc ctg tgg cag ctg ggg gtc gat     1152
Ala Ser Gly Leu Phe Ala His Pro Ser Leu Trp Gln Leu Gly Val Asp
            370                 375                 380 tac ttt gat tac tgc ccc gag ctg ggc cga gtc tcc ctg gag ctg cac     1200
Tyr Phe Asp Tyr Cys Pro Glu Leu Gly Arg Val Ser Leu Glu Leu His
385                 390                 395                 400 att gag cgg ata cct ctg aac acc gag cag aaa gcc ctg aag gtg ctg     1248
Ile Glu Arg Ile Pro Leu Asn Thr Glu Gln Lys Ala Leu Lys Val Leu
            405                 410                 415 cgg atc tgt gag cag cgg cag atg act gaa caa gtt cgc agc att tgt     1296
Arg Ile Cys Glu Gln Arg Gln Met Thr Glu Gln Val Arg Ser Ile Cys
            420                 425                 430 aag atc tta gcc atg aaa gcc gtc cgc aac aat cgc ctg ggt tct gcc     1344
Lys Ile Leu Ala Met Lys Ala Val Arg Asn Asn Arg Leu Gly Ser Ala
            435                 440                 445 ctc tct tgg agc atc cgt gct aag gat gcc gcc ttt gcc acg ctc gtg     1392
Leu Ser Trp Ser Ile Arg Ala Lys Asp Ala Ala Phe Ala Thr Leu Val
450                 455                 460 tca gac agg ttc ctc agg gat tac tgt gag cga ggc tgc ttt tct gat     1440
Ser Asp Arg Phe Leu Arg Asp Tyr Cys Glu Arg Gly Cys Phe Ser Asp
```

```
                465                 470                 475                 480
ttg gat ctc att gac aac ctg ggg cca gcc atg atg ctc agt gac cga          1488
Leu Asp Leu Ile Asp Asn Leu Gly Pro Ala Met Met Leu Ser Asp Arg
                        485                 490                 495 ctg aca ttc ctg gga aag tat cgc gag ttc cac cgt atg tac ggg gag          1536
Leu Thr Phe Leu Gly Lys Tyr Arg Glu Phe His Arg Met Tyr Gly Glu
                500                 505                 510 aag cgt ttt gcc gac gca gct tct ctc ctt ctg tcc ttg atg acg tct          1584
Lys Arg Phe Ala Asp Ala Ala Ser Leu Leu Leu Ser Leu Met Thr Ser
            515                 520                 525 cgg att gcc cct cgg tct ttc tgg atg act ctg ctg aca gat gcc ttg          1632
Arg Ile Ala Pro Arg Ser Phe Trp Met Thr Leu Leu Thr Asp Ala Leu
        530                 535                 540 ccc ctt ttg gaa cag aaa cag gtg att ttc tca gca gaa cag act tat          1680
Pro Leu Leu Glu Gln Lys Gln Val Ile Phe Ser Ala Glu Gln Thr Tyr
545                 550                 555                 560 gag ttg atg cgg tgt ctg gag gac ttg acg tca aga aga cct gtg cat          1728
Glu Leu Met Arg Cys Leu Glu Asp Leu Thr Ser Arg Arg Pro Val His
                565                 570                 575 gga gaa tct gat acc gag cag ctc cag gat gat gac ata gag acc acc          1776
Gly Glu Ser Asp Thr Glu Gln Leu Gln Asp Asp Asp Ile Glu Thr Thr
            580                 585                 590 aag gtg gaa atg ctg aga ctt tct ctg gca cga aat ctt gct cgg gca          1824
Lys Val Glu Met Leu Arg Leu Ser Leu Ala Arg Asn Leu Ala Arg Ala
        595                 600                 605 att ata aga gaa ggc tca ctg gaa ggt tcc tga                              1857
Ile Ile Arg Glu Gly Ser Leu Glu Gly Ser
610                 615

<210> SEQ ID NO 22
<211> LENGTH: 618
<212> TYPE: PRT
<213> ORGANISM: Homo sapiens

<400> SEQUENCE: 22

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
                20                  25                  30

Leu Val Cys Glu Thr Ser Phe Asn Lys Lys Glu Lys Ser Glu Met Val
            35                  40                  45

Pro Ser Cys Pro Phe Ile Tyr Ile Ile Arg Lys Asp Val Asp Val Tyr
        50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175
```

-continued

```
Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
        275                 280                 285

Gly Asp Glu Ala Ala Leu Leu Glu Gln Lys Glu Leu Leu Ser Asn Trp
    290                 295                 300

Tyr His Phe Leu Val Thr Arg Leu Leu Tyr Ser Asn Pro Thr Val Lys
305                 310                 315                 320

Pro Ile Asp Leu His Cys Ser Ile Ala Leu Ser Asn Trp Trp Phe Val
                325                 330                 335

Ala His Leu Thr Asp Leu Leu Asp His Cys Lys Leu Leu Gln Ser His
            340                 345                 350

Asn Leu Tyr Phe Gly Ser Asn Met Arg Glu Phe Leu Leu Leu Glu Tyr
        355                 360                 365

Ala Ser Gly Leu Phe Ala His Pro Ser Leu Trp Gln Leu Gly Val Asp
    370                 375                 380

Tyr Phe Asp Tyr Cys Pro Glu Leu Gly Arg Val Ser Leu Glu Leu His
385                 390                 395                 400

Ile Glu Arg Ile Pro Leu Asn Thr Glu Gln Lys Ala Leu Lys Val Leu
                405                 410                 415

Arg Ile Cys Glu Gln Arg Gln Met Thr Glu Gln Val Arg Ser Ile Cys
            420                 425                 430

Lys Ile Leu Ala Met Lys Ala Val Arg Asn Asn Arg Leu Gly Ser Ala
        435                 440                 445

Leu Ser Trp Ser Ile Arg Ala Lys Asp Ala Ala Phe Ala Thr Leu Val
    450                 455                 460

Ser Asp Arg Phe Leu Arg Asp Tyr Cys Glu Arg Gly Cys Phe Ser Asp
465                 470                 475                 480

Leu Asp Leu Ile Asp Asn Leu Gly Pro Ala Met Met Leu Ser Asp Arg
                485                 490                 495

Leu Thr Phe Leu Gly Lys Tyr Arg Glu Phe His Arg Met Tyr Gly Glu
            500                 505                 510

Lys Arg Phe Ala Asp Ala Ala Ser Leu Leu Ser Leu Met Thr Ser
        515                 520                 525

Arg Ile Ala Pro Arg Ser Phe Trp Met Thr Leu Leu Thr Asp Ala Leu
    530                 535                 540

Pro Leu Leu Glu Gln Lys Gln Val Ile Phe Ser Ala Glu Gln Thr Tyr
545                 550                 555                 560

Glu Leu Met Arg Cys Leu Glu Asp Leu Thr Ser Arg Arg Pro Val His
                565                 570                 575

Gly Glu Ser Asp Thr Glu Gln Leu Gln Asp Asp Ile Glu Thr Thr
            580                 585                 590

Lys Val Glu Met Leu Arg Leu Ser Leu Ala Arg Asn Leu Ala Arg Ala
```

```
                    595                 600                 605
Ile Ile Arg Glu Gly Ser Leu Glu Gly Ser
    610                 615

<210> SEQ ID NO 23
<211> LENGTH: 1785
<212> TYPE: DNA
<213> ORGANISM: Homo sapiens
<220> FEATURE:
<221> NAME/KEY: CDS
<222> LOCATION: (1)..(1785)

<400> SEQUENCE: 23 atg gag gag ctc gat ggc gag cca aca gtc act ttg att cca ggc gtg      48
Met Glu Glu Leu Asp Gly Glu Pro Thr Val Thr Leu Ile Pro Gly Val
 1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc     480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag     528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa     576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg     624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc     672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg     720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg     768
Pro Ile Leu Ser Pro Gly Asn Thr Gln Thr Leu Thr Glu Leu Glu Leu
                245                 250                 255
```

```
aag tgg cag cac tgg cac gag gaa tgt gag cgg tac ctc cag gac agc      816
Lys Trp Gln His Trp His Glu Glu Cys Glu Arg Tyr Leu Gln Asp Ser
        260                 265                 270 aca ttc gcc acc agc cct cac ctg gag tct ctc ttg aag att atg ctg      864
Thr Phe Ala Thr Ser Pro His Leu Glu Ser Leu Leu Lys Ile Met Leu
    275                 280                 285 gga gac gaa gct gcc ttg tta gag cag aag gaa ctt ctg agt aat tgg      912
Gly Asp Glu Ala Ala Leu Leu Glu Gln Lys Glu Leu Leu Ser Asn Trp
290                 295                 300 tat cat ttc cta gtg act cgg ctc ttg tac tcc aat ccc aca gta aaa      960
Tyr His Phe Leu Val Thr Arg Leu Leu Tyr Ser Asn Pro Thr Val Lys
305                 310                 315                 320 ccc att gat ctg cac tac tat gcc cag tcc agc ctg gac ctg ttt ctg     1008
Pro Ile Asp Leu His Tyr Tyr Ala Gln Ser Ser Leu Asp Leu Phe Leu
            325                 330                 335 gga ggt gag agc agc cca gaa ccc ctg gac aac atc ttg ttg gca gcc     1056
Gly Gly Glu Ser Ser Pro Glu Pro Leu Asp Asn Ile Leu Leu Ala Ala
        340                 345                 350 ttt gag ttt gac atc cat caa gta atc aaa gag tgc agc atc gcc ctg     1104
Phe Glu Phe Asp Ile His Gln Val Ile Lys Glu Cys Ser Ile Ala Leu
    355                 360                 365 agc aac tgg tgg ttt gtg gcc cac ctg aca gac ctg ctg gac cac tgc     1152
Ser Asn Trp Trp Phe Val Ala His Leu Thr Asp Leu Leu Asp His Cys
370                 375                 380 aag ctc ctc cag tca cac aac ctc tat ttc ggt tcc aac atg aga gag     1200
Lys Leu Leu Gln Ser His Asn Leu Tyr Phe Gly Ser Asn Met Arg Glu
385                 390                 395                 400 ttc ctc ctg ctg gag tac gcc tcg gga ctg ttt gct cat ccc agc ctg     1248
Phe Leu Leu Leu Glu Tyr Ala Ser Gly Leu Phe Ala His Pro Ser Leu
            405                 410                 415 tgg cag ctg ggg gtc gat tac ttt gat tac tgc ccc gag ctg ggc cga     1296
Trp Gln Leu Gly Val Asp Tyr Phe Asp Tyr Cys Pro Glu Leu Gly Arg
        420                 425                 430 gtc tcc ctg gag ctg cac att gag cgg ata cct ctg aac acc gag cag     1344
Val Ser Leu Glu Leu His Ile Glu Arg Ile Pro Leu Asn Thr Glu Gln
    435                 440                 445 aaa gcc ctg aag gtg ctg cgg atc tgt gag cag cgg cag atg act gaa     1392
Lys Ala Leu Lys Val Leu Arg Ile Cys Glu Gln Arg Gln Met Thr Glu
450                 455                 460 caa gtt cgc agc att tgt aag atc tta gcc atg aaa gcc gtc cgc aac     1440
Gln Val Arg Ser Ile Cys Lys Ile Leu Ala Met Lys Ala Val Arg Asn
465                 470                 475                 480 aat cgc ctg ggt tct gcc ctc tct tgg agc atc cgt gct aag gat gcc     1488
Asn Arg Leu Gly Ser Ala Leu Ser Trp Ser Ile Arg Ala Lys Asp Ala
            485                 490                 495 gcc ttt gcc acg ctc gtg tca gac agg ttc ctc agg gat tac tgt gag     1536
Ala Phe Ala Thr Leu Val Ser Asp Arg Phe Leu Arg Asp Tyr Cys Glu
        500                 505                 510 cga ggc tgc ttt tct gat ttg gat ctc att gac aac ctg ggg cca gcc     1584
Arg Gly Cys Phe Ser Asp Leu Asp Leu Ile Asp Asn Leu Gly Pro Ala
    515                 520                 525 atg atg ctc agt gac cga ctg aca ttc ctg gga aag tat cgc gag ttc     1632
Met Met Leu Ser Asp Arg Leu Thr Phe Leu Gly Lys Tyr Arg Glu Phe
530                 535                 540 cac cgt atg tac ggg gag aag cgt ttt gcc gac gca gct tct ctc ctt     1680
His Arg Met Tyr Gly Glu Lys Arg Phe Ala Asp Ala Ala Ser Leu Leu
545                 550                 555                 560 ctg tcc ttg atg acg tct cgg att gcc cct cgg tct ttc tgg atg act     1728
Leu Ser Leu Met Thr Ser Arg Ile Ala Pro Arg Ser Phe Trp Met Thr
```

-continued

```
            565                 570                 575
ctg ctg aca gat gcc ttg ccc ctt ttg gaa cag aaa cag aac aga ctt    1776
Leu Leu Thr Asp Ala Leu Pro Leu Leu Glu Gln Lys Gln Asn Arg Leu
            580                 585                 590 atg agt tga                                                        1785
Met Ser
```

<210> SEQ ID NO 24
<211> LENGTH: 594
<212> TYPE: PRT
<213> ORGANISM: Homo sapiens

<400> SEQUENCE: 24

| | | | | | | | | | | | | | | | |
|---|---|---|---|---|---|---|---|---|---|---|---|---|---|---|---|
| Met | Glu | Glu | Leu | Asp | Gly | Glu | Pro | Thr | Val | Thr | Leu | Ile | Pro | Gly | Val |
| 1 | | | | 5 | | | | | 10 | | | | | 15 | |
| Asn | Ser | Lys | Lys | Asn | Gln | Met | Tyr | Phe | Asp | Trp | Gly | Pro | Gly | Glu | Met |
| | | | 20 | | | | | 25 | | | | | 30 | | |
| Leu | Val | Cys | Glu | Thr | Ser | Phe | Asn | Lys | Lys | Glu | Lys | Ser | Glu | Met | Val |
| | | | 35 | | | | | 40 | | | | | 45 | | |
| Pro | Ser | Cys | Pro | Phe | Ile | Tyr | Ile | Ile | Arg | Lys | Asp | Val | Asp | Val | Tyr |
| | 50 | | | | | 55 | | | | | 60 | | | | |
| Ser | Gln | Ile | Leu | Arg | Lys | Leu | Phe | Asn | Glu | Ser | His | Gly | Ile | Phe | Leu |
| 65 | | | | | 70 | | | | | 75 | | | | | 80 |
| Gly | Leu | Gln | Arg | Ile | Asp | Glu | Glu | Leu | Thr | Gly | Lys | Ser | Arg | Lys | Ser |
| | | | | 85 | | | | | 90 | | | | | 95 | |
| Gln | Leu | Val | Arg | Val | Ser | Lys | Asn | Tyr | Arg | Ser | Val | Ile | Arg | Ala | Cys |
| | | | 100 | | | | | 105 | | | | | 110 | | |
| Met | Glu | Glu | Met | His | Gln | Val | Ala | Ile | Ala | Ala | Lys | Asp | Pro | Ala | Asn |
| | | | 115 | | | | | 120 | | | | | 125 | | |
| Gly | Arg | Gln | Phe | Ser | Ser | Gln | Val | Ser | Ile | Leu | Ser | Ala | Met | Glu | Leu |
| | 130 | | | | | 135 | | | | | 140 | | | | |
| Ile | Trp | Asn | Leu | Cys | Glu | Ile | Leu | Phe | Ile | Glu | Val | Ala | Pro | Ala | Gly |
| 145 | | | | | 150 | | | | | 155 | | | | | 160 |
| Pro | Leu | Leu | Leu | His | Leu | Leu | Asp | Trp | Val | Arg | Leu | His | Val | Cys | Glu |
| | | | | 165 | | | | | 170 | | | | | 175 | |
| Val | Asp | Ser | Leu | Ser | Ala | Asp | Val | Leu | Gly | Ser | Glu | Asn | Pro | Ser | Lys |
| | | | 180 | | | | | 185 | | | | | 190 | | |
| His | Asp | Ser | Phe | Trp | Asn | Leu | Val | Thr | Ile | Leu | Val | Leu | Gln | Gly | Arg |
| | | | 195 | | | | | 200 | | | | | 205 | | |
| Leu | Asp | Glu | Ala | Arg | Gln | Met | Leu | Ser | Lys | Glu | Ala | Asp | Ala | Ser | Pro |
| | 210 | | | | | 215 | | | | | 220 | | | | |
| Ala | Ser | Ala | Gly | Ile | Cys | Arg | Ile | Met | Gly | Asp | Leu | Met | Arg | Thr | Met |
| 225 | | | | | 230 | | | | | 235 | | | | | 240 |
| Pro | Ile | Leu | Ser | Pro | Gly | Asn | Thr | Gln | Thr | Leu | Thr | Glu | Leu | Glu | Leu |
| | | | | 245 | | | | | 250 | | | | | 255 | |
| Lys | Trp | Gln | His | Trp | His | Glu | Glu | Cys | Glu | Arg | Tyr | Leu | Gln | Asp | Ser |
| | | | 260 | | | | | 265 | | | | | 270 | | |
| Thr | Phe | Ala | Thr | Ser | Pro | His | Leu | Glu | Ser | Leu | Leu | Lys | Ile | Met | Leu |
| | | | 275 | | | | | 280 | | | | | 285 | | |
| Gly | Asp | Glu | Ala | Ala | Leu | Leu | Glu | Gln | Lys | Glu | Leu | Leu | Ser | Asn | Trp |
| | 290 | | | | | 295 | | | | | 300 | | | | |
| Tyr | His | Phe | Leu | Val | Thr | Arg | Leu | Leu | Tyr | Ser | Asn | Pro | Thr | Val | Lys |
| 305 | | | | | 310 | | | | | 315 | | | | | 320 |
| Pro | Ile | Asp | Leu | His | Tyr | Tyr | Ala | Gln | Ser | Ser | Leu | Asp | Leu | Phe | Leu |
| | | | | 325 | | | | | 330 | | | | | 335 | |

```
Gly Gly Glu Ser Ser Pro Glu Pro Leu Asp Asn Ile Leu Leu Ala Ala
            340                 345                 350

Phe Glu Phe Asp Ile His Gln Val Ile Lys Glu Cys Ser Ile Ala Leu
            355                 360                 365

Ser Asn Trp Trp Phe Val Ala His Leu Thr Asp Leu Leu Asp His Cys
    370                 375                 380

Lys Leu Leu Gln Ser His Asn Leu Tyr Phe Gly Ser Asn Met Arg Glu
385                 390                 395                 400

Phe Leu Leu Leu Glu Tyr Ala Ser Gly Leu Phe Ala His Pro Ser Leu
                405                 410                 415

Trp Gln Leu Gly Val Asp Tyr Phe Asp Tyr Cys Pro Glu Leu Gly Arg
            420                 425                 430

Val Ser Leu Glu Leu His Ile Glu Arg Ile Pro Leu Asn Thr Glu Gln
            435                 440                 445

Lys Ala Leu Lys Val Leu Arg Ile Cys Glu Gln Arg Gln Met Thr Glu
    450                 455                 460

Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
                485                 490                 495

Ala Phe Ala Thr Leu Val Ser Asp Arg Phe Leu Arg Asp Tyr Cys Glu
            500                 505                 510

Arg Gly Cys Phe Ser Asp Leu Asp Leu Ile Asp Asn Leu Gly Pro Ala
            515                 520                 525

Met Met Leu Ser Asp Arg Leu Thr Phe Leu Gly Lys Tyr Arg Glu Phe
    530                 535                 540

His Arg Met Tyr Gly Glu Lys Arg Phe Ala Asp Ala Ala Ser Leu Leu
545                 550                 555                 560

Leu Ser Leu Met Thr Ser Arg Ile Ala Pro Arg Ser Phe Trp Met Thr
                565                 570                 575

Leu Leu Thr Asp Ala Leu Pro Leu Leu Glu Gln Lys Gln Asn Arg Leu
            580                 585                 590

Met Ser

<210> SEQ ID NO 25
<211> LENGTH: 1893
<212> TYPE: DNA
<213> ORGANISM: Homo sapiens
<220> FEATURE:
<221> NAME/KEY: CDS
<222> LOCATION: (1)..(1893)

<400> SEQUENCE: 25 atg gag gag ctc gat ggc gag cca aca gtc act ttg att cca ggc gtg     48
Met Glu Glu Leu Asp Gly Glu Pro Thr Val Thr Leu Ile Pro Gly Val
 1               5                   10                  15 aat tcc aag aag aac caa atg tat ttt gac tgg ggt cca ggg gag atg     96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg    144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac    192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg    240
```

```
                Ser Gln Ile Leu Arg Lys Leu Phe Asn Glu Ser His Gly Ile Phe Leu
                 65                  70                  75                  80 ggc ctc cag aga att gac gaa gag ttg act gga aaa tcc aga aaa tct       288
Gly Leu Gln Arg Ile Asp Glu Glu Leu Thr Gly Lys Ser Arg Lys Ser
             85                  90                  95 caa ttg gtt cga gtg agt aaa aac tac cga tca gtc atc aga gca tgt       336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat       384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc       432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc       480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag       528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa       576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg       624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc       672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg       720
Ala Ser Ala Gly Ile Cys Arg Ile Met Gly Asp Leu Met Arg Thr Met
225                 230                 235                 240 ccc att ctt agt cct ggg aac acc cag aca ctg aca gag ctg gag ctg       768
Pro Ile Leu Ser Pro Gly Asn Thr Gln Thr Leu Thr Glu Leu Glu Leu
                245                 250                 255 aag tgg cag cac tgg cac gag gaa tgt gag cgg tac ctc cag gac agc       816
Lys Trp Gln His Trp His Glu Glu Cys Glu Arg Tyr Leu Gln Asp Ser
            260                 265                 270 aca ttc gcc acc agc cct cac ctg gag tct ctc ttg aag att atg ctg       864
Thr Phe Ala Thr Ser Pro His Leu Glu Ser Leu Leu Lys Ile Met Leu
        275                 280                 285 gga gac gaa gct gcc ttg tta gag cag aag gaa ctt ctg agt aat tgg       912
Gly Asp Glu Ala Ala Leu Leu Glu Gln Lys Glu Leu Leu Ser Asn Trp
    290                 295                 300 tat cat ttc cta gtg act cgg ctc ttg tac tcc aat ccc aca gta aaa       960
Tyr His Phe Leu Val Thr Arg Leu Leu Tyr Ser Asn Pro Thr Val Lys
305                 310                 315                 320 ccc att gat ctg cac tac tat gcc cag tcc agc ctg gac ctg ttt ctg      1008
Pro Ile Asp Leu His Tyr Tyr Ala Gln Ser Ser Leu Asp Leu Phe Leu
                325                 330                 335 gga ggt gag agc agc cca gaa ccc ctg gac aac atc ttg ttg gca gcc      1056
Gly Gly Glu Ser Ser Pro Glu Pro Leu Asp Asn Ile Leu Leu Ala Ala
            340                 345                 350 ttt gag ttt gac atc cat caa gta atc aaa gag tgc agc atc gcc ctg      1104
Phe Glu Phe Asp Ile His Gln Val Ile Lys Glu Cys Ser Ile Ala Leu
        355                 360                 365 agc aac tgg tgg ttt gtg gcc cac ctg aca gac ctg ctg gac cac tgc      1152
Ser Asn Trp Trp Phe Val Ala His Leu Thr Asp Leu Leu Asp His Cys
    370                 375                 380
```

```
aag ctc ctc cag tca cac aac ctc tat ttc ggt tcc aac atg aga gag     1200
Lys Leu Leu Gln Ser His Asn Leu Tyr Phe Gly Ser Asn Met Arg Glu
385                 390                 395                 400 ttc ctc ctg ctg gag tac gcc tcg gga ctg ttt gct cat ccc agc ctg     1248
Phe Leu Leu Leu Glu Tyr Ala Ser Gly Leu Phe Ala His Pro Ser Leu
                405                 410                 415 tgg cag ctg ggg gtc gat tac ttt gat tac tgc ccc gag ctg ggc cga     1296
Trp Gln Leu Gly Val Asp Tyr Phe Asp Tyr Cys Pro Glu Leu Gly Arg
            420                 425                 430 gtc tcc ctg gag ctg cac att gag cgg ata cct ctg aac acc gag cag     1344
Val Ser Leu Glu Leu His Ile Glu Arg Ile Pro Leu Asn Thr Glu Gln
        435                 440                 445 aaa gcc ctg aag gtg ctg cgg atc tgt gag cag cgg cag atg act gaa     1392
Lys Ala Leu Lys Val Leu Arg Ile Cys Glu Gln Arg Gln Met Thr Glu
    450                 455                 460 caa gtt cgc agc att tgt aag atc tta gcc atg aaa gcc gtc cgc aac     1440
Gln Val Arg Ser Ile Cys Lys Ile Leu Ala Met Lys Ala Val Arg Asn
465                 470                 475                 480 aat cgc ctg ggt tct gcc ctc tct tgg agc atc cgt gct aag gat gcc     1488
Asn Arg Leu Gly Ser Ala Leu Ser Trp Ser Ile Arg Ala Lys Asp Ala
                485                 490                 495 gcc ttt gcc acg ctc gtg tca gac agg ttc ctc agg gat tac tgt gag     1536
Ala Phe Ala Thr Leu Val Ser Asp Arg Phe Leu Arg Asp Tyr Cys Glu
            500                 505                 510 cga ggc tgc ttt tct gat ttg gat ctc att gac aac ctg ggg cca gcc     1584
Arg Gly Cys Phe Ser Asp Leu Asp Leu Ile Asp Asn Leu Gly Pro Ala
        515                 520                 525 atg atg ctc agt gac cga ctg aca ttc ctg gga aag tat cgc gag ttc     1632
Met Met Leu Ser Asp Arg Leu Thr Phe Leu Gly Lys Tyr Arg Glu Phe
    530                 535                 540 cac cgt atg tac ggg gag aag cgt ttt gcc gac gca gct tct ctc ctt     1680
His Arg Met Tyr Gly Glu Lys Arg Phe Ala Asp Ala Ala Ser Leu Leu
545                 550                 555                 560 ctg tcc ttg atg acg tct cgg att gcc cct cgg tct ttc tgg atg act     1728
Leu Ser Leu Met Thr Ser Arg Ile Ala Pro Arg Ser Phe Trp Met Thr
                565                 570                 575 ctg ctg aca gat gcc ttg ccc ctt ttg gaa cag aaa cag gtg aag gtt     1776
Leu Leu Thr Asp Ala Leu Pro Leu Leu Glu Gln Lys Gln Val Lys Val
            580                 585                 590 gca gca gca gtg gtt ttc ttt gct tgt cag tcc ctg cta gag ctt agt     1824
Ala Ala Ala Val Val Phe Phe Ala Cys Gln Ser Leu Leu Glu Leu Ser
        595                 600                 605 tgt ata gct gtt gcc gat gtg cgt gtt tcc tcc ttt gtc gtt ctg cct     1872
Cys Ile Ala Val Ala Asp Val Arg Val Ser Ser Phe Val Val Leu Pro
    610                 615                 620 gtg cgc gtg tat tcc cct tag                                         1893
Val Arg Val Tyr Ser Pro
625                 630

<210> SEQ ID NO 26
<211> LENGTH: 630
<212> TYPE: PRT
<213> ORGANISM: Homo sapiens

<400> SEQUENCE: 26

Met Glu Glu Leu Asp Gly Glu Pro Thr Val Thr Leu Ile Pro Gly Val
  1               5                  10                  15

Asn Ser Lys Lys Asn Gln Met Tyr Phe Asp Trp Gly Pro Gly Glu Met
                 20                  25                  30

Leu Val Cys Glu Thr Ser Phe Asn Lys Lys Glu Lys Ser Glu Met Val
```

-continued

```
                35                  40                  45
Pro Ser Cys Pro Phe Ile Tyr Ile Ile Arg Lys Asp Val Asp Val Tyr
        50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
                100                 105                 110

Met Glu Glu Met His Gln Val Ala Ile Ala Ala Lys Asp Pro Ala Asn
                115                 120                 125

Gly Arg Gln Phe Ser Ser Gln Val Ser Ile Leu Ser Ala Met Glu Leu
        130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
                180                 185                 190

His Asp Ser Phe Trp Asn Leu Val Thr Ile Leu Val Leu Gln Gly Arg
                195                 200                 205

Leu Asp Glu Ala Arg Gln Met Leu Ser Lys Glu Ala Asp Ala Ser Pro
        210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
                260                 265                 270

Thr Phe Ala Thr Ser Pro His Leu Glu Ser Leu Leu Lys Ile Met Leu
                275                 280                 285

Gly Asp Glu Ala Ala Leu Leu Glu Gln Lys Glu Leu Leu Ser Asn Trp
        290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Ser Ser Leu Asp Leu Phe Leu
                325                 330                 335

Gly Gly Glu Ser Ser Pro Glu Pro Leu Asp Asn Ile Leu Leu Ala Ala
                340                 345                 350

Phe Glu Phe Asp Ile His Gln Val Ile Lys Glu Cys Ser Ile Ala Leu
                355                 360                 365

Ser Asn Trp Trp Phe Val Ala His Leu Thr Asp Leu Leu Asp His Cys
        370                 375                 380

Lys Leu Leu Gln Ser His Asn Leu Tyr Phe Gly Ser Asn Met Arg Glu
385                 390                 395                 400

Phe Leu Leu Leu Glu Tyr Ala Ser Gly Leu Phe Ala His Pro Ser Leu
                405                 410                 415

Trp Gln Leu Gly Val Asp Tyr Phe Asp Tyr Cys Pro Glu Leu Gly Arg
                420                 425                 430

Val Ser Leu Glu Leu His Ile Glu Arg Ile Pro Leu Asn Thr Glu Gln
                435                 440                 445

Lys Ala Leu Lys Val Leu Arg Ile Cys Glu Gln Arg Gln Met Thr Glu
        450                 455                 460
```

```
Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
            485                 490                 495

Ala Phe Ala Thr Leu Val Ser Asp Arg Phe Leu Arg Asp Tyr Cys Glu
            500                 505                 510

Arg Gly Cys Phe Ser Asp Leu Asp Leu Ile Asp Asn Leu Gly Pro Ala
            515                 520                 525

Met Met Leu Ser Asp Arg Leu Thr Phe Leu Gly Lys Tyr Arg Glu Phe
    530                 535                 540

His Arg Met Tyr Gly Glu Lys Arg Phe Ala Asp Ala Ala Ser Leu Leu
545                 550                 555                 560

Leu Ser Leu Met Thr Ser Arg Ile Ala Pro Arg Ser Phe Trp Met Thr
                565                 570                 575

Leu Leu Thr Asp Ala Leu Pro Leu Leu Glu Gln Lys Gln Val Lys Val
            580                 585                 590

Ala Ala Ala Val Val Phe Phe Ala Cys Gln Ser Leu Leu Glu Leu Ser
            595                 600                 605

Cys Ile Ala Val Ala Asp Val Arg Val Ser Ser Phe Val Val Leu Pro
        610                 615                 620

Val Arg Val Tyr Ser Pro
625                 630

<210> SEQ ID NO 27
<211> LENGTH: 1701
<212> TYPE: DNA
<213> ORGANISM: Homo sapiens
<220> FEATURE:
<221> NAME/KEY: CDS
<222> LOCATION: (1)..(1701)

<400> SEQUENCE: 27 atg gag gag ctc gat ggc gag cca aca gtc act ttg att cca ggc gtg      48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
        115                 120                 125 ggc cgc cag ttc agc agc cag gtg acc atc ttg gtg ctg cag ggc cgg     432
Gly Arg Gln Phe Ser Ser Gln Val Thr Ile Leu Val Leu Gln Gly Arg
```

```
            130                 135                 140
ctg gat gag gcc cga cag atg ctc tcc aag gaa gcc gat gcc agc ccc      480
Leu Asp Glu Ala Arg Gln Met Leu Ser Lys Glu Ala Asp Ala Ser Pro
145                 150                 155                 160 gcc tct gca ggc ata tgc cga atc atg ggg gac ctg atg agg aca atg      528
Ala Ser Ala Gly Ile Cys Arg Ile Met Gly Asp Leu Met Arg Thr Met
                165                 170                 175 ccc att ctt agt cct ggg aac acc cag aca ctg aca gag ctg gag ctg      576
Pro Ile Leu Ser Pro Gly Asn Thr Gln Thr Leu Thr Glu Leu Glu Leu
            180                 185                 190 aag tgg cag cac tgg cac gag gaa tgt gag cgg tac ctc cag gac agc      624
Lys Trp Gln His Trp His Glu Glu Cys Glu Arg Tyr Leu Gln Asp Ser
        195                 200                 205 aca ttc gcc acc agc cct cac ctg gag tct ctc ttg aag att atg ctg      672
Thr Phe Ala Thr Ser Pro His Leu Glu Ser Leu Leu Lys Ile Met Leu
    210                 215                 220 gga gac gaa gct gcc ttg tta gag cag aag gaa ctt ctg agt aat tgg      720
Gly Asp Glu Ala Ala Leu Leu Glu Gln Lys Glu Leu Leu Ser Asn Trp
225                 230                 235                 240 tat cat ttc cta gtg act cgg ctc ttg tac tcc aat ccc aca gta aaa      768
Tyr His Phe Leu Val Thr Arg Leu Leu Tyr Ser Asn Pro Thr Val Lys
                245                 250                 255 ccc att gat ctg cac tac tat gcc cag tcc agc ctg gac ctg ttt ctg      816
Pro Ile Asp Leu His Tyr Tyr Ala Gln Ser Ser Leu Asp Leu Phe Leu
            260                 265                 270 gga ggt gag agc agc cca gaa ccc ctg gac aac atc ttg ttg gca gcc      864
Gly Gly Glu Ser Ser Pro Glu Pro Leu Asp Asn Ile Leu Leu Ala Ala
        275                 280                 285 ttt gag ttt gac atc cat caa gta atc aaa gag tgc agc atc gcc ctg      912
Phe Glu Phe Asp Ile His Gln Val Ile Lys Glu Cys Ser Ile Ala Leu
    290                 295                 300 agc aac tgg tgg ttt gtg gcc cac ctg aca gac ctg ctg gac cac tgc      960
Ser Asn Trp Trp Phe Val Ala His Leu Thr Asp Leu Leu Asp His Cys
305                 310                 315                 320 aag ctc ctc cag tca cac aac ctc tat ttc ggt tcc aac atg aga gag      1008
Lys Leu Leu Gln Ser His Asn Leu Tyr Phe Gly Ser Asn Met Arg Glu
                325                 330                 335 ttc ctc ctg ctg gag tac gcc tcg gga ctg ttt gct cat ccc agc ctg      1056
Phe Leu Leu Leu Glu Tyr Ala Ser Gly Leu Phe Ala His Pro Ser Leu
            340                 345                 350 tgg cag ctg ggg gtc gat tac ttt gat tac tgc ccc gag ctg ggc cga      1104
Trp Gln Leu Gly Val Asp Tyr Phe Asp Tyr Cys Pro Glu Leu Gly Arg
        355                 360                 365 gtc tcc ctg gag ctg cac att gag cgg ata cct ctg aac acc gag cag      1152
Val Ser Leu Glu Leu His Ile Glu Arg Ile Pro Leu Asn Thr Glu Gln
    370                 375                 380 aaa gcc ctg aag gtg ctg cgg atc tgt gag cag cgg cag atg act gaa      1200
Lys Ala Leu Lys Val Leu Arg Ile Cys Glu Gln Arg Gln Met Thr Glu
385                 390                 395                 400 caa gtt cgc agc att tgt aag atc tta gcc atg aaa gcc gtc cgc aac      1248
Gln Val Arg Ser Ile Cys Lys Ile Leu Ala Met Lys Ala Val Arg Asn
                405                 410                 415 aat cgc ctg ggt tct gcc ctc tct tgg agc atc cgt gct aag gat gcc      1296
Asn Arg Leu Gly Ser Ala Leu Ser Trp Ser Ile Arg Ala Lys Asp Ala
            420                 425                 430 gcc ttt gcc acg ctc gtg tca gac agg ttc ctc agg gat tac tgt gag      1344
Ala Phe Ala Thr Leu Val Ser Asp Arg Phe Leu Arg Asp Tyr Cys Glu
        435                 440                 445 cga ggc tgc ttt tct gat ttg gat ctc att gac aac ctg ggg cca gcc      1392
```

```
Arg Gly Cys Phe Ser Asp Leu Asp Leu Ile Asp Asn Leu Gly Pro Ala
    450                 455                 460 atg atg ctc agt gac cga ctg aca ttc ctg gga aag tat cgc gag ttc      1440
Met Met Leu Ser Asp Arg Leu Thr Phe Leu Gly Lys Tyr Arg Glu Phe
465                 470                 475                 480 cac cgt atg tac ggg gag aag cgt ttt gca gac gca gct tct ctc ctt      1488
His Arg Met Tyr Gly Glu Lys Arg Phe Ala Asp Ala Ala Ser Leu Leu
                485                 490                 495 ctg tcc ttg atg acg tct cgg att gcc cct cgg tct ttc tgg atg act      1536
Leu Ser Leu Met Thr Ser Arg Ile Ala Pro Arg Ser Phe Trp Met Thr
        500                 505                 510 ctg ctg aca gat gcc ttg ccc ctt ttg gaa cag aaa cag gtg aag gtt      1584
Leu Leu Thr Asp Ala Leu Pro Leu Leu Glu Gln Lys Gln Val Lys Val
    515                 520                 525 gca gca gca gtg gtt ttc ttt gct tgt cag tcc ctg cta gag ctt agt      1632
Ala Ala Ala Val Val Phe Phe Ala Cys Gln Ser Leu Leu Glu Leu Ser
530                 535                 540 tgt ata gct gtt gcc gat gtg cgt gtt tcc tcc ttt gtc gtt ctg cct      1680
Cys Ile Ala Val Ala Asp Val Arg Val Ser Ser Phe Val Val Leu Pro
545                 550                 555                 560 gtg cgc gtg tat tcc cct tag                                          1701
Val Arg Val Tyr Ser Pro
                565

<210> SEQ ID NO 28
<211> LENGTH: 566
<212> TYPE: PRT
<213> ORGANISM: Homo sapiens

<400> SEQUENCE: 28

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
                20                  25                  30

Leu Val Cys Glu Thr Ser Phe Asn Lys Lys Glu Lys Ser Glu Met Val
            35                  40                  45

Pro Ser Cys Pro Phe Ile Tyr Ile Ile Arg Lys Asp Val Asp Val Tyr
        50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Thr Ile Leu Val Leu Gln Gly Arg
    130                 135                 140

Leu Asp Glu Ala Arg Gln Met Leu Ser Lys Glu Ala Asp Ala Ser Pro
145                 150                 155                 160

Ala Ser Ala Gly Ile Cys Arg Ile Met Gly Asp Leu Met Arg Thr Met
                165                 170                 175

Pro Ile Leu Ser Pro Gly Asn Thr Gln Thr Leu Thr Glu Leu Glu Leu
            180                 185                 190

Lys Trp Gln His Trp His Glu Glu Cys Glu Arg Tyr Leu Gln Asp Ser
        195                 200                 205

Thr Phe Ala Thr Ser Pro His Leu Glu Ser Leu Leu Lys Ile Met Leu
```

```
                  210                 215                 220
Gly Asp Glu Ala Ala Leu Leu Glu Gln Lys Glu Leu Leu Ser Asn Trp
225                 230                 235                 240

Tyr His Phe Leu Val Thr Arg Leu Leu Tyr Ser Asn Pro Thr Val Lys
                245                 250                 255

Pro Ile Asp Leu His Tyr Tyr Ala Gln Ser Ser Leu Asp Leu Phe Leu
                260                 265                 270

Gly Gly Glu Ser Ser Pro Glu Pro Leu Asp Asn Ile Leu Leu Ala Ala
                275                 280                 285

Phe Glu Phe Asp Ile His Gln Val Ile Lys Glu Cys Ser Ile Ala Leu
290                 295                 300

Ser Asn Trp Trp Phe Val Ala His Leu Thr Asp Leu Leu Asp His Cys
305                 310                 315                 320

Lys Leu Leu Gln Ser His Asn Leu Tyr Phe Gly Ser Asn Met Arg Glu
                325                 330                 335

Phe Leu Leu Glu Tyr Ala Ser Gly Leu Phe Ala His Pro Ser Leu
                340                 345                 350

Trp Gln Leu Gly Val Asp Tyr Phe Asp Tyr Cys Pro Glu Leu Gly Arg
                355                 360                 365

Val Ser Leu Glu Leu His Ile Glu Arg Ile Pro Leu Asn Thr Glu Gln
370                 375                 380

Lys Ala Leu Lys Val Leu Arg Ile Cys Glu Gln Arg Gln Met Thr Glu
385                 390                 395                 400

Gln Val Arg Ser Ile Cys Lys Ile Leu Ala Met Lys Ala Val Arg Asn
                405                 410                 415

Asn Arg Leu Gly Ser Ala Leu Ser Trp Ser Ile Arg Ala Lys Asp Ala
                420                 425                 430

Ala Phe Ala Thr Leu Val Ser Asp Arg Phe Leu Arg Asp Tyr Cys Glu
                435                 440                 445

Arg Gly Cys Phe Ser Asp Leu Asp Leu Ile Asp Asn Leu Gly Pro Ala
                450                 455                 460

Met Met Leu Ser Asp Arg Leu Thr Phe Leu Gly Lys Tyr Arg Glu Phe
465                 470                 475                 480

His Arg Met Tyr Gly Glu Lys Arg Phe Ala Asp Ala Ala Ser Leu Leu
                485                 490                 495

Leu Ser Leu Met Thr Ser Arg Ile Ala Pro Arg Ser Phe Trp Met Thr
                500                 505                 510

Leu Leu Thr Asp Ala Leu Pro Leu Leu Glu Gln Lys Gln Val Lys Val
                515                 520                 525

Ala Ala Ala Val Val Phe Phe Ala Cys Gln Ser Leu Leu Glu Leu Ser
                530                 535                 540

Cys Ile Ala Val Ala Asp Val Arg Val Ser Ser Phe Val Val Leu Pro
545                 550                 555                 560

Val Arg Val Tyr Ser Pro
                565

<210> SEQ ID NO 29
<211> LENGTH: 531
<212> TYPE: DNA
<213> ORGANISM: Homo sapiens
<220> FEATURE:
<221> NAME/KEY: CDS
<222> LOCATION: (1)..(531)

<400> SEQUENCE: 29
```

| | | | | | | | | | | | | | | | | |
|---|---|---|---|---|---|---|---|---|---|---|---|---|---|---|---|---|
| atg | gag | gag | ctc | gat | ggc | gag | cca | aca | gtc | act | ttg | att | cca | ggc | gtg | 48 |
| Met | Glu | Glu | Leu | Asp | Gly | Glu | Pro | Thr | Val | Thr | Leu | Ile | Pro | Gly | Val | |
| 1 | | | | 5 | | | | | 10 | | | | | 15 | | |
| aat | tcc | aag | aag | aac | caa | atg | tat | ttt | gac | tgg | ggt | cca | ggg | gag | atg | 96 |
| Asn | Ser | Lys | Lys | Asn | Gln | Met | Tyr | Phe | Asp | Trp | Gly | Pro | Gly | Glu | Met | |
| | | | 20 | | | | | 25 | | | | | 30 | | | |
| ctg | gta | tgt | gaa | acc | tcc | ttc | aac | aaa | aaa | gaa | aaa | tca | gag | atg | gtg | 144 |
| Leu | Val | Cys | Glu | Thr | Ser | Phe | Asn | Lys | Lys | Glu | Lys | Ser | Glu | Met | Val | |
| | | 35 | | | | | 40 | | | | | 45 | | | | |
| cca | agt | tgc | ccc | ttt | atc | tat | atc | atc | cgt | aag | gat | gta | gat | gtt | tac | 192 |
| Pro | Ser | Cys | Pro | Phe | Ile | Tyr | Ile | Ile | Arg | Lys | Asp | Val | Asp | Val | Tyr | |
| 50 | | | | | 55 | | | | | 60 | | | | | | |
| tct | caa | atc | ttg | aga | aaa | ctc | ttc | aat | gaa | tcc | cat | gga | atc | ttt | ctg | 240 |
| Ser | Gln | Ile | Leu | Arg | Lys | Leu | Phe | Asn | Glu | Ser | His | Gly | Ile | Phe | Leu | |
| 65 | | | | | 70 | | | | | 75 | | | | | 80 | |
| ggc | ctc | cag | aga | att | gac | gaa | gag | ttg | act | gga | aaa | tcc | aga | aaa | tct | 288 |
| Gly | Leu | Gln | Arg | Ile | Asp | Glu | Glu | Leu | Thr | Gly | Lys | Ser | Arg | Lys | Ser | |
| | | | | 85 | | | | | 90 | | | | | 95 | | |
| caa | ttg | gtt | cga | gtg | agt | aaa | aac | tac | cga | tca | gtc | atc | aga | gca | tgt | 336 |
| Gln | Leu | Val | Arg | Val | Ser | Lys | Asn | Tyr | Arg | Ser | Val | Ile | Arg | Ala | Cys | |
| | | | | 100 | | | | | 105 | | | | | 110 | | |
| atg | gag | gaa | atg | cac | cag | gtt | gca | att | gct | gct | aaa | gat | cca | gcc | aat | 384 |
| Met | Glu | Glu | Met | His | Gln | Val | Ala | Ile | Ala | Ala | Lys | Asp | Pro | Ala | Asn | |
| | | | 115 | | | | | 120 | | | | | 125 | | | |
| ggc | cgc | cag | ttc | agc | agc | cag | ctg | gcc | ctc | tcc | tcc | tcc | atc | tcc | ttg | 432 |
| Gly | Arg | Gln | Phe | Ser | Ser | Gln | Leu | Ala | Leu | Ser | Ser | Ser | Ile | Ser | Leu | |
| | | 130 | | | | | 135 | | | | | 140 | | | | |
| act | ggg | tcc | ggc | tcc | atg | tgt | gcg | agg | tgg | aca | gtt | tgt | cgg | cag | atg | 480 |
| Thr | Gly | Ser | Gly | Ser | Met | Cys | Ala | Arg | Trp | Thr | Val | Cys | Arg | Gln | Met | |
| 145 | | | | | 150 | | | | | 155 | | | | | 160 | |
| ttc | tgg | gca | gtg | aga | atc | caa | gca | aac | atg | aca | gct | tct | gga | act | tgg | 528 |
| Phe | Trp | Ala | Val | Arg | Ile | Gln | Ala | Asn | Met | Thr | Ala | Ser | Gly | Thr | Trp | |
| | | | | 165 | | | | | 170 | | | | | 175 | | |
| tga | | | | | | | | | | | | | | | | 531 |

<210> SEQ ID NO 30
<211> LENGTH: 176
<212> TYPE: PRT
<213> ORGANISM: Homo sapiens

<400> SEQUENCE: 30

Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Leu Ala Leu Ser Ser Ser Ile Ser Leu

|   |   |   |   | 130 |   |   |   | 135 |   |   |   | 140 |   |   |
|---|---|---|---|---|---|---|---|---|---|---|---|---|---|---|
| Thr | Gly | Ser | Gly | Ser | Met | Cys | Ala | Arg | Trp | Thr | Val | Cys | Arg | Gln | Met |
| 145 |   |   |   | 150 |   |   |   | 155 |   |   |   | 160 |

| Phe | Trp | Ala | Val | Arg | Ile | Gln | Ala | Asn | Met | Thr | Ala | Ser | Gly | Thr | Trp |
|---|---|---|---|---|---|---|---|---|---|---|---|---|---|---|---|
|   |   |   |   | 165 |   |   |   | 170 |   |   |   | 175 |

<210> SEQ ID NO 31
<211> LENGTH: 858
<212> TYPE: DNA
<213> ORGANISM: Homo sapiens
<220> FEATURE:
<221> NAME/KEY: CDS
<222> LOCATION: (1)..(858)

<400> SEQUENCE: 31

```
atg gag gag ctc gat ggc gag cca aca gtc act ttg att cca ggc gtg        48
Met Glu Glu Leu Asp Gly Glu Pro Thr Val Thr Leu Ile Pro Gly Val
 1               5                  10                  15 aat tcc aag aag aac caa atg tat ttt gac tgg ggt cca ggg gag atg        96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg       144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac       192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg       240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct       288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt       336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat       384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc       432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc       480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag       528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa       576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg       624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc       672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg       720
Ala Ser Ala Gly Ile Cys Arg Ile Met Gly Asp Leu Met Arg Thr Met
225                 230                 235                 240
```

```
ccc att ctt agt cct ggg aac acc cag aca ctg aca gag ctg gag ctg      768
Pro Ile Leu Ser Pro Gly Asn Thr Gln Thr Leu Thr Glu Leu Glu Leu
            245                 250                 255 aag tgg cag cac tgg cac gag gaa tgt gag cgg tac ctc cag gac agc      816
Lys Trp Gln His Trp His Glu Glu Cys Glu Arg Tyr Leu Gln Asp Ser
        260                 265                 270 aca ttc gcc acc agc cct cac ctg gag tct ctc ttg aag taa              858
Thr Phe Ala Thr Ser Pro His Leu Glu Ser Leu Leu Lys
275                 280                 285
```

<210> SEQ ID NO 32
<211> LENGTH: 285
<212> TYPE: PRT
<213> ORGANISM: Homo sapiens

<400> SEQUENCE: 32

```
Met Glu Glu Leu Asp Gly Glu Pro Thr Val Thr Leu Ile Pro Gly Val
1               5                   10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys
        275                 280                 285
```

<210> SEQ ID NO 33
<211> LENGTH: 1557
<212> TYPE: DNA
<213> ORGANISM: Homo sapiens

<220> FEATURE:
<221> NAME/KEY: CDS
<222> LOCATION: (1)..(1557)

<400> SEQUENCE: 33

| | | | | | | | | | | | | | | | | |
|---|---|---|---|---|---|---|---|---|---|---|---|---|---|---|---|---|
| atg | gag | gag | ctc | gat | ggc | gag | cca | aca | gtc | act | ttg | att | cca | ggc | gtg | 48 |
| Met | Glu | Glu | Leu | Asp | Gly | Glu | Pro | Thr | Val | Thr | Leu | Ile | Pro | Gly | Val | |
| 1 | | | | 5 | | | | | 10 | | | | | 15 | | |
| aat | tcc | aag | aag | aac | caa | atg | tat | ttt | gac | tgg | ggt | cca | ggg | gag | atg | 96 |
| Asn | Ser | Lys | Lys | Asn | Gln | Met | Tyr | Phe | Asp | Trp | Gly | Pro | Gly | Glu | Met | |
| | | | 20 | | | | | 25 | | | | | 30 | | | |
| ctg | gta | tgt | gaa | acc | tcc | ttc | aac | aaa | aaa | gaa | aaa | tca | gag | atg | gtg | 144 |
| Leu | Val | Cys | Glu | Thr | Ser | Phe | Asn | Lys | Lys | Glu | Lys | Ser | Glu | Met | Val | |
| | | 35 | | | | | 40 | | | | | 45 | | | | |
| cca | agt | tgc | ccc | ttt | atc | tat | atc | atc | cgt | aag | gat | gta | gat | gtt | tac | 192 |
| Pro | Ser | Cys | Pro | Phe | Ile | Tyr | Ile | Ile | Arg | Lys | Asp | Val | Asp | Val | Tyr | |
| | 50 | | | | | 55 | | | | | 60 | | | | | |
| tct | caa | atc | ttg | aga | aaa | ctc | ttc | aat | gaa | tcc | cat | gga | atc | ttt | ctg | 240 |
| Ser | Gln | Ile | Leu | Arg | Lys | Leu | Phe | Asn | Glu | Ser | His | Gly | Ile | Phe | Leu | |
| 65 | | | | | 70 | | | | | 75 | | | | | 80 | |
| ggc | ctc | cag | aga | att | gac | gaa | gag | ttg | act | gga | aaa | tcc | aga | aaa | tct | 288 |
| Gly | Leu | Gln | Arg | Ile | Asp | Glu | Glu | Leu | Thr | Gly | Lys | Ser | Arg | Lys | Ser | |
| | | | | 85 | | | | | 90 | | | | | 95 | | |
| caa | ttg | gtt | cga | gtg | agt | aaa | aac | tac | cga | tca | gtc | atc | aga | gca | tgt | 336 |
| Gln | Leu | Val | Arg | Val | Ser | Lys | Asn | Tyr | Arg | Ser | Val | Ile | Arg | Ala | Cys | |
| | | | 100 | | | | | 105 | | | | | 110 | | | |
| atg | gag | gaa | atg | cac | cag | gtt | gca | att | gct | gct | aaa | gat | cca | gcc | aat | 384 |
| Met | Glu | Glu | Met | His | Gln | Val | Ala | Ile | Ala | Ala | Lys | Asp | Pro | Ala | Asn | |
| | | 115 | | | | | 120 | | | | | 125 | | | | |
| ggc | cgc | cag | ttc | agc | agc | cag | gtc | tcc | att | ttg | tca | gca | atg | gag | ctc | 432 |
| Gly | Arg | Gln | Phe | Ser | Ser | Gln | Val | Ser | Ile | Leu | Ser | Ala | Met | Glu | Leu | |
| | 130 | | | | | 135 | | | | | 140 | | | | | |
| atc | tgg | aac | ctg | tgt | gag | att | ctt | ttt | att | gaa | gtg | gcc | cca | gct | ggc | 480 |
| Ile | Trp | Asn | Leu | Cys | Glu | Ile | Leu | Phe | Ile | Glu | Val | Ala | Pro | Ala | Gly | |
| 145 | | | | | 150 | | | | | 155 | | | | | 160 | |
| cct | ctc | ctc | ctc | cat | ctc | ctt | gac | tgg | gtc | cgg | ctc | cat | gtg | tgc | gag | 528 |
| Pro | Leu | Leu | Leu | His | Leu | Leu | Asp | Trp | Val | Arg | Leu | His | Val | Cys | Glu | |
| | | | | 165 | | | | | 170 | | | | | 175 | | |
| gtg | gac | agt | ttg | tcg | gca | gat | gtt | ctg | ggc | agt | gag | aat | cca | agc | aaa | 576 |
| Val | Asp | Ser | Leu | Ser | Ala | Asp | Val | Leu | Gly | Ser | Glu | Asn | Pro | Ser | Lys | |
| | | | 180 | | | | | 185 | | | | | 190 | | | |
| cat | gac | agc | ttc | tgg | aac | ttg | gtg | acc | atc | ttg | gtg | ctg | cag | ggc | cgg | 624 |
| His | Asp | Ser | Phe | Trp | Asn | Leu | Val | Thr | Ile | Leu | Val | Leu | Gln | Gly | Arg | |
| | | 195 | | | | | 200 | | | | | 205 | | | | |
| ctg | gat | gag | gcc | cga | cag | atg | ctc | tcc | aag | gaa | gcc | gat | gcc | agc | ccc | 672 |
| Leu | Asp | Glu | Ala | Arg | Gln | Met | Leu | Ser | Lys | Glu | Ala | Asp | Ala | Ser | Pro | |
| | 210 | | | | | 215 | | | | | 220 | | | | | |
| gcc | tct | gca | ggc | ata | tgc | cga | atc | atg | ggg | gac | ctg | atg | agg | aca | atg | 720 |
| Ala | Ser | Ala | Gly | Ile | Cys | Arg | Ile | Met | Gly | Asp | Leu | Met | Arg | Thr | Met | |
| 225 | | | | | 230 | | | | | 235 | | | | | 240 | |
| ccc | att | ctt | agt | cct | ggg | aac | acc | cag | aca | ctg | aca | gag | ctg | gag | ctg | 768 |
| Pro | Ile | Leu | Ser | Pro | Gly | Asn | Thr | Gln | Thr | Leu | Thr | Glu | Leu | Glu | Leu | |
| | | | | 245 | | | | | 250 | | | | | 255 | | |
| aag | tgg | cag | cac | tgg | cac | gag | gaa | tgt | gag | cgg | tac | ctc | cag | gac | agc | 816 |
| Lys | Trp | Gln | His | Trp | His | Glu | Glu | Cys | Glu | Arg | Tyr | Leu | Gln | Asp | Ser | |
| | | | 260 | | | | | 265 | | | | | 270 | | | |
| aca | ttc | gcc | acc | agc | cct | cac | ctg | gag | tct | ctc | ttg | aag | att | atg | ctg | 864 |
| Thr | Phe | Ala | Thr | Ser | Pro | His | Leu | Glu | Ser | Leu | Leu | Lys | Ile | Met | Leu | |
| | | 275 | | | | | 280 | | | | | 285 | | | | |
| gga | gac | gaa | gct | gcc | ttg | tta | gag | cag | aag | gaa | ctt | ctg | agt | aat | tgg | 912 |

```
Gly Asp Glu Ala Ala Leu Leu Glu Gln Lys Glu Leu Leu Ser Asn Trp
    290                 295                 300 tat cat ttc cta gtg act cgg ctc ttg tac tcc aat ccc aca gta aaa            960
Tyr His Phe Leu Val Thr Arg Leu Leu Tyr Ser Asn Pro Thr Val Lys
305                 310                 315                 320 ccc att gat ctg cac tac tat gcc cag tcc agc ctg gac ctg ttt ctg          1008
Pro Ile Asp Leu His Tyr Tyr Ala Gln Ser Ser Leu Asp Leu Phe Leu
                325                 330                 335 gga ggt gag agc agc cca gaa ccc ctg gac aac atc ttg ttg gca gcc          1056
Gly Gly Glu Ser Ser Pro Glu Pro Leu Asp Asn Ile Leu Leu Ala Ala
            340                 345                 350 ttt gag ttt gac atc cat caa gta atc aaa gag tgc agc atc gcc ctg          1104
Phe Glu Phe Asp Ile His Gln Val Ile Lys Glu Cys Ser Ile Ala Leu
        355                 360                 365 agc aac tgg tgg ttt gtg gcc cac ctg aca gac ctg ctg gac cac tgc          1152
Ser Asn Trp Trp Phe Val Ala His Leu Thr Asp Leu Leu Asp His Cys
    370                 375                 380 aag ctc ctc cag tca cac aac ctc tat ttc ggt tcc aac atg aga gag          1200
Lys Leu Leu Gln Ser His Asn Leu Tyr Phe Gly Ser Asn Met Arg Glu
385                 390                 395                 400 ttc ctc ctg ctg gag tac gcc tcg gga ctg ttt gct cat ccc agc ctg          1248
Phe Leu Leu Leu Glu Tyr Ala Ser Gly Leu Phe Ala His Pro Ser Leu
                405                 410                 415 tgg cag ctg ggg gtc gat tac ttt gat tac tgc ccc gag ctg ggc cga          1296
Trp Gln Leu Gly Val Asp Tyr Phe Asp Tyr Cys Pro Glu Leu Gly Arg
            420                 425                 430 gtc tcc ctg gag ctg cac att gag cgg ata cct ctg aac acc gag cag          1344
Val Ser Leu Glu Leu His Ile Glu Arg Ile Pro Leu Asn Thr Glu Gln
        435                 440                 445 aaa gcc ctg aag gtg ctg cgg atc tgt gag cag cgg cag atg act gaa          1392
Lys Ala Leu Lys Val Leu Arg Ile Cys Glu Gln Arg Gln Met Thr Glu
    450                 455                 460 caa gtt cgc agc att tgt aag atc tta gcc atg aaa gcc gtc cgc aac          1440
Gln Val Arg Ser Ile Cys Lys Ile Leu Ala Met Lys Ala Val Arg Asn
465                 470                 475                 480 aat cgc ctg ggt tct gcc ctc tct tgg agc atc cgt gct aag gat gcc          1488
Asn Arg Leu Gly Ser Ala Leu Ser Trp Ser Ile Arg Ala Lys Asp Ala
                485                 490                 495 gcc ttt gcc acg ctc gtg tca gac agg tgg gtg ccg cta gtg ttg gct          1536
Ala Phe Ala Thr Leu Val Ser Asp Arg Trp Val Pro Leu Val Leu Ala
            500                 505                 510 tcc cag gga ctg ggt ggt tga                                              1557
Ser Gln Gly Leu Gly Gly
        515

<210> SEQ ID NO 34
<211> LENGTH: 518
<212> TYPE: PRT
<213> ORGANISM: Homo sapiens

<400> SEQUENCE: 34

Met Glu Glu Leu Asp Gly Glu Pro Thr Val Thr Leu Ile Pro Gly Val
  1               5                  10                  15

Asn Ser Lys Lys Asn Gln Met Tyr Phe Asp Trp Gly Pro Gly Glu Met
                20                  25                  30

Leu Val Cys Glu Thr Ser Phe Asn Lys Lys Glu Lys Ser Glu Met Val
            35                  40                  45

Pro Ser Cys Pro Phe Ile Tyr Ile Ile Arg Lys Asp Val Asp Val Tyr
        50                  55                  60
```

-continued

```
Ser Gln Ile Leu Arg Lys Leu Phe Asn Glu Ser His Gly Ile Phe Leu
 65                  70                  75                  80

Gly Leu Gln Arg Ile Asp Glu Glu Leu Thr Gly Lys Ser Arg Lys Ser
                 85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255

Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
        275                 280                 285

Gly Asp Glu Ala Ala Leu Leu Glu Gln Lys Glu Leu Leu Ser Asn Trp
    290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Ser Ser Leu Asp Leu Phe Leu
                325                 330                 335

Gly Gly Glu Ser Ser Pro Glu Pro Leu Asp Asn Ile Leu Leu Ala Ala
            340                 345                 350

Phe Glu Phe Asp Ile His Gln Val Ile Lys Glu Cys Ser Ile Ala Leu
        355                 360                 365

Ser Asn Trp Trp Phe Val Ala His Leu Thr Asp Leu Leu Asp His Cys
    370                 375                 380

Lys Leu Leu Gln Ser His Asn Leu Tyr Phe Gly Ser Asn Met Arg Glu
385                 390                 395                 400

Phe Leu Leu Leu Glu Tyr Ala Ser Gly Leu Phe Ala His Pro Ser Leu
                405                 410                 415

Trp Gln Leu Gly Val Asp Tyr Phe Asp Tyr Cys Pro Glu Leu Gly Arg
            420                 425                 430

Val Ser Leu Glu Leu His Ile Glu Arg Ile Pro Leu Asn Thr Glu Gln
        435                 440                 445

Lys Ala Leu Lys Val Leu Arg Ile Cys Glu Gln Arg Gln Met Thr Glu
    450                 455                 460

Gln Val Arg Ser Ile Cys Lys Ile Leu Ala Met Lys Ala Val Arg Asn
465                 470                 475                 480

Asn Arg Leu Gly Ser Ala Leu Ser Trp Ser Ile Arg Ala Lys Asp Ala
```

-continued

```
                485                 490                 495
Ala Phe Ala Thr Leu Val Ser Asp Arg Trp Val Pro Leu Val Leu Ala
            500                 505                 510

Ser Gln Gly Leu Gly Gly
        515

<210> SEQ ID NO 35
<211> LENGTH: 993
<212> TYPE: DNA
<213> ORGANISM: Homo sapiens
<220> FEATURE:
<221> NAME/KEY: CDS
<222> LOCATION: (1)..(993)

<400> SEQUENCE: 35 atg gag gag ctc gat ggc gag cca aca gtc act ttg att cca ggc gtg      48
Met Glu Glu Leu Asp Gly Glu Pro Thr Val Thr Leu Ile Pro Gly Val
  1               5                  10                  15 aat tcc aag aag aac caa atg tat ttt gac tgg ggt cca ggg gag atg      96
Asn Ser Lys Lys Asn Gln Met Tyr Phe Asp Trp Gly Pro Gly Glu Met
             20                  25                  30 ctg gta tgt gaa acc tcc ttc aac aaa aaa gaa aaa tca gag atg gtg     144
Leu Val Cys Glu Thr Ser Phe Asn Lys Lys Glu Lys Ser Glu Met Val
         35                  40                  45 cca agt tgc ccc ttt atc tat atc atc cgt aag gat gta gat gtt tac     192
Pro Ser Cys Pro Phe Ile Tyr Ile Ile Arg Lys Asp Val Asp Val Tyr
     50                  55                  60 tct caa atc ttg aga aaa ctc ttc aat gaa tcc cat gga atc ttt ctg     240
Ser Gln Ile Leu Arg Lys Leu Phe Asn Glu Ser His Gly Ile Phe Leu
 65                  70                  75                  80 ggc ctc cag aga att gac gaa gag ttg act gga aaa tcc aga aaa tct     288
Gly Leu Gln Arg Ile Asp Glu Glu Leu Thr Gly Lys Ser Arg Lys Ser
                 85                  90                  95 caa ttg gtt cga gtg agt aaa aac tac cga tca gtc atc aga gca tgt     336
Gln Leu Val Arg Val Ser Lys Asn Tyr Arg Ser Val Ile Arg Ala Cys
            100                 105                 110 atg gag gaa atg cac cag gtt gca att gct gct aaa gat cca gcc aat     384
Met Glu Glu Met His Gln Val Ala Ile Ala Ala Lys Asp Pro Ala Asn
        115                 120                 125 ggc cgc cag ttc agc agc cag gtc tcc att ttg tca gca atg gag ctc     432
Gly Arg Gln Phe Ser Ser Gln Val Ser Ile Leu Ser Ala Met Glu Leu
    130                 135                 140 atc tgg aac ctg tgt gag att ctt ttt att gaa gtg gcc cca gct ggc     480
Ile Trp Asn Leu Cys Glu Ile Leu Phe Ile Glu Val Ala Pro Ala Gly
145                 150                 155                 160 cct ctc ctc ctc cat ctc ctt gac tgg gtc cgg ctc cat gtg tgc gag     528
Pro Leu Leu Leu His Leu Leu Asp Trp Val Arg Leu His Val Cys Glu
                165                 170                 175 gtg gac agt ttg tcg gca gat gtt ctg ggc agt gag aat cca agc aaa     576
Val Asp Ser Leu Ser Ala Asp Val Leu Gly Ser Glu Asn Pro Ser Lys
            180                 185                 190 cat gac agc ttc tgg aac ttg gtg acc atc ttg gtg ctg cag ggc cgg     624
His Asp Ser Phe Trp Asn Leu Val Thr Ile Leu Val Leu Gln Gly Arg
        195                 200                 205 ctg gat gag gcc cga cag atg ctc tcc aag gaa gcc gat gcc agc ccc     672
Leu Asp Glu Ala Arg Gln Met Leu Ser Lys Glu Ala Asp Ala Ser Pro
    210                 215                 220 gcc tct gca ggc ata tgc cga atc atg ggg gac ctg atg agg aca atg     720
Ala Ser Ala Gly Ile Cys Arg Ile Met Gly Asp Leu Met Arg Thr Met
225                 230                 235                 240
```

```
ccc att ctt agt cct ggg aac acc cag aca ctg aca gag ctg gag ctg        768
Pro Ile Leu Ser Pro Gly Asn Thr Gln Thr Leu Thr Glu Leu Glu Leu
            245                 250                 255 aag tgg cag cac tgg cac gag gaa tgt gag cgg tac ctc cag gac agc        816
Lys Trp Gln His Trp His Glu Glu Cys Glu Arg Tyr Leu Gln Asp Ser
        260                 265                 270 aca ttc gcc acc agc cct cac ctg gag tct ctc ttg aag att atg ctg        864
Thr Phe Ala Thr Ser Pro His Leu Glu Ser Leu Leu Lys Ile Met Leu
    275                 280                 285 gga gac gaa gct gcc ttg tta gag cag aag gaa ctt ctg agt aat tgg        912
Gly Asp Glu Ala Ala Leu Leu Glu Gln Lys Glu Leu Leu Ser Asn Trp
290                 295                 300 tat cat ttc cta gtg act cgg ctc ttg tac tcc aat ccc aca gta aaa        960
Tyr His Phe Leu Val Thr Arg Leu Leu Tyr Ser Asn Pro Thr Val Lys
305                 310                 315                 320 ccc att gat ctg cac tac tat gcc cag gat tga                            993
Pro Ile Asp Leu His Tyr Tyr Ala Gln Asp
                325                 330

<210> SEQ ID NO 36
<211> LENGTH: 330
<212> TYPE: PRT
<213> ORGANISM: Homo sapiens

<400> SEQUENCE: 36

Met Glu Glu Leu Asp Gly Glu Pro Thr Val Thr Leu Ile Pro Gly Val
 1               5                  10                  15

Asn Ser Lys Lys Asn Gln Met Tyr Phe Asp Trp Gly Pro Gly Glu Met
            20                  25                  30

Leu Val Cys Glu Thr Ser Phe Asn Lys Lys Glu Lys Ser Glu Met Val
        35                  40                  45

Pro Ser Cys Pro Phe Ile Tyr Ile Ile Arg Lys Asp Val Asp Val Tyr
    50                  55                  60

Ser Gln Ile Leu Arg Lys Leu Phe Asn Glu Ser His Gly Ile Phe Leu
65                  70                  75                  80

Gly Leu Gln Arg Ile Asp Glu Glu Leu Thr Gly Lys Ser Arg Lys Ser
                85                  90                  95

Gln Leu Val Arg Val Ser Lys Asn Tyr Arg Ser Val Ile Arg Ala Cys
            100                 105                 110

Met Glu Glu Met His Gln Val Ala Ile Ala Ala Lys Asp Pro Ala Asn
        115                 120                 125

Gly Arg Gln Phe Ser Ser Gln Val Ser Ile Leu Ser Ala Met Glu Leu
    130                 135                 140

Ile Trp Asn Leu Cys Glu Ile Leu Phe Ile Glu Val Ala Pro Ala Gly
145                 150                 155                 160

Pro Leu Leu Leu His Leu Leu Asp Trp Val Arg Leu His Val Cys Glu
                165                 170                 175

Val Asp Ser Leu Ser Ala Asp Val Leu Gly Ser Glu Asn Pro Ser Lys
            180                 185                 190

His Asp Ser Phe Trp Asn Leu Val Thr Ile Leu Val Leu Gln Gly Arg
        195                 200                 205

Leu Asp Glu Ala Arg Gln Met Leu Ser Lys Glu Ala Asp Ala Ser Pro
    210                 215                 220

Ala Ser Ala Gly Ile Cys Arg Ile Met Gly Asp Leu Met Arg Thr Met
225                 230                 235                 240

Pro Ile Leu Ser Pro Gly Asn Thr Gln Thr Leu Thr Glu Leu Glu Leu
                245                 250                 255
```

```
Lys Trp Gln His Trp His Glu Glu Cys Glu Arg Tyr Leu Gln Asp Ser
            260                 265                 270

Thr Phe Ala Thr Ser Pro His Leu Glu Ser Leu Leu Lys Ile Met Leu
            275                 280                 285

Gly Asp Glu Ala Ala Leu Leu Glu Gln Lys Glu Leu Leu Ser Asn Trp
            290                 295                 300

Tyr His Phe Leu Val Thr Arg Leu Leu Tyr Ser Asn Pro Thr Val Lys
305                 310                 315                 320

Pro Ile Asp Leu His Tyr Tyr Ala Gln Asp
            325                 330

<210> SEQ ID NO 37
<211> LENGTH: 471
<212> TYPE: DNA
<213> ORGANISM: Homo sapiens
<220> FEATURE:
<221> NAME/KEY: CDS
<222> LOCATION: (1)..(471)

<400> SEQUENCE: 37 ctc gtg tca gac agg ttc ctc agg gat tac tgt gag cga ggc tgc ttt      48
Leu Val Ser Asp Arg Phe Leu Arg Asp Tyr Cys Glu Arg Gly Cys Phe
1               5                   10                  15 tct gat ttg gat ctc att gac aac ctg ggg cca gcc atg atg ctc agt      96
Ser Asp Leu Asp Leu Ile Asp Asn Leu Gly Pro Ala Met Met Leu Ser
            20                  25                  30 gac cga ctg aca ttc ctg gga aag tat cgc gag ttc cac cgt atg tac     144
Asp Arg Leu Thr Phe Leu Gly Lys Tyr Arg Glu Phe His Arg Met Tyr
        35                  40                  45 ggg gag aag cgt ttt gcc gac gca gct tct ctc ctt ctg tcc ttg atg     192
Gly Glu Lys Arg Phe Ala Asp Ala Ala Ser Leu Leu Leu Ser Leu Met
    50                  55                  60 acg tct cgg att gcc cct cgg tct ttc tgg atg act ctg ctg aca gat     240
Thr Ser Arg Ile Ala Pro Arg Ser Phe Trp Met Thr Leu Leu Thr Asp
65                  70                  75                  80 gcc ttg ccc ctt ttg gaa cag aaa cag gtg att ttc tca gca gaa cag     288
Ala Leu Pro Leu Leu Glu Gln Lys Gln Val Ile Phe Ser Ala Glu Gln
                85                  90                  95 act tat gag ttg atg cgg tgt ctg gag gac ttg acg tca aga aga cct     336
Thr Tyr Glu Leu Met Arg Cys Leu Glu Asp Leu Thr Ser Arg Arg Pro
            100                 105                 110 gtg cat gga gaa tct gat acc gag cag ctc cag gat gat gac ata gag     384
Val His Gly Glu Ser Asp Thr Glu Gln Leu Gln Asp Asp Asp Ile Glu
        115                 120                 125 acc acc aag gtg gaa atg ctg aga ctt tct ctg gca cga aat ctt gct     432
Thr Thr Lys Val Glu Met Leu Arg Leu Ser Leu Ala Arg Asn Leu Ala
    130                 135                 140 cgg gca att ata aga gaa ggc tca ctg gaa ggt tcc tga                 471
Arg Ala Ile Ile Arg Glu Gly Ser Leu Glu Gly Ser
145                 150                 155

<210> SEQ ID NO 38
<211> LENGTH: 156
<212> TYPE: PRT
<213> ORGANISM: Homo sapiens

<400> SEQUENCE: 38

Leu Val Ser Asp Arg Phe Leu Arg Asp Tyr Cys Glu Arg Gly Cys Phe
1               5                   10                  15

Ser Asp Leu Asp Leu Ile Asp Asn Leu Gly Pro Ala Met Met Leu Ser
```

```
                    20                  25                  30

Asp Arg Leu Thr Phe Leu Gly Lys Tyr Arg Glu Phe His Arg Met Tyr
            35                  40                  45

Gly Glu Lys Arg Phe Ala Asp Ala Ala Ser Leu Leu Leu Ser Leu Met
        50                  55                  60

Thr Ser Arg Ile Ala Pro Arg Ser Phe Trp Met Thr Leu Leu Thr Asp
 65                  70                  75                  80

Ala Leu Pro Leu Leu Glu Gln Lys Gln Val Ile Phe Ser Ala Glu Gln
                85                  90                  95

Thr Tyr Glu Leu Met Arg Cys Leu Glu Asp Leu Thr Ser Arg Arg Pro
            100                 105                 110

Val His Gly Glu Ser Asp Thr Glu Gln Leu Gln Asp Asp Ile Glu
        115                 120                 125

Thr Thr Lys Val Glu Met Leu Arg Leu Ser Leu Ala Arg Asn Leu Ala
130                 135                 140

Arg Ala Ile Ile Arg Glu Gly Ser Leu Glu Gly Ser
145                 150                 155

<210> SEQ ID NO 39
<211> LENGTH: 227
<212> TYPE: RNA
<213> ORGANISM: Homo sapiens
<220> FEATURE:
<223> OTHER INFORMATION: antisense RNA

<400> SEQUENCE: 39
ucucccuuua auccccuucg caauaguguc cuuuguauac gaauaccuca uuucaaauca    60
agcaguguuu guuccugug ugagucugga aucccagaga gggcgcuaag gggaauacac   120
gcgcacaggc agaacgacaa aggaggaaac acgcacaucg gcaacagcua uacaacuaag   180
cucuagcagg gacugacaag caaagaaaac cacugcugcu gcaaccu               227

<210> SEQ ID NO 40
<211> LENGTH: 227
<212> TYPE: DNA
<213> ORGANISM: Homo sapiens
<220> FEATURE:
<223> OTHER INFORMATION: DNA sequence producing RNA sequence of Seq. No.
      39

<400> SEQUENCE: 40
tctcccttta atcccttcg caatagtgtc ctttgtatac gaatacctca tttcaaatca     60
agcagtgttt gtttcctgtg tgagtctgga atcccagaga gggcgctaag gggaatacac   120
gcgcacaggc agaacgacaa aggaggaaac acgcacatcg gcaacagcta tacaactaag   180
ctctagcagg gactgacaag caaagaaaac cactgctgct gcaacct                227

<210> SEQ ID NO 41
<211> LENGTH: 12
<212> TYPE: PRT
<213> ORGANISM: Homo sapiens

<400> SEQUENCE: 41

Ser Val Phe Phe Arg Lys His Ile Thr Lys Arg Phe
 1               5                  10

<210> SEQ ID NO 42
<211> LENGTH: 26
<212> TYPE: DNA
<213> ORGANISM: Homo sapiens
```

-continued

```
<400> SEQUENCE: 42
gcgaattcga gaagttcaga aggtat                                            26

<210> SEQ ID NO 43
<211> LENGTH: 26
<212> TYPE: DNA
<213> ORGANISM: Homo sapiens

<400> SEQUENCE: 43
gcggatcctt ataaaccagc cgagac                                            26

<210> SEQ ID NO 44
<211> LENGTH: 90
<212> TYPE: DNA
<213> ORGANISM: Homo sapiens

<400> SEQUENCE: 44
aaaattgtaa tacgactcac tatagggcga gccgccacca tggaggagca gaagctgatc       60
tcagaggagg acctggtatc gccggtattg                                        90

<210> SEQ ID NO 45
<211> LENGTH: 21
<212> TYPE: DNA
<213> ORGANISM: Homo sapiens

<400> SEQUENCE: 45
cagctatgac catgattacg c                                                 21

<210> SEQ ID NO 46
<211> LENGTH: 68
<212> TYPE: DNA
<213> ORGANISM: Homo sapiens

<400> SEQUENCE: 46
aaaattgtaa tacgactcac tatagggcga gccgccacca tgtacccata cgacgttcca       60
gattacgc                                                                68

<210> SEQ ID NO 47
<211> LENGTH: 28
<212> TYPE: DNA
<213> ORGANISM: Homo sapiens

<400> SEQUENCE: 47
acttgcgggg tttttcagta tctacgat                                          28

<210> SEQ ID NO 48
<211> LENGTH: 31
<212> TYPE: DNA
<213> ORGANISM: Homo sapiens

<400> SEQUENCE: 48
cccgctcgag ctatgtattt tgactggggt c                                      31

<210> SEQ ID NO 49
<211> LENGTH: 28
<212> TYPE: DNA
<213> ORGANISM: Homo sapiens

<400> SEQUENCE: 49
gcgaattctc aggaaccttc cagtgagc                                          28
```

<210> SEQ ID NO 50
<211> LENGTH: 30
<212> TYPE: DNA
<213> ORGANISM: Homo sapiens

<400> SEQUENCE: 50
cgggatccgc catgtatttt gactggggtc                               30

<210> SEQ ID NO 51
<211> LENGTH: 34
<212> TYPE: DNA
<213> ORGANISM: Homo sapiens

<400> SEQUENCE: 51
gcgaattctc atgacaaaat ggagacctgg ctgc                          34

<210> SEQ ID NO 52
<211> LENGTH: 29
<212> TYPE: DNA
<213> ORGANISM: Homo sapiens

<400> SEQUENCE: 52
gcggatcctc aaatcaagca gtgtttgtc                                29

<210> SEQ ID NO 53
<211> LENGTH: 35
<212> TYPE: DNA
<213> ORGANISM: Homo sapiens

<400> SEQUENCE: 53
cgggatccgc catgcttttg aacagaaac aggtg                          35

<210> SEQ ID NO 54
<211> LENGTH: 26
<212> TYPE: DNA
<213> ORGANISM: Homo sapiens

<400> SEQUENCE: 54
cctcggtctt tctggatgac tctgct                                   26

<210> SEQ ID NO 55
<211> LENGTH: 19
<212> TYPE: DNA
<213> ORGANISM: Homo sapiens

<400> SEQUENCE: 55
cagccatgat gctcagtga                                           19

<210> SEQ ID NO 56
<211> LENGTH: 22
<212> TYPE: DNA
<213> ORGANISM: Homo sapiens

<400> SEQUENCE: 56
tggtctctat gtcatcatcc tg                                       22

<210> SEQ ID NO 57
<211> LENGTH: 28
<212> TYPE: DNA
<213> ORGANISM: Homo sapiens

<400> SEQUENCE: 57
gcgaattcgc ggatcccgcc gcgtcgac                                 28

<210> SEQ ID NO 58
<211> LENGTH: 28
<212> TYPE: DNA
<213> ORGANISM: Homo sapiens

<400> SEQUENCE: 58
gcgaattcgg ggttttcag tatctacg                                         28

<210> SEQ ID NO 59
<211> LENGTH: 31
<212> TYPE: DNA
<213> ORGANISM: Mus musculus

<400> SEQUENCE: 59
gcggatccat ggaggagctc gatggcgagc c                                    31

<210> SEQ ID NO 60
<211> LENGTH: 28
<212> TYPE: DNA
<213> ORGANISM: Mus musculus

<400> SEQUENCE: 60
gcggatcctc aggaaccttc cagtgagc                                        28

<210> SEQ ID NO 61
<211> LENGTH: 52
<212> TYPE: PRT
<213> ORGANISM: Homo sapiens

<400> SEQUENCE: 61

Gly Glu Lys Phe Arg Arg Tyr Leu Ser Val Phe Phe Arg Lys His Ile
 1               5                  10                  15

Thr Lys Arg Phe Cys Lys Gln Cys Pro Val Phe Tyr Arg Glu Thr Val
            20                  25                  30

Asp Gly Val Thr Ser Thr Asn Thr Pro Ser Thr Gly Glu Gln Glu Val
        35                  40                  45

Ser Ala Gly Leu
        50

<210> SEQ ID NO 62
<211> LENGTH: 48
<212> TYPE: PRT
<213> ORGANISM: Homo sapiens

<400> SEQUENCE: 62

Gly Glu Lys Phe Arg Arg Tyr Leu Ser Val Phe Phe Arg Lys His Ile
 1               5                  10                  15

Thr Lys Arg Phe Cys Lys Gln Cys Pro Val Phe Tyr Arg Glu Thr Val
            20                  25                  30

Asp Gly Val Thr Ser Thr Asn Thr Pro Ser Thr Gly Glu Gln Glu Val
        35                  40                  45

<210> SEQ ID NO 63
<211> LENGTH: 33
<212> TYPE: PRT
<213> ORGANISM: Homo sapiens

<400> SEQUENCE: 63

Gly Glu Lys Phe Arg Arg Tyr Leu Ser Val Phe Phe Arg Lys His Ile
 1               5                  10                  15

```
Thr Lys Arg Phe Cys Lys Gln Cys Pro Val Phe Tyr Arg Glu Thr Val
            20                  25                  30
Asp

<210> SEQ ID NO 64
<211> LENGTH: 20
<212> TYPE: PRT
<213> ORGANISM: Homo sapiens

<400> SEQUENCE: 64

Gly Glu Lys Phe Arg Arg Tyr Leu Ser Val Phe Phe Arg Lys His Ile
 1               5                  10                  15

Thr Lys Arg Phe
            20

<210> SEQ ID NO 65
<211> LENGTH: 20
<212> TYPE: PRT
<213> ORGANISM: Homo sapiens

<400> SEQUENCE: 65

Gly Glu Lys Phe Arg Arg Tyr Leu Ser Val Phe Phe Arg Lys His Ile
 1               5                  10                  15

Ala Lys Arg Phe
            20

<210> SEQ ID NO 66
<211> LENGTH: 20
<212> TYPE: PRT
<213> ORGANISM: Homo sapiens

<400> SEQUENCE: 66

Gly Glu Lys Phe Arg Arg Tyr Leu Ala Val Phe Phe Arg Lys His Ile
 1               5                  10                  15

Thr Lys Arg Phe
            20

<210> SEQ ID NO 67
<211> LENGTH: 20
<212> TYPE: PRT
<213> ORGANISM: Homo sapiens

<400> SEQUENCE: 67

Gly Glu Lys Phe Arg Arg Tyr Leu Ala Val Phe Phe Arg Lys His Ile
 1               5                  10                  15

Ala Lys Arg Phe
            20

<210> SEQ ID NO 68
<211> LENGTH: 8
<212> TYPE: PRT
<213> ORGANISM: Homo sapiens

<400> SEQUENCE: 68

Gly Glu Lys Phe Arg Arg Tyr Leu
 1               5

<210> SEQ ID NO 69
<211> LENGTH: 46
<212> TYPE: PRT
<213> ORGANISM: Homo sapiens

<400> SEQUENCE: 69
```

```
Ala Lys Phe Lys Thr Ser Ala Gln His Ala Leu Thr Ser Val Ser Arg
 1               5                  10                  15

Gly Ser Ser Leu Lys Ile Leu Ser Lys Gly Lys Arg Gly Gly His Ser
                20                  25                  30

Ser Val Ser Thr Glu Ser Glu Ser Ser Ser Phe His Ser Ser
                35                  40                  45
```